(12) United States Patent
Albert et al.

(10) Patent No.: US 11,268,120 B2
(45) Date of Patent: Mar. 8, 2022

(54) IDENTIFICATION OF TRANSGLUTAMINASE SUBSTRATES AND USES THEREFOR

(71) Applicant: Roche Sequencing Solutions, Inc., Pleasanton, CA (US)

(72) Inventors: Thomas Albert, Verona, WI (US); Frank Bergmann, Iffeldorf (DE); Victor Lyamichev, Madison, WI (US); Jigar Patel, Verona, WI (US); Michael Schraeml, Penzberg (DE); Wojtek Steffen, Penzberg (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 15/625,784

(22) Filed: Jun. 16, 2017

(65) Prior Publication Data

US 2017/0314054 A1    Nov. 2, 2017

Related U.S. Application Data

(63) Continuation of application No. PCT/EP2015/079689, filed on Dec. 15, 2015.

(60) Provisional application No. 62/094,495, filed on Dec. 19, 2014.

(51) Int. Cl.

| | |
|---|---|
| *C07K 16/28* | (2006.01) |
| *C07K 16/30* | (2006.01) |
| *A61K 38/08* | (2019.01) |
| *C12P 21/02* | (2006.01) |
| *C12N 9/10* | (2006.01) |
| *C07K 14/47* | (2006.01) |
| *C07K 1/107* | (2006.01) |
| *C07K 1/13* | (2006.01) |
| *C07K 14/00* | (2006.01) |

(52) U.S. Cl.
CPC ............ *C12P 21/02* (2013.01); *C07K 1/1075* (2013.01); *C07K 1/13* (2013.01); *C07K 14/00* (2013.01); *C07K 14/4717* (2013.01); *C12N 9/1044* (2013.01); *C07K 2319/21* (2013.01)

(58) Field of Classification Search
CPC ...... C07K 7/06; C12N 9/1044; G01N 33/573; C12Y 203/01013
USPC ........................... 435/7.4, 193; 530/328, 330
See application file for complete search history.

(56) References Cited

U.S. PATENT DOCUMENTS

2012/0190561 A1    7/2012  Wildt et al.

FOREIGN PATENT DOCUMENTS

| CA | 2402563 A1 | 7/2001 |
|---|---|---|
| CA | 2902841 A1 | 10/2014 |
| WO | 2012059882 A2 | 5/2012 |
| WO | 2013163162 A1 | 10/2013 |
| WO | 2013130953 A2 | 10/2014 |
| WO | WO-2014/160499 A2 | 10/2014 |

OTHER PUBLICATIONS

Bowie et al. Science, 1990, 247:1306-1310.*
Burgess et al. J. Cell Biol. 111:2129-2138, 1990.*
Lazar et al. Mol. Cell. Biol., 8:1247-1252, 1988.*
Tagami et al. Proteng. and Design 2009, 22, pp. 747-752.*
Hemung, B.-O. et al., Reactivity of Fish and Microbial Transglutaminases on Glutaminyl Sites of Peptides Derived from Threadfin Bream Myosin, J. Agric. Food Chem., (2008), pp. 7510-7516, vol. 56 No. 16.
Kuramoto, K. et al., Phage-displayed peptide library screening for preferred human substrate peptide sequences for transglutaminase 7, Archives of Biochemistry and Biophysics, (2013), pp. 138-143, vol. 537 Issue 1.
Sugimura, Y. et al., Identification of preferred substrate sequences of microbial transglutaminase from Streptomyces mobaraensis using a phage-displayed peptide library, Archives of Biochemistry and Biophysics, (2008), pp. 379-383, vol. 477 Issue 2.
International Search Report and Written Opinion dated Apr. 1, 2016 in corresponding PCT Application No. PCT/EP2015/079689 filed Dec. 15, 2015, pp. 1-16.
Antos, et al., "Recent Advances in Sortase-Catalyzed Ligation Methodology," Curr Opin Struct Biol. 38:111-118 (2016).
Fairhead and Howarth, "Site-specific biotinylation of purified proteins using BirA," Methods Mol Biol. 1266:171-184 (2015).
Hatlem, et al.,"Catching a SPY: Using the SpyCatcher-SpyTag and Related Systems for Labeling and Localizing Bacterial Proteins," International Journal of Molecular Sciences 20:2129 (2019).
Jeger, et al.,"Site-Specific and Stoichiometric Modification of Antibodies by Bacterial Transglutaminase," Angewandte Chemie 49:9995-9997 (2010).
Wang and Chen, "Site-specifically modified fusion proteins for molecular imaging," Frontiers in Bioscience 13:1716-1732 (2008).
First Office Action in CN Patent Application No. 201580076526.0 dated Jun. 1, 2020 (with English translation) (6 pages).
Office Action mailed in CN 201580076526.0 dated Jun. 2, 2021, 11 pages including English translation.

* cited by examiner

*Primary Examiner* — Robert B Mondesi
*Assistant Examiner* — Mohammad Y Meah
(74) *Attorney, Agent, or Firm* — Foley & Lardner LLP; Joseph P. Meara

(57) ABSTRACT

According to one aspect, the present disclosure provides a method of identifying a substrate of a transglutaminase using a peptide array comprising a plurality of peptides. The method includes the steps of contacting the peptides in the peptide array with the transglutaminase, allowing the transglutaminase to bind to the peptides, and identifying the substrate of the transglutaminase.

17 Claims, 12 Drawing Sheets

Specification includes a Sequence Listing.

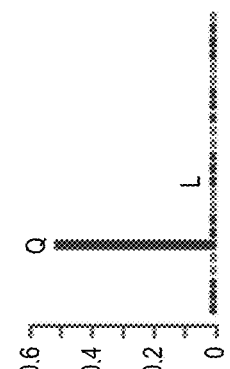
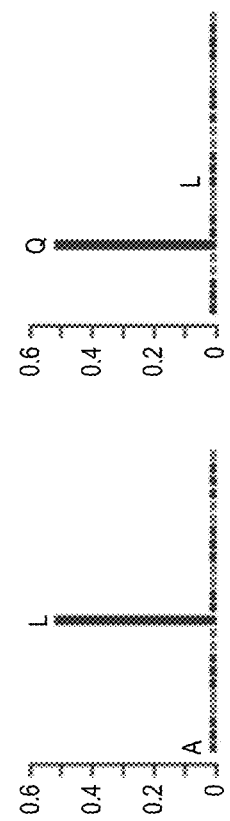
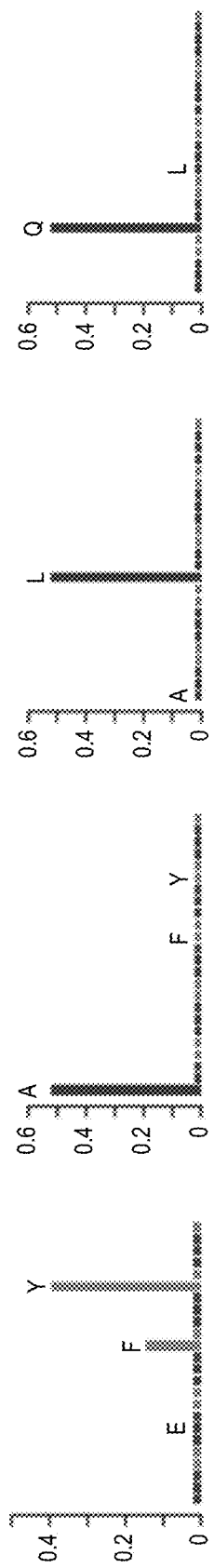
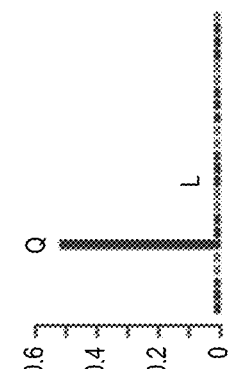
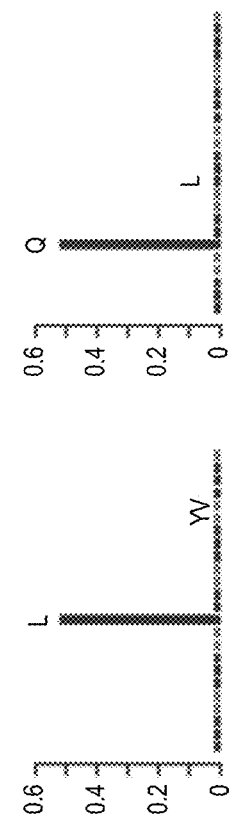
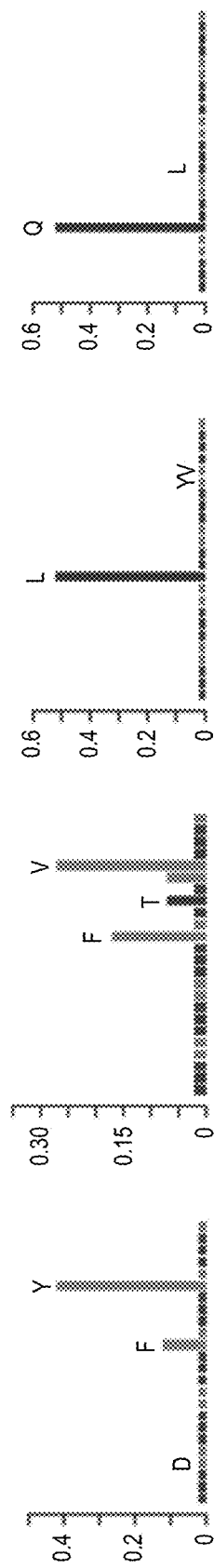
FIG. 2A FIG. 2B FIG. 2C FIG. 2D
FIG. 2E FIG. 2F FIG. 2G FIG. 2H

IDENTIFICATION OF TRANSGLUTAMINASE SUBSTRATES AND USES THEREFOR

CROSS-REFERENCE TO RELATED APPLICATIONS

This patent application is a continuation of International Patent Application No. PCT/EP2015/079689 filed Dec. 15, 2015, which claims priority to and the benefit of U.S. Provisional Application No. 62/094,495, filed Dec. 19, 2014. Each of the above patent applications is incorporated herein by reference as if set forth in its entirety.

BACKGROUND OF THE INVENTION

The disclosure relates, in general, to peptide arrays comprising transglutaminase substrates, and methods of identifying transglutaminase substrates using peptide arrays. The disclosure also relates to transglutaminase substrate peptides and methods of their use to cross-link peptides and proteins.

Elucidating the details of enzyme activity and specificity is important for understanding the physiological function of enzymes and for biotechnological applications of the reactions catalyzed by enzymes. For example, transglutaminases belong to a large family of related enzymes, including microbial and mammalian transglutaminases. Transglutaminases catalyze cross-linking between two polypeptide or peptide chains by forming an isopeptide bond between a gamma-carboxamide group of a glutamine residue and an epsilon-amino group of a lysine residue. Elucidating the details of transglutaminase activity and specificity is important for biotechnological applications of the cross-linking reaction catalyzed by transglutaminases, for example, for modification of proteins for labeling, tagging, multi-protein complex formation, and the like.

To date, microbial transglutaminase is the most studied transglutaminase enzyme because of its small size, robust performance, stability, and the calcium independence of its activity. Several studies have shown that a broad variety of long alkylamines can substitute for the lysine substrate of transglutaminases and the simple dipeptide Glutamine-Glycine (QG) can serve as the glutamine substrate. These discoveries of lysine and glutamine substrates of transglutaminases have helped to develop a variety of tests for transglutaminase activity and practical assays for modification of proteins using transglutaminases.

One challenge is that the identification of synthetic peptides as enzyme substrates is limited by the potentially large number of molecules that could be tested. This obstacle might be overcome by using peptide libraries and selection techniques, such as phage display or mRNA display. By using these approaches preferred substrate sequences have been identified. However, the wide diversity of sequences makes finding common substrate motifs, for example transglutaminase substrate motifs, difficult. Accordingly, there is a need for fast, inexpensive, and systematic methods that could address identification of transglutaminase substrates and common substrate motifs which have many important applications.

SUMMARY OF THE INVENTION

The present invention overcomes the aforementioned drawbacks by providing a system and method for the identification of transglutaminase substrates, as well as uses therefor.

Applicants have discovered a fast, reliable, and systematic approach to identify both substrate sequences specifically recognized by enzymes, and common substrate motifs. In one illustrative aspect, a library of at least 1 million 5-mer transglutaminase substrate peptides is synthesized on a peptide array, for example, using maskless light-directed peptide array technology. The peptide array is then screened for enzyme activity to identify preferred enzyme substrates or substrate motifs.

In another embodiment, a library of at least 1 million 5-mer transglutaminase substrate peptides is synthesized on a peptide array, for example, using maskless light-directed peptide array technology. The peptide array is then screened for enzyme activity to identify preferred enzyme substrates. A second, newly designed, focused peptide library containing extended and mutated variants of the sequences identified in the first step is then synthesized on a new array to select peptides with optimal enzyme specificity in the peptide space around identified motifs. The high density of peptide arrays allows screening of a large number of peptides, thus providing a comprehensive and reproducible initial screen of transglutaminase substrates. Moreover, the ability to rapidly search the peptide space in the vicinity of the originally identified substrate hits is possible due to techniques for creating a new array in a few days, for example, using maskless light-directed peptide synthesis.

In accordance with one embodiment of the present disclosure, a method of identifying a substrate of a transglutaminase using a peptide array including a plurality of peptides includes the steps of contacting the peptides in the peptide array with the transglutaminase, allowing the transglutaminase to bind to the peptides, and identifying the substrate of the transglutaminase.

In one aspect, the peptide array comprises a solid support.

In another aspect, the peptides are attached to the solid support by maskless light-directed peptide array synthesis.

In another aspect, the peptide array has at least $1.2 \times 10^6$ peptides attached to the solid support.

In another aspect, the peptide array has at least $1.4 \times 10^6$ peptides attached to the solid support.

In another aspect, the peptide array has at least $1.6 \times 10^6$ peptides attached to the solid support.

In another aspect, the peptide array has at least $1.8 \times 10^6$ peptides attached to the solid support.

In another aspect, the transglutaminase is a microbial transglutaminase.

In another aspect, the microbial transglutaminase is a *Streptoverticillium* sp. transglutaminase.

In another aspect, the transglutaminase is a mammalian transglutaminase.

In another aspect, the mammalian transglutaminase is selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

In another aspect, the transglutaminase substrate is a glutamine substrate peptide.

In another aspect, the transglutaminase substrate is a lysine substrate peptide.

In another aspect, the glutamine substrate peptide includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), and NFVLQ (SEQ ID NO:25), or a combination thereof.

In another aspect, the lysine substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another aspect, the glutamine substrate peptide has a glutamine residue in the fifth position.

In another aspect, the glutamine substrate peptide has a sequence motif including [YF][VA]LQG.

In another aspect, the glutamine substrate peptide has a sequence including DYALQ (SEQ ID NO: 1).

In another aspect, the lysine substrate peptide has a sequence motif including SK[LS]K or [KR][ST]KL.

In accordance with another embodiment of the present disclosure, a method of identifying a substrate of a transglutaminase using one or more peptide arrays including a plurality of peptides includes the steps of contacting the peptides in a first peptide array with the transglutaminase, allowing the transglutaminase to bind to the peptides in the first peptide array, selecting one or more of the peptides in the first peptide array that exhibit a predetermined property upon binding to the transglutaminase, synthesizing variants of the one or more peptides that are identified in the first peptide array, contacting the variant peptides in a second peptide array with the transglutaminase, and selecting one or more of the variant peptides that are identified in the second peptide array as exhibiting the predetermined property upon binding to the transglutaminase.

In one aspect, the peptides in the first or the second peptide array are selected from the group consisting of 5-mers, 6-mers, 7-mers, 8-mers, 9-mers, 10-mers, 11-mers, and 12-mers, or a combination thereof.

In another aspect, the first peptide array and the second peptide array each include a solid support.

In another aspect, the peptide array is made by maskless light-directed peptide array synthesis.

In another aspect, the second peptide array has at least $1.0 \times 10^6$ peptides attached to the solid support of the second peptide array.

In another aspect, the first peptide array and/or the second peptide array have at least $1.2 \times 10^6$ peptides attached to the solid support.

In another aspect, the first peptide array and/or the second peptide array have at least $1.4 \times 10^6$ peptides attached to the solid support.

In another aspect, the first peptide array and/or the second peptide array have at least $1.6 \times 10^6$ peptides attached to the solid support.

In another aspect, the transglutaminase is a microbial transglutaminase.

In another aspect, the microbial transglutaminase is a *Streptoverticillium* sp. transglutaminase.

In another aspect, the transglutaminase is a mammalian transglutaminase.

In another aspect, the mammalian transglutaminase is selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

In another aspect, the variant peptide selected is a transglutaminase glutamine substrate peptide.

In another aspect, the glutamine substrate peptide includes a sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), or a combination thereof.

In another aspect, the glutamine substrate peptide includes a sequence motif of GDYALQGPG (SEQ ID NO: 79).

In another aspect, the glutamine substrate peptide has a sequence including GGGDYALQGGG (SEQ ID NO: 26).

In another aspect, the selected peptide from the first peptide array includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), and NFVLQ (SEQ ID NO:25), or a combination thereof.

In another aspect, the selected peptide from the first peptide array includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another aspect, the selected peptide has a glutamine residue in the fifth position.

In another aspect, the selected peptide has a sequence motif including [YF][VA]LQG.

In another aspect, the selected peptide has a sequence including DYALQ (SEQ ID NO: 1).

In another aspect, the selected peptide has a sequence motif including SK[LS]K or [KR][ST]KL.

In accordance with another embodiment of the present disclosure, a peptide array includes a solid support and a plurality of peptides. The peptides are transglutaminase substrate peptides, and the peptide array is made by maskless light-directed peptide array synthesis.

In accordance with another embodiment of the present disclosure, an isolated peptide includes a sequence motif of GDYALQGPG (SEQ ID NO: 79).

In accordance with another embodiment of the present disclosure, an isolated peptide includes a sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), or a combination thereof.

In one aspect, the peptide includes the sequence GGGDYALQGGG (SEQ ID NO: 26).

In another aspect, the peptide includes a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In accordance with another embodiment of the present disclosure, a protein includes a heterologous transglutaminase substrate peptide sequence including a sequence motif of [YF][VA]LQG.

In accordance with another embodiment of the present disclosure, a protein includes a heterologous transglutaminase substrate peptide including a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), and NFVLQ (SEQ ID NO:25), or a combination thereof.

In one aspect, the protein includes a heterologous transglutaminase substrate peptide including a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In accordance with another embodiment of the present disclosure, a protein includes a heterologous transglutaminase substrate peptide including a sequence motif of SK[LS]K or [KR][ST]KL.

In accordance with another embodiment of the present disclosure, a protein includes a heterologous transglutaminase substrate peptide sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In one aspect, the protein includes a heterologous transglutaminase substrate peptide including a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof.

In accordance with another embodiment of the present disclosure, a protein includes a heterologous transglutaminase substrate peptide sequence including a sequence motif of GDYALQGPG (SEQ ID NO: 79).

In accordance with another embodiment of the present disclosure, a protein includes a heterologous transglutaminase substrate peptide sequence including a sequence of DYALQ (SEQ ID NO: 1).

In one aspect, the protein includes a heterologous transglutaminase substrate peptide sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), or a combination thereof.

In another aspect, the sequence includes GGGDYALQGGG (SEQ ID NO: 26).

In another aspect, the protein includes a heterologous transglutaminase substrate peptide including a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In accordance with another embodiment of the present disclosure, a method for crossing-linking a protein includes the steps of incorporating at least one heterologous transglutaminase substrate peptide sequence into the protein, and cross-linking the protein by contacting the protein with a transglutaminase. The heterologous transglutaminase peptide sequence includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In one aspect, the heterologous transglutaminase peptide sequence includes the sequence DYALQ (SEQ ID NO: 1).

In another aspect, the heterologous transglutaminase peptide sequence includes the sequence GGGDYALQGGG (SEQ ID NO: 26).

In accordance with another embodiment of the present disclosure, a method for crossing-linking a protein including the steps of incorporating at least one heterologous transglutaminase substrate peptide sequence into the protein, and cross-linking the protein by contacting the protein with a transglutaminase. The heterologous transglutaminase peptide sequence includes a sequence motif selected from the group consisting of SK[LS]K, [KR][ST]KL, [YF][VA]LQG, and GDYALQGPG (SEQ ID NO: 79), or a combination thereof.

In one aspect, the heterologous transglutaminase substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof.

In another aspect, the heterologous transglutaminase substrate peptide includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In another aspect, the heterologous transglutaminase substrate peptide includes a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In accordance with another embodiment of the present disclosure, a method for cross-linking at least two compounds includes the steps of incorporating a heterologous transglutaminase glutamine substrate peptide with a sequence motif of [YF][VA]LQG or GDYALQGPG (SEQ ID NO: 79) into one of the at least two compounds, and cross-linking the compounds by contacting the compounds with a transglutaminase.

In one aspect, the method further includes the step of incorporating a heterologous transglutaminase lysine substrate peptide into the protein.

In another aspect, the lysine substrate peptide includes a sequence motif of SK[LS]K or [KR][ST]KL.

In another aspect, the heterologous transglutaminase lysine substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof.

In another aspect, the heterologous transglutaminase glutamine substrate peptide includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In another aspect, the heterologous transglutaminase glutamine substrate peptide includes a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In accordance with another embodiment of the present disclosure, a method for cross-linking at least two compounds includes the steps of incorporating a heterologous transglutaminase glutamine substrate peptide including a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), and GGGDYALQGGGG (SEQ ID NO: 86), or a combination thereof, into one of the at least two compounds, and cross-linking the compounds by contacting the compounds with a transglutaminase.

In one aspect, the method further includes the step of incorporating a heterologous transglutaminase lysine substrate peptide into the other of the at least two compounds.

In another aspect, the lysine substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another aspect, the compounds are selected from the group consisting of a protein, a peptide, and a small organic molecule, or a combination thereof.

In another aspect, the glutamine substrate peptide has a sequence including DYALQ (SEQ ID NO: 1).

In accordance with another embodiment of the present disclosure, a method for cross-linking a protein includes the steps of incorporating a heterologous transglutaminase glutamine substrate peptide with a sequence motif of [YF][VA]LQG or GDYALQGPG (SEQ ID NO: 79) into the protein, incorporating a transglutaminase lysine substrate peptide into the protein, and cross-linking the protein by contacting the protein with a transglutaminase.

In one aspect, the lysine substrate peptide includes a sequence motif of SK[LS]K or [KR][ST]KL.

In another aspect, the heterologous transglutaminase lysine substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof.

In another aspect, the heterologous transglutaminase glutamine substrate peptide includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In another aspect, the heterologous transglutaminase glutamine substrate peptide includes a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In another aspect, the glutamine substrate peptide includes the sequence DYALQ (SEQ ID NO: 1).

In accordance with another embodiment of the present disclosure, a method for cross-linking a protein includes the steps of incorporating a heterologous transglutaminase glutamine substrate peptide wherein the peptide includes a sequence selected from the group consisting of DYALQ (SEQ ID NO: 1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), and GGGDYALQGGGG (SEQ ID NO: 86), or a combination thereof, into the protein.

The method further includes the steps of incorporating a transglutaminase lysine substrate peptide into the protein, and cross-linking the protein by contacting the protein with a transglutaminase.

In one aspect, the transglutaminase lysine substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another aspect, the cross-linking method is used to conjugate a targeting ligand to a drug.

In another aspect, the cross-linking method is used for conjugation of an affinity tag.

In another aspect, the cross-linking method is used for conjugation of a label.

In another aspect, the cross-linking method is used for PEGylation.

In another aspect, the cross-linking method is used for biotinylation or ruthenylation.

In another aspect, the protein is a Vitamin D binding protein.

In another aspect, one of the compounds is a Vitamin D binding protein.

In another aspect, the other compound is a label wherein the label is Cy5, ruthenium, or biotin.

In another aspect, the label is Cy5.

In another aspect, the label is ruthenium.

In another aspect, the label is biotin.

In another aspect, the heterologous transglutaminase glutamine substrate peptide is incorporated into the Vitamin D binding protein and the peptide includes the sequence GGGGDYALQGGGG (SEQ ID NO: 85).

In another aspect, the heterologous transglutaminase lysine substrate peptide is incorporated into the label.

In another aspect, the heterologous transglutaminase lysine substrate peptide incorporated into the label includes the sequence RSKLG (SEQ ID NO:58).

In another aspect, the label with the incorporated heterologous transglutaminase lysine substrate peptide is a compound of formula:

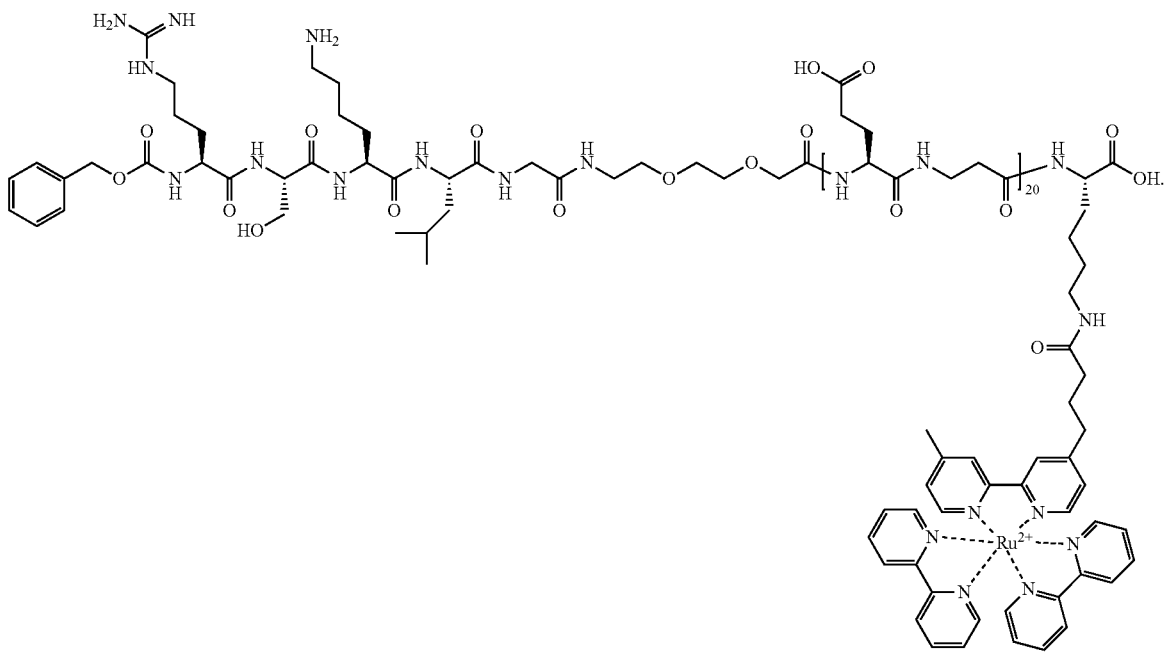

In another aspect, the label with the incorporated heterologous transglutaminase lysine substrate peptide is a compound of formula:

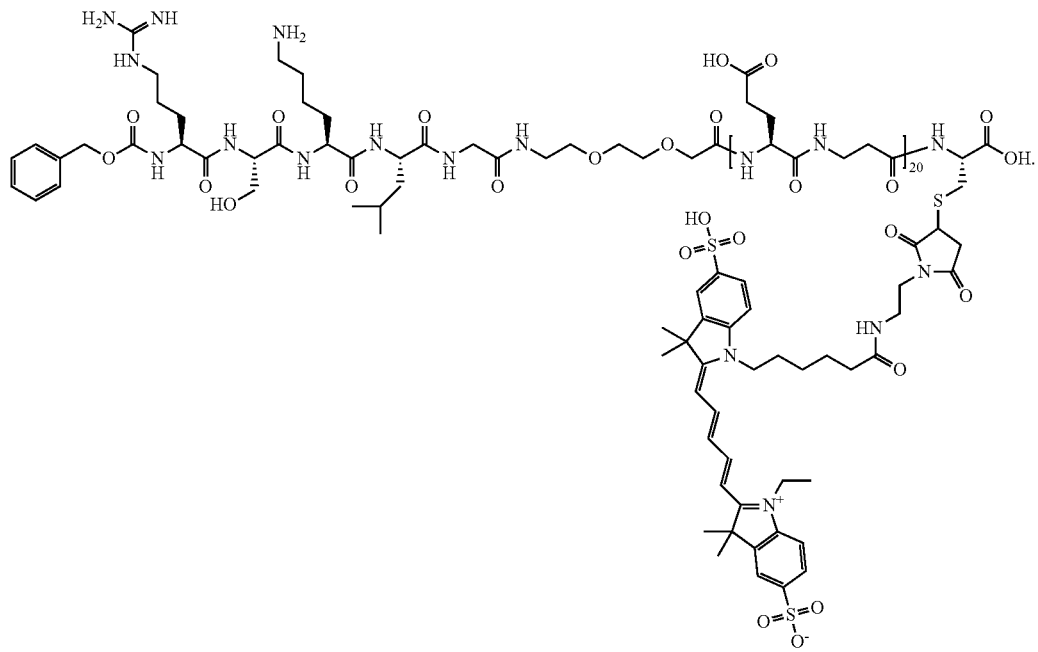

In another aspect, the label with the incorporated heterologous transglutaminase lysine substrate peptide is a compound of formula:

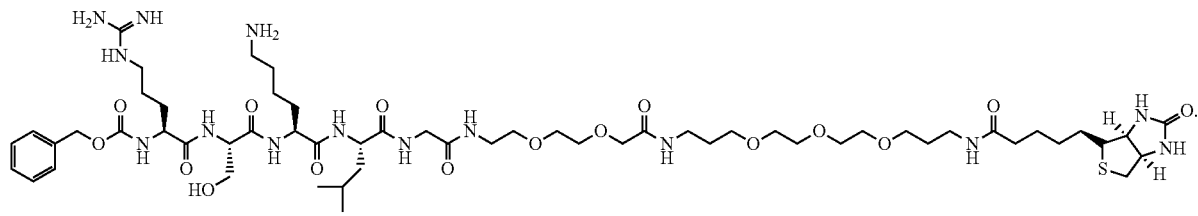

In accordance with another embodiment of the present disclosure, a vitamin D binding protein includes a heterologous transglutaminase substrate peptide sequence.

In one aspect, the transglutaminase substrate peptide includes a sequence motif selected from the group consisting of [YF][VA]LQG, GDYALQGPG (SEQ ID NO: 79), SK[LS]K, and [KR][ST]KL, or a combination thereof.

In another aspect, the heterologous transglutaminase substrate peptide includes a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), NFVLQ (SEQ ID NO:25), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDY-ALQGPG (SEQ ID NO: 53), or a combination thereof.

In another aspect, the transglutaminase substrate peptide includes the sequence DYALQ (SEQ ID NO: 1).

In accordance with another embodiment of the present disclosure, a vitamin D binding protein includes a heterologous transglutaminase glutamine substrate peptide wherein the peptide includes a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In one aspect, the peptide includes the sequence GGGGDYALQGGGG (SEQ ID NO: 85).

In another aspect, the peptides in the peptide array are selected from the group consisting of 5-mers, 6-mers, 7-mers, 8-mers, 9-mers, 10-mers, 11-mers, and 12-mers, or a combination thereof.

In another aspect, the peptides lack cysteine.

In another aspect, the peptides lack amino acid repeats.

In another aspect, the peptides represent all transglutaminase substrates with a length selected from the group consisting of 5-mers, 6-mers, 7-mers, 8-mers, 9-mers, 10-mers, 11-mers, and 12-mers, or a combination thereof.

In accordance with another embodiment of the present disclosure, a vitamin D binding protein has the sequence:

```
                                        (SEQ ID NO: 91)
LERGRDYEKNKVCKEFSHLGKEDFTSLSLVLYSRKFPSGTFEQVSQLVKE

VVSLTEACCAEGADPDCYDTRTSALSAKSCESNSPFPVHPGTAECCTKEG

LERKLCMAALKHQPQEFPTYVEPTNDEICEAFRKDPKEYANQFMWEYSTN

YGQAPLSLLVSYTKSYLSMVGSCCTSASPTVCFLKERLQLKHLSLLTTLS

NRVCSQYAAYGEKKSRLSNLIKLAQKVPTADLEDVLPLAEDITNILSKCC

ESASEDCMAKELPEHTVKLCDNLSTKNSKFEDCCQEKTAMDVFVCTYFMP

AAQLPELPDVELPTNKDVCDPGNTKVMDKYTFELSRRTHLPEVFLSKVLE

PTLKSLGECCDVEDSTTCFNAKGPLLKKELSSFIDKGQELCADYSENTFT

EYKKKLAERLKAKLPDATPTELAKLVNKRSDFASNCCSINSPPLYCDSEI

DAELKNILGGGSHHHHHHHGGGGDYALQGGGG.
```

In one aspect, the peptide array includes a number of peptides selected from the group consisting of at least $1.6 \times 10^5$ peptides, at least $2.0 \times 10^5$ peptides, at least $3.0 \times 10^5$ peptides, at least $4.0 \times 10^5$ peptides, at least $5.0 \times 10^5$ peptides, at least $6.0 \times 10^5$ peptides, at least $7.0 \times 10^5$ peptides, at least $8.0 \times 10^5$ peptides, at least $9.0 \times 10^5$ peptides, at least $1.0 \times 10^6$ peptides, at least $1.2 \times 10^6$ peptides, at least $1.4 \times 10^6$ peptides, at least $1.6 \times 10^6$ peptides, at least $1.8 \times 10^6$ peptides, at least $1.0 \times 10^7$ peptides, and at least $1.0 \times 10^8$ peptides attached to the solid support of the peptide array.

In another aspect, the method is used for conjugation of a label, with an attached transglutaminase lysine substrate peptide, of any one of the formulae:

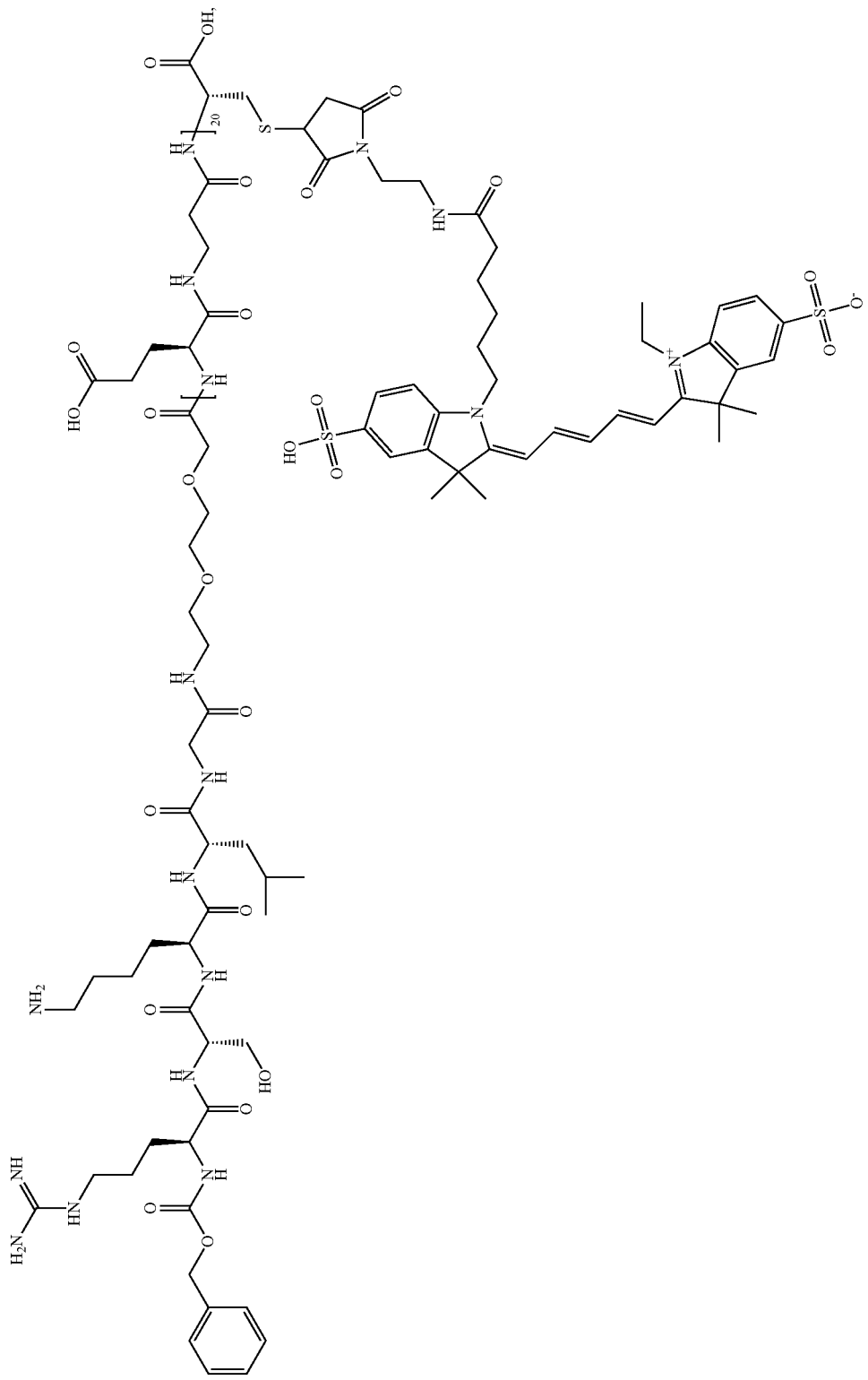

-continued
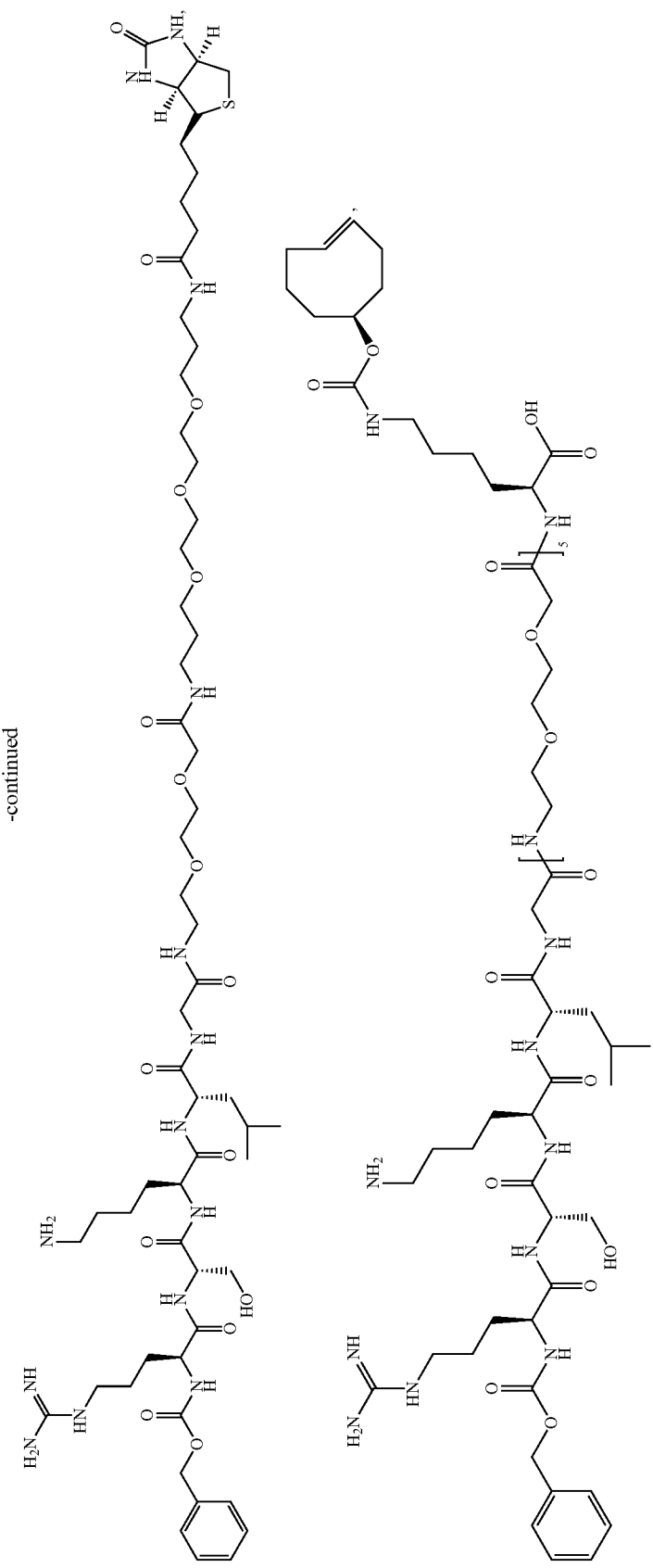

-continued
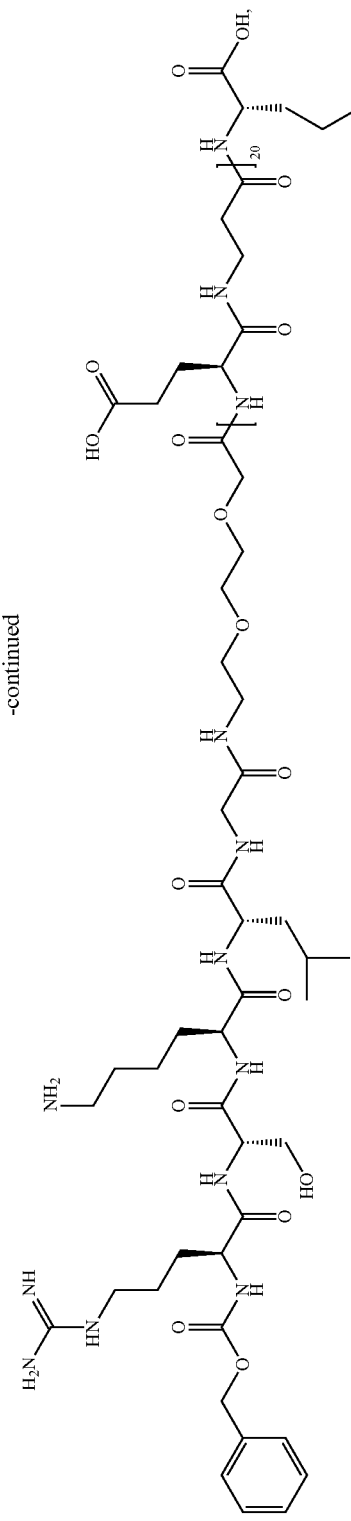
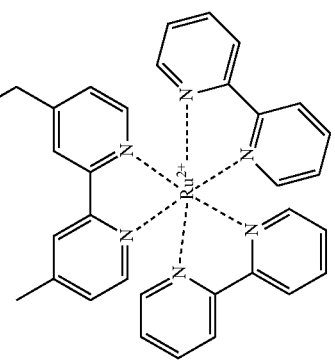

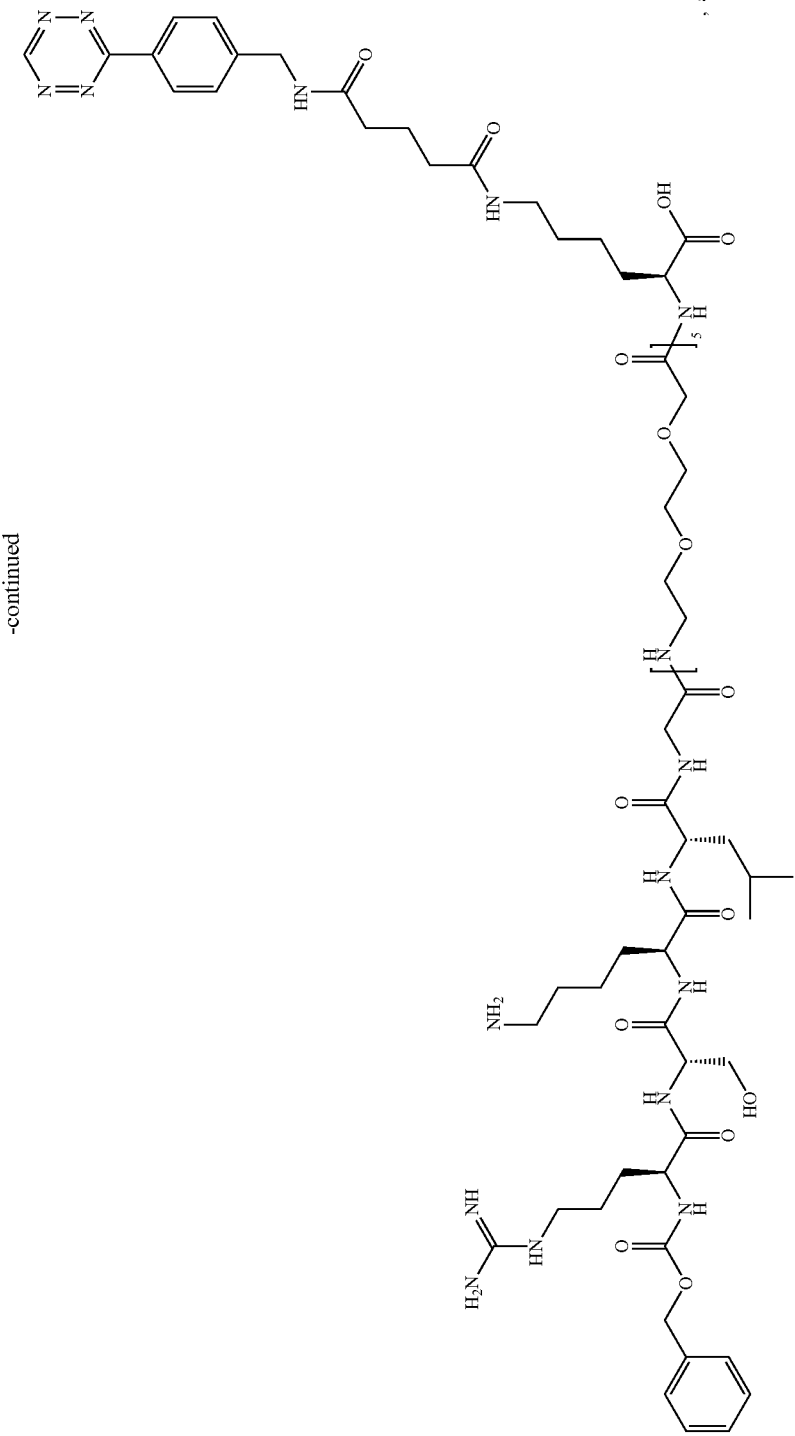, and

-continued
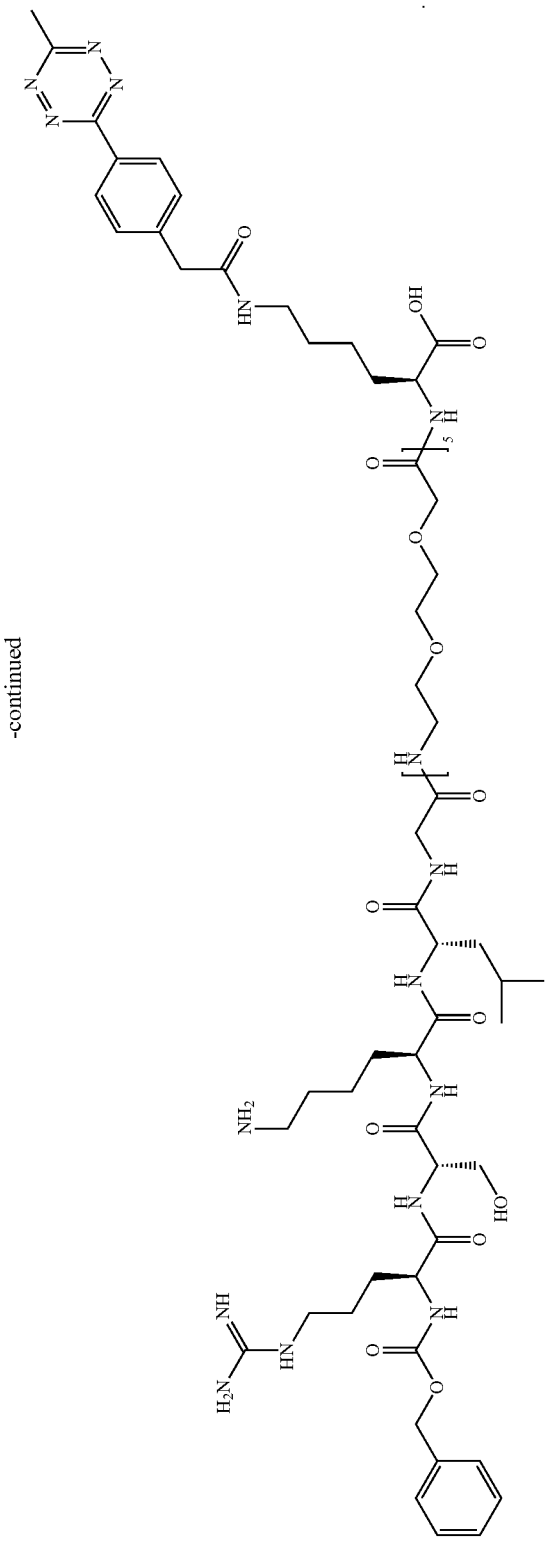

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

SEQUENCE LISTING INCORPORATION BY REFERENCE

This application hereby incorporates-by-reference a sequence listing submitted herewith in a computer-readable format, having a file name of Sequence_Listing_32469 v2_ST25, created on Jun. 15, 2017, which is 26,079 bytes in size.

BRIEF DESCRIPTION OF THE DRAWINGS

FIGS. 2A-2H are amino acid frequency plots for the four most conserved positions for two discovered motifs A and B. FIGS. 2A-2D correspond to positions 1-4 of motif A, respectively. FIGS. 2E-2H correspond to positions 1-4 of motif B, respectively. Motifs were identified using Peplib analysis of top peptide sequences discovered by array MTG assay with biotinylated amine door substrate. Motif A: [Y][A][L][Q]. Motif B: [Y][VF][L][Q]. Amino acids are listed along the horizontal axis from left to right in the following order (single letter code): A, R, N, D, C, E, Q, G, H, I, L, K, M, F, P, S, T, W, Y, V. The frequency of each amino acid is indicated on the vertical axis.

US 11,268,120 B2

DETAILED DESCRIPTION OF THE INVENTION

I. Overview

Figure 1:
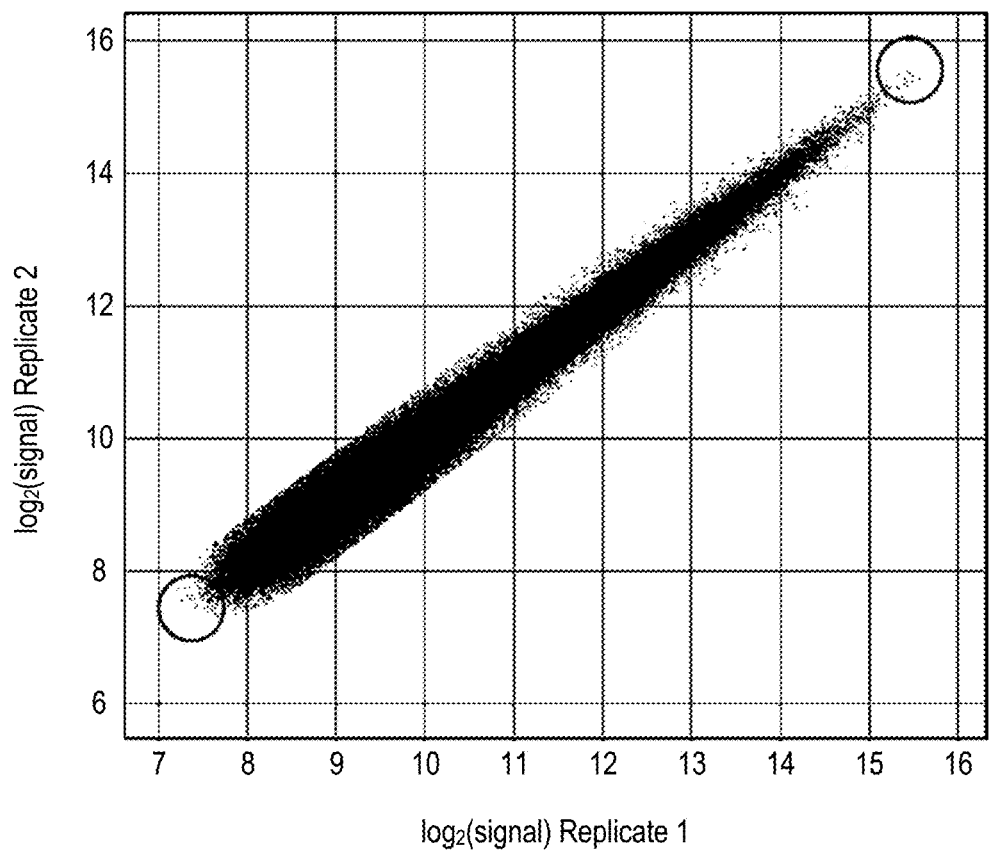
FIG. 1 is a log-log scatter plot showing the correlation between fluorescence signal data collected for replicate features on a 5-mer peptide array labeled by MTG in the presence of a biotinylated amine-donor substrate. Each dot represents one of 2.8 million peptide features from a library of 1.4 million unique peptide features synthesized in duplicate. Areas of low and high signal are indicated by circles in the lower left and upper right areas of the plot, respectively.

As discussed above, in various situations it may be useful to elucidate details of enzyme activity and specificity to provide both a basic understanding of those enzymes, as well as for the development of biotechnological applications including those enzymes. For example, transglutaminases are a class of enzymes responsible for catalyzing cross-linking reactions between peptide chains. The reaction typically joins the carboxamide group of a glutamine residue with the amino group of a lysine residue. Accordingly, transglutaminases are often relied upon for site-specific labeling of proteins in a variety of biotechnological applications. However, identifying substrates for use with transglutaminases, or other enzymes in general, is limited by a lack of high-throughput and sensitive systems and methods. In one aspect, phage display systems may suffer from propagation of phages that exhibit non-specific binding to selection targets. In another aspect, a drawback of mRNA display systems is that the presence of the covalently attached mRNA may obscure interactions between the enzyme and the associated peptide sequence. Moreover, the diversity of possible peptide sequences (e.g., >$10^6$ sequences for a 5-mer peptide) makes finding common substrate motifs difficult. Further challenges may arise depending on the method selected for peptide synthesis, the size or complexity of the synthesized peptide features, the nature of the interaction between the enzyme and peptide sequence, the like, and combinations thereof.

These and other challenges may be overcome with a system and method for the identification of transglutaminase substrates. In one embodiment, an assay was developed and optimized to measure the ability of microbial transglutaminase from *Streptomyces mobaraensis* (MTG) to label peptides on an array having greater than one million unique features synthesized using maskless light-directed synthesis. The optimized assay was capable of identifying specific peptide sequence motifs where MTG exhibited a high degree of labeling activity and specificity. Results indicating labeling of peptides by MTG on array were further validated using standard biochemical assays for measuring enzyme activity in vitro. Accordingly, a system and method for the identification of MTG substrates was developed that can be expanded to the identification of substrates associated with alternative transglutaminases and for other enzymes, in general.

II. Detailed Description

Several embodiments of the invention are described in the Summary section of this patent application and each of the embodiments described in this Detailed Description section of the application applies to the embodiments described in the Summary, including the embodiments described by the enumerated clauses. In any of the various embodiments described herein, the following features may be present where applicable, providing additional embodiments of the invention. For all of the embodiments, any applicable combination of embodiments is also contemplated.

In one embodiment, an isolated peptide comprising a sequence motif of GDYALQGPG (SEQ ID NO: 79) is provided. In this embodiment, the isolated peptide can comprise a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof. In this embodiment, the peptide comprises the sequence DYALQ (SEQ ID NO: 1).

In another embodiment, an isolated peptide is provided that can comprise a sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), or a combination thereof. In another embodiment, the peptide comprises the sequence GGGDYALQGGG (SEQ ID NO: 26). In yet another embodiment, the peptide can comprise the sequence DYALQ (SEQ ID NO: 1).

In another embodiment, a protein comprising a heterologous transglutaminase substrate peptide sequence comprising a sequence motif of [YF][VA]LQG is provided. The use of brackets in peptide sequences disclosed herein indicates a sequence or sequence motif having one or more alternative amino acids at a given position within the peptide sequence. For example, the sequence motif of [YF][VA]LQG can have either of the amino acids Y and F in the first position of the peptide sequence, and either of the amino acids V and A in the second position of the peptide sequence, thereby resulting in four possible unique peptide sequences (i.e., YVLQG, YALQG, FVLQG, and FALQG).

In the embodiment comprising the sequence motif of [YF][VA]LQG, the protein can comprise a heterologous transglutaminase substrate peptide comprising a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In still another illustrative aspect, a protein is provided comprising a heterologous transglutaminase substrate peptide sequence comprising a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), and NFVLQ (SEQ ID NO:25), or a combination thereof.

In yet another embodiment, a protein comprising a heterologous transglutaminase substrate peptide comprising a sequence motif of SK[LS]K or [KR][ST]KL is provided. In this embodiment, the heterologous transglutaminase substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), FTKSK (SEQ ID NO:64), RLKSK (SEQ ID NO:67), KLGAK (SEQ ID NO:72), QRSKL (SEQ ID NO:73), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof.

In another illustrative embodiment, a protein is provided comprising a heterologous transglutaminase substrate peptide sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In yet another illustrative embodiment, a protein comprising a heterologous transglutaminase substrate peptide sequence comprising a sequence motif of GDYALQGPG (SEQ ID NO: 79) is provided. In this illustrative aspect, the heterologous transglutaminase substrate peptide can comprise a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In another illustrative embodiment, a protein comprising a heterologous transglutaminase glutamine substrate peptide sequence is provided. In this illustrative aspect, the heterologous transglutaminase substrate peptide can comprise a sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), and GGGDYALQGGGG (SEQ ID NO: 86), or a combination thereof.

As used herein "heterologous" in reference to a peptide means a transglutaminase substrate peptide that originates from a different protein than the protein into which it is incorporated (e.g., a transglutaminase substrate peptide incorporated into a Vitamin D binding protein).

In yet other embodiments, the transglutaminase substrate peptide described herein can have a glutamine residue in the fifth position. In still another embodiment, the peptide described herein can be a transglutaminase glutamine substrate peptide or a transglutaminase lysine substrate peptide.

In yet another embodiment, the transglutaminase substrate peptide can comprise a sequence of DYALQ (SEQ ID NO: 1) or can have a sequence motif comprising [FY][FYT]LQ, [YF]VAQ, K[YLS]K, or TKL.

In one illustrative embodiment, the peptide can be a peptide substrate for a transglutaminase. In another embodiment, the peptide can be a peptide substrate for a microbial transglutaminase (e.g., a *Streptoverticillium* sp. transglutaminase) or a mammalian transglutaminase. In the embodiment where the enzyme is a mammalian transglutaminase, the mammalian transglutaminase can be, for example, selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

In one embodiment, the invention encompasses isolated or substantially purified peptides or proteins. An "isolated"

peptide or protein is substantially free of chemical precursors or other chemicals when chemically synthesized (i.e., a synthetic peptide), or is substantially free of cellular material if made by recombinant DNA techniques.

In another embodiment, the peptides or proteins described herein can be "purified." In one embodiment, the purified peptides or proteins described herein can have a purity of at least about 90%, or about 95%, or about 96%, or about 97%, or about 98%, or about 99%, or about 99.5%. In another embodiment, the purified peptides or proteins described herein can have a purity of at least 90%, or at least 95%, or at least 96%, or at least 97%, or at least 98%, or at least 99%, or at least 99.5%. The purity of the peptide or protein may be measured using any conventional techniques, including various chromatography or spectroscopic techniques, such as high pressure or high performance liquid chromatography, nuclear magnetic resonance spectroscopy, thin layer chromatography (TLC), ultraviolet (UV) absorbance spectroscopy, fluorescence spectroscopy, and the like.

As used herein, purity determinations may be based on weight percentage, mole percentage, and the like. In addition, purity determinations may be based on the absence or substantial absence of certain predetermined components. It is also to be understood that purity determinations are applicable to solutions of the peptides or proteins prepared by the methods described herein. In those instances, purity measurements, including weight percentage and mole percentage measurements, are related to the components of the solution exclusive of the solvent.

In another embodiment, the peptide, protein, or compound described herein is provided in a sterile container (e.g., a vial) or package, for example, an ampoule or a sealed vial. In various embodiments described herein, the peptides and proteins described herein may be modified by substitution, deletion, truncation, elongation, and/or can be fused with other peptide or protein molecules. The peptides or proteins described herein can also be linked to a compound (e.g., a small organic molecule) for cross-linking of the compound to another peptide or protein using a transglutaminase. In one embodiment for the peptides modified by substitution, the amino acids in the peptides can each be substituted with any of the 19 other natural amino acids or with any suitable unnatural amino acid. In another embodiment, the peptides described herein can comprise natural or unnatural amino acids.

The term "natural amino acid" or "canonical amino acid" refers to one of the twenty amino acids typically found in proteins and used for protein biosynthesis as well as other amino acids which can be incorporated into proteins during translation (including pyrrolysine and selenocysteine). The twenty natural amino acids include the L-stereoisomers of histidine (His; H), alanine (Ala; A), valine (Val; V), glycine (Gly; G), leucine (Leu; L), isoleucine (Ile; I), aspartic acid (Asp; D), glutamic acid (Glu; E), serine (Ser; S), glutamine (Gln; Q), asparagine (Asn; N), threonine (Thr; T), arginine (Arg; R), proline (Pro; P), phenylalanine (Phe; F), tyrosine (Tyr; Y), tryptophan (Trp; W), cysteine (Cys; C), methionine (Met; M), and lysine (Lys; K). The term "all twenty amino acids" refers to the twenty natural amino acids listed above.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-stereoisomers of all twenty amino acids, the beta-amino-analogs of all twenty amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

In various illustrative aspects, the peptides described herein can be peptides of about 5 to about 19 amino acids, about 5 to about 18 amino acids, about 5 to about 17 amino acids, about 5 to about 16 amino acids, about 5 to about 15 amino acids, about 5 to about 14 amino acids, about 5 to about 13 amino acids, about 5 to about 12 amino acids, about 5 to about 11 amino acids, about 5 to about 10 amino acids, about 5 to about 9, about 5 to about 8, about 5 to about 7, or about 5 to about 6 amino acids. In other illustrative aspects, the peptides described herein can be peptides of 5 to 19 amino acids, 5 to 18 amino acids, 5 to 17 amino acids, 5 to 16 amino acids, 5 to 15 amino acids, 5 to 14 amino acids, 5 to 13 amino acids, 5 to 12 amino acids, 5 to 11 amino acids, 5 to 10 amino acids, 5 to 9 amino acids, 5 to 8 amino acids, 5 to 7 amino acids, or 5 to 6 amino acids. In yet another illustrative embodiment, the peptides can be selected from the group consisting of 5-mers, 6-mers, 7-mers, 8-mers, 9-mers, 10-mers, 11-mers, 12-mers, 13-mers, 14-mers, 15-mers, 16-mers, 17-mers, 18-mers, or 19-mers, or a combination thereof.

In another embodiment, the peptides described herein can be synthetic. In various embodiments, the peptides described herein can comprise or consist of an amino acid sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another embodiment, a peptide described herein can have "a" sequence consisting of, or can have "the" sequence consisting of, an amino acid sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or combinations thereof.

In yet another embodiment a peptide described herein can comprise, consist of, have a, or have the sequence motif of GDYALQGPG (SEQ ID NO: 79), [YF][VA]LQG, SK[LS]K, [KR][ST]KL, or a combination thereof.

In another embodiment, peptides or proteins are provided having about 60%, about 70%, about 75%, about 80%, about 85%, about 90%, about 95%, about 96%, about 97%, about 98%, or about 99% homology with any of SEQ ID NOS: 1 to 93. Determination of percent identity or similarity between sequences can be done, for example, by using the GAP program (Genetics Computer Group, software; available from Accelrys), and alignments can be done using, for example, the ClustalW algorithm (Vector NTI software, InforMax Inc.). A sequence database can be searched using the peptide sequence of interest. Algorithms for database searching are typically based on the Basic Local Alignment Search Tool (BLAST) software (Altschul et al., 1990).

In another embodiment, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts as the side chain of the amino acid which has been replaced.

In one illustrative aspect, non-conservative substitutions are possible provided that these do not excessively affect the activity of the peptide. As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. An exemplary list of illustrative conservative amino acid substitutions is given in Table 1.

TABLE 1

| For Amino Acid | Replace With |
| --- | --- |
| Alanine | D-Ala, Gly, α-aminobutyric acid (Aib), β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In yet another aspect, the peptides described herein (e.g., SEQ ID NOS: 1 to 93) are substrates of a transglutaminase and are capable of binding or specifically binding to a transglutaminase. As used herein "specifically binding" or "specific binding" means binding of a receptor (e.g., a substrate) to a labeled ligand (e.g., an enzyme) that is not displaceable by an excess of unlabeled ligand in a specific binding assay utilizing labeled ligand and unlabeled ligand.

In various embodiments, where transglutaminase substrates are identified based on a predetermined property, binding, specific binding or enzyme activity can be, for example, a predetermined property.

In one embodiment, the peptides described herein can be synthesized according to solid phase peptide synthesis protocols that are well known by persons of skill in the art. In one such embodiment, a peptide precursor is synthesized on a solid support according to the well-known Fmoc protocol, cleaved from the support with trifluoroacetic acid, and purified by chromatography according to methods known to persons skilled in the art. Techniques for synthesizing the peptides described herein, such as SEQ ID NOS: 1 to 93, or fragments thereof, are described in Sambrook et al., "Molecular Cloning: A Laboratory Manual", 3rd Edition, Cold Spring Harbor Laboratory Press, (2001), incorporated herein by reference. Peptides for use in the methods described herein can also be made commercially.

In another embodiment, the peptides or proteins described herein can be synthesized utilizing the methods of biotechnology that are well known to persons skilled in the art. In one such embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan. Methods described in Sambrook et al. can also be used to incorporate the peptide sequences described herein into the proteins described herein based on well-known molecular cloning techniques. In another embodiment, the peptides described herein may be synthesized using a ribosomal translation system. The proteins described herein, incorporating heterologous peptide sequences, can also be made by such recombinant DNA techniques.

Techniques for purifying or isolating the peptides described herein are also well-known in the art. Such techniques are also described in Sambrook et al., "Molecular Cloning: A Laboratory Manual", 3rd Edition, Cold Spring Harbor Laboratory Press, (2001), incorporated herein by reference.

In another embodiment, a method is provided of identifying a substrate of a transglutaminase using a peptide array comprising a plurality of peptides. The method comprises the steps of contacting the peptides in the peptide array with the transglutaminase, allowing the transglutaminase to bind to the peptides, and identifying the substrate of the transglutaminase.

In another illustrative aspect, a method is provided of identifying a substrate of a transglutaminase using one or more peptide arrays comprising a plurality of peptides. The method comprises the steps of contacting the peptides in a first peptide array with the transglutaminase, allowing the transglutaminase to bind to the peptides in the first peptide array, selecting one or more of the peptides in the first peptide array that exhibit a predetermined property upon binding to the transglutaminase, synthesizing variants of the one or more peptides that are identified in the first peptide array, contacting the variant peptides in a second peptide array with the transglutaminase, and selecting one or more of the variant peptides that are identified in the second peptide array as exhibiting the predetermined property upon binding to the transglutaminase.

In yet another embodiment, a peptide array is provided comprising a solid support and a plurality of peptides, wherein the peptides are transglutaminase substrate peptides, and wherein the peptide array is made by maskless light-directed peptide array synthesis.

In one embodiment, the peptides on the peptide array for use in the identification methods and peptide array described herein are transglutaminase substrate peptides. In one illustrative embodiment, the enzyme substrate peptides can be substrate peptides for a microbial transglutaminase (e.g., a *Streptoverticillium* sp. transglutaminase such as *Streptoverticillium mobaraense* or a transglutaminase from another bacterial species) or a mammalian transglutaminase. In the embodiment where the peptides are substrate peptides for a mammalian transglutaminase, the mammalian transglutaminase can be, for example, selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

In yet another embodiment where the peptide is a transglutaminase substrate peptide, the peptide can be a transglutaminase glutamine substrate peptide. In another embodiment where the peptide is a transglutaminase substrate peptide, the peptide can be a transglutaminase lysine substrate peptide. In another aspect, transglutaminase substrate peptides for use in the identification methods and peptide arrays described herein can have a sequence motif of GDYALQGPG (SEQ ID NO: 79), [YF][VA]LQG, SK[LS]K, or [KR][ST]KL. In the embodiment where the substrate peptide is a transglutaminase glutamine substrate peptide, the peptide can have a glutamine residue in the fifth position.

In various embodiments described herein, the peptides for use in the peptide arrays described herein may be modified by substitution, deletion, truncation, elongation, and/or can be fused with or attached to other peptide molecules wherein the modified peptides are useful in the methods and peptide arrays described herein. In one embodiment for the peptides modified by substitution, the amino acids in the peptides can each be substituted with any of the 19 other natural amino acids or with any suitable unnatural amino acid. In another embodiment, the peptides described herein can comprise natural or unnatural amino acids.

In various illustrative aspects, the peptides for use in the peptide arrays described herein can comprise peptides of about 5 to about 19 amino acids, about 5 to about 18 amino acids, about 5 to about 17 amino acids, about 5 to about 16 amino acids, about 5 to about 15 amino acids, about 5 to about 14 amino acids, about 5 to about 13 amino acids, about 5 to about 12 amino acids, about 5 to about 11 amino acids, about 5 to about 10 amino acids, about 5 to about 9, about 5 to about 8, about 5 to about 7, or about 5 to about 6 amino acids. In other illustrative aspects, the peptides described herein can comprise peptides of 5 to 19 amino acids, 5 to 18 amino acids, 5 to 17 amino acids, 5 to 16 amino acids, 5 to 15 amino acids, 5 to 14 amino acids, 5 to 13 amino acids, 5 to 12 amino acids, 5 to 11 amino acids, 5 to 10 amino acids, 5 to 9 amino acids, 5 to 8 amino acids, 5 to 7 amino acids, or 5 to 6 amino acids. In yet another illustrative embodiment, the peptides can be selected from the group consisting of 5-mers, 6-mers, 7-mers, 8-mers, 9-mers, 10-mers, 11-mers, 12-mers, 13-mers, 14-mers, 15-mers, 16-mers, 17-mers, 18-mers, or 19-mers or a combination thereof.

In another embodiment, the peptides for use in the peptide arrays described herein can be synthetic. In various embodiments, the peptides for use in the methods and peptide arrays described herein can have the, comprise, consist of, or have an amino acid sequence selected from SEQ ID NO:1 to SEQ ID NO: 93, or a combination thereof. In another embodiment, peptides having about 60%, about 70%, about 75%, about 80%, about 85%, about 90%, about 95%, about 96%, about 97%, about 98%, or about 99% homology with any of SEQ ID NOS: 1 to 93 can be used in the peptide arrays described herein.

In yet another aspect, the peptides for use in the peptide arrays described herein are transglutaminase substrates and are capable of binding or specifically binding to a transglutaminase. As used herein "specifically binding" or "specific binding" means binding of a receptor (e.g., a substrate) to a labeled ligand (e.g., an enzyme) that is not displaceable by an excess of unlabeled ligand in a specific binding assay utilizing labeled ligand and unlabeled ligand. In various embodiments, where transglutaminase substrates are identified based on a predetermined property, binding, specific binding or enzyme activity can be, for example, a predetermined property.

In one aspect, the peptides and peptide arrays described herein can be synthesized as described in Example 12. Any appropriate protocols for synthesizing peptides for use on peptide arrays that are well-known by persons of skill in the art can also be used.

In various embodiments, the peptide arrays described herein can have at least $1.6 \times 10^5$ peptides, at least $2.0 \times 10^5$ peptides, at least $3.0 \times 10^5$ peptides, at least $4.0 \times 10^5$ peptides, at least $5.0 \times 10^5$ peptides, at least $6.0 \times 10^5$ peptides, at least $7.0 \times 10^5$ peptides, at least $8.0 \times 10^5$ peptides, at least $9.0 \times 10^5$ peptides, at least $1.0 \times 10^6$ peptides, at least $1.2 \times 10^6$ peptides, at least $1.4 \times 10^6$ peptides, at least $1.6 \times 10^6$ peptides, at least $1.8 \times 10^6$ peptides, at least $1.0 \times 10^7$ peptides, or at least $1.0 \times 10^8$ peptides attached to the solid support of the peptide array. In other embodiments, the peptide arrays described herein can have about $1.6 \times 10^5$ peptides, about $2.0 \times 10^5$ peptides, about $3.0 \times 10^5$ peptides, about $4.0 \times 10^5$ peptides, about $5.0 \times 10^5$ peptides, about $6.0 \times 10^5$ peptides, about $7.0 \times 10^5$ peptides, about $8.0 \times 10^5$ peptides, about $9.0 \times 10^5$ peptides, about $1.0 \times 10^6$ peptides, about $1.2 \times 10^6$ peptides, about $1.4 \times 10^6$ peptides, about $1.6 \times 10^6$ peptides, about $1.8 \times 10^6$ peptides, about $1.0 \times 10^7$ peptides, or about $1.0 \times 10^8$ peptides attached to the solid support of the peptide array. As described herein, a peptide array comprising a particular number of peptides can mean a single peptide array on a single solid support, or the peptides can be divided and attached to more than one solid support to obtain the number of peptides described herein.

In various embodiments, the peptides attached to the peptide arrays can lack cysteine, can lack amino acid repeats, can be unique (i.e., each peptide is different from the other peptides on the array), and/or can represent all transglutaminase substrates with a length selected from the group consisting of 5-mers, 6-mers, 7-mers, 8-mers, 9-mers, 10-mers, 11-mers, and 12-mers, or a combination thereof.

As described herein, a "peptide array" means an intentionally created collection of peptides that can be prepared synthetically. In one embodiment, the peptides in the array can be different from each other. Methods for synthesizing peptide arrays, including peptide arrays made by maskless light-directed peptide array synthesis, are known in the art and exemplary methods are described in U.S. Patent Appl. Publication Nos. 2004/0023367 and 2009/0176664 and U.S. Pat. Nos. 6,375,903 and 5,143,854. Additional methods are described in Example 12 herein.

In one embodiment, the peptides in the peptide array are attached to a solid support. A solid support refers to a material or materials having a rigid or semi-rigid surface or surfaces. In some aspects, at least one surface of the solid support will be substantially flat, although in some aspects regions may be physically separated for different peptides with, for example, wells, raised regions, pins, etched trenches, or the like.

In various embodiments, support materials may include, for example, silicon, bio-compatible polymers such as, for example poly(methyl methacrylate) (PMMA) and polydimethylsiloxane (PDMS), glass, plastic, SiO2, quartz, silicon nitride, functionalized glass, gold, platinum, carbon composite, or aluminum. Functionalized surfaces include for example, amino-functionalized glass, carboxy-functionalized glass, and hydroxyl-functionalized glass. Additionally, a support may optionally be coated with one or more layers to provide a surface for molecular attachment or functionalization, increased or decreased reactivity, binding detection, and the like. The appropriate support material can be selected by a person skilled in the art.

In one embodiment, the peptide array can be made using maskless light-directed peptide array synthesis. Maskless light-directed peptide array synthesis may utilize micromirrors and projection optics which focus an image of the micromirrors on the support where the reactions are conducted. In one embodiment, under the control of a computer, each of the micromirrors is selectively switched between a first position at which it projects light on the substrate through the optical system and a second position at which it deflects light away from the substrate. In this embodiment, the individually controllable mirrors can steer light beams to produce images or light patterns. In one embodiment, reactions at different regions on the solid support can be modulated by providing irradiation of different strengths using a micromirror device. Such devices are available commercially. In one aspect, the controlled light irradiation allows control of the reactions to proceed at a desirable rate. In one embodiment, the peptides are attached covalently to the solid support. In another embodiment, the peptides are attached non-covalently to the solid support. In yet another embodiment, the peptides are attached to the solid support by a linker, such as a cleavable linker. In one illustrative embodiment, the linker is about 4 to about 40 atoms long. Exemplary linkers are aryl acetylene, ethylene glycol oligomers containing 2-10 monomer units (PEGs), diamines, diacids, amino acids, and the like, and combinations thereof. A person skilled in the art will know how to design appropriate linkers.

In one embodiment, the peptide attached to the peptide array or the peptide identified using the peptide array may comprise a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), and NFVLQ (SEQ ID NO:25), or a combination thereof.

In another illustrative embodiment, the peptide attached to the peptide array or the peptide identified using the peptide array may comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In yet another embodiment, the peptide attached to the peptide array or the peptide identified using the peptide array may comprise a sequence selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), or a combination thereof.

In yet other embodiments, the peptide attached to the peptide array or the peptide identified using the peptide array may have a sequence comprising GGGDYALQGGG (SEQ ID NO: 26) or DYALQ (SEQ ID NO:1). In yet another embodiment, the transglutaminase substrate peptide attached to the peptide array can have a glutamine in the fifth position or can have a sequence motif comprising [FY][FYT]LQ, [YF]VAQ, K[YLS]K, or TKL.

In yet other embodiments, methods for cross-linking peptides, proteins, or compounds, or a combination thereof, are provided. In the cross-linking embodiments described herein, the terms "cross-link" and "cross-linking" mean allowing a glutamine substrate peptide of a transglutaminase and a lysine substrate of a transglutaminase to come in contact with a transglutaminase under appropriate reaction conditions whereby the transglutaminase catalyzes the formation of an isopeptide bond between a gamma-carboxamide group of a glutamine residue and an epsilon-amino group of a lysine residue of the transglutaminase substrate peptides. In various embodiments, the cross-linking can occur when the peptide is already incorporated into a protein or a compound, or when the peptide has not been incorporated into a protein or a compound.

In one embodiment of the method for crossing-linking, a method for cross-linking a protein is provided. The method comprises the steps of incorporating at least one heterologous transglutaminase substrate peptide sequence into the protein, and cross-linking the protein by contacting the protein with a transglutaminase wherein the heterologous transglutaminase peptide sequence comprises a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In another cross-linking embodiment, a method for crossing-linking a protein is provided. The method comprises the steps of incorporating at least one heterologous transglutaminase substrate peptide sequence into the protein, and cross-linking the protein by contacting the protein with a transglutaminase wherein the heterologous transglutaminase peptide sequence comprises a sequence motif selected from the group consisting of SK[LS]K, [KR][ST]KL, [YF][VA]LQG, and GDYALQGPG (SEQ ID NO: 79), or a combination thereof. In this embodiment, the heterologous transglutaminase substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), FTKSK (SEQ ID NO:64), RLKSK (SEQ ID NO:67), KLGAK (SEQ ID NO:72), QRSKL (SEQ ID NO:73), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof. In another aspect, the heterologous transglutaminase substrate peptide can comprise a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof.

In yet another embodiment, the heterologous transglutaminase substrate peptide can comprise a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In these cross-linking embodiments, the heterologous transglutaminase peptide sequence can comprise the sequence DYALQ (SEQ ID NO: 1) or the sequence GGGDYALQGGG (SEQ ID NO: 26). In yet another embodiment, the transglutaminase substrate peptide can have a glutamine in the fifth position or can have a sequence motif comprising [FY][FYT]LQ, [YF]VAQ, K[YLS]K, or TKL.

As used herein "heterologous" in reference to a peptide means a transglutaminase substrate peptide that originates from a different protein than the protein into which it is incorporated (e.g., a transglutaminase substrate peptide incorporated into a Vitamin D binding protein).

In these cross-linking embodiments, the peptides of SEQ ID NOS: 1 to 93 can be incorporated into the protein by well-known molecular cloning techniques described, for example, in Sambrook et al., "Molecular Cloning: A Laboratory Manual", 3rd Edition, Cold Spring Harbor Laboratory Press, (2001), incorporated herein by reference. In various embodiments, the cross-link may occur internally in one protein or between two different proteins (i.e., separate proteins of the same or different types) or between the protein and a peptide (e.g., a peptide incorporated into a label, affinity tag, moiety for PEGylation, and the like). In this embodiment, "incorporated into" means incorporating both ends of a peptide comprising SEQ ID NOS: 1 to 93 internally into the protein or attaching one end of a peptide comprising SEQ ID NOS: 1 to 93 to an internal sequence of the protein or to the N-terminus or C-terminus of a protein or peptide. In another embodiment, the peptide flanked at either or both ends of the peptide by an affinity tag can be incorporated. In one aspect, the peptides described may be modified by substitution, deletion, truncation, elongation, and/or can be fused with or attached to other peptide molecules wherein the modified peptides are useful in this method embodiment. In one embodiment for the peptides modified by substitution, the amino acids in the peptides can each be substituted with any of the 19 other natural amino acids or with any suitable unnatural amino acid. In another embodiment, the peptides described herein can comprise natural or unnatural amino acids. In various embodiments, the peptides for use in these cross-linking embodiments can have about 60%, about 70%, about 75%, about 80%, about 85%, about 90%, about 95%, about 96%, about 97%, about 98%, or about 99% homology with any of the peptides of SEQ ID NOS: 1 to 93. In various illustrative aspects, the peptides for use in these cross-linking embodiments can be modified by making conservative substitutions as described herein or by altering the length of the peptides to comprise peptides of about 5 to about 19 amino acids, about 5 to about 18 amino acids, about 5 to about 17 amino acids, about 5 to about 16 amino acids, about 5 to about 15 amino acids, about 5 to about 14 amino acids, about 5 to about 13 amino acids, about 5 to about 12 amino acids, about 5 to about 11 amino acids, about 5 to about 10 amino acids, about 5 to about 9, about 5 to about 8, about 5 to about 7, or about 5 to about 6 amino acids. In other illustrative aspects, the peptides can comprise peptides of 5 to 19 amino acids, 5 to 18 amino acids, 5 to 17 amino acids, 5 to 16 amino acids, 5 to 15 amino acids, 5 to 14 amino acids, 5 to 13 amino acids, 5 to 12 amino acids, 5 to 11 amino acids, 5 to 10 amino acids, 5 to 9 amino acids, 5 to 8 amino acids, 5 to 7 amino acids, or 5 to 6 amino acids. In yet another illustrative embodiment, the peptides can be selected from the group consisting of 5-mers, 6-mers, 7-mers, 8-mers, 9-mers, 10-mers, 11-mers, 12-mers, 13-mers, 14-mers, 15-mers, 16-mers, 17-mers, 18-mers, or 19-mers or a combination thereof.

In another cross-linking embodiment, a method for cross-linking at least two compounds is provided. The method comprises the steps of incorporating a heterologous transglutaminase glutamine substrate peptide with a sequence motif of [YF][VA]LQG or GDYALQGPG (SEQ ID NO: 79) into one of the at least two compounds, and cross-linking the compounds by contacting the compounds with a transglutaminase. The method can further comprise the step of incorporating into the other compound a heterologous transglutaminase lysine substrate peptide comprising a sequence motif of SK[LS]K or [KR][ST]KL. In this embodiment, the heterologous transglutaminase lysine substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), FTKSK (SEQ ID NO:64), RLKSK (SEQ ID NO:67), KLGAK (SEQ ID NO:72), QRSKL (SEQ ID NO:73), LSKLK (SEQ ID NO:75), NRTKL (SEQ ID NO:76), QRTKL (SEQ ID NO:77), GGGRSKLAGGG (SEQ ID NO:

82), and GGGARSKLGGGG (SEQ ID NO: 80), or a combination thereof. In this embodiment, the heterologous transglutaminase glutamine substrate peptide can comprise a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), and NFVLQ (SEQ ID NO:25), or a combination thereof. In another aspect of this embodiment, the heterologous transglutaminase glutamine substrate peptide can comprise a sequence selected from the group consisting of CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof.

In yet another embodiment, a method for cross-linking at least two compounds is provided. The method comprises the steps of incorporating a heterologous transglutaminase glutamine substrate peptide comprising a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), and GGGDYALQGGGG (SEQ ID NO: 86), or a combination thereof, into one of the at least two compounds, and cross-linking the compounds by contacting the compounds with a transglutaminase.

In this method embodiment, the method can further comprise the step of incorporating a heterologous transglutaminase lysine substrate peptide into the other of the at least two compounds. The lysine substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In these cross-linking embodiments, the compounds can be selected from the group consisting of a protein, a peptide, and a small organic molecule (e.g., a label, an affinity tag, etc.), or a combination thereof. In any of these embodiments, the glutamine substrate peptide can have a sequence comprising DYALQ (SEQ ID NO: 1). In yet another embodiment, the transglutaminase substrate peptide can have a glutamine at the fifth position or can have a sequence motif comprising [FY][FYT]LQ, [YF]VAQ, K[YLS]K, or TKL. In one embodiment, the compounds can both be peptides and at least one of the peptides can be attached to a solid support, such as in a peptide array.

In one embodiment, the labels for use in any appropriate embodiment herein can comprise fluorescein, rhodamine, Texas Red, phycoerythrin, Oregon Green (e.g., Oregon Green 488, Oregon Green 514, and the like) AlexaFluor 488, AlexaFlour 647 (Molecular Probes, Eugene, Oreg.), Cy3, Cy5, Cy7, biotin, ruthenium, DyLight fluorescent agents, including but not limited to DyLight 680, CW 800, trans-cyclooctene, tetrazine, methyltetrazine, and the like.

As used in these additional illustrative cross-linking embodiments, "heterologous" in reference to a peptide means a transglutaminase substrate peptide that originates from a different protein than the protein into which it is incorporated (e.g., a transglutaminase substrate peptide incorporated into a Vitamin D binding protein).

In these additional cross-linking embodiments, the peptides of SEQ ID NOS: 1 to 93 or of the motifs of [YF][VA]LQG, GDYALQGPG (SEQ ID NO: 79), SK[LS]K, or [KR][ST]KL can be incorporated into the compound (e.g., a protein) by well-known molecular cloning techniques described, for example, in Sambrook et al., "Molecular Cloning: A Laboratory Manual", 3rd Edition, Cold Spring Harbor Laboratory Press, (2001), incorporated herein by reference. In one embodiment, the cross-link may occur between two different proteins (i.e., separate proteins of the same or different type). In this embodiment, "incorporated into" means incorporating both ends of a peptide comprising SEQ ID NOS: 1 to 93 internally into a protein sequence or attaching one end of a peptide comprising SEQ ID NOS: 1 to 93 to an internal sequence of a protein or to the N-terminus or C-terminus of a protein. The peptides described herein can be linked to the compound (e.g., a label or an affinity tag) by linking chemistry well-known to the skilled artisan.

In one aspect, the peptides described for use in these additional cross-linking embodiments may be modified by substitution, deletion, truncation, elongation, and/or can be fused with or attached to other peptide molecules wherein the modified peptides are useful in this method embodiment. In one embodiment for the peptides modified by substitution, the amino acids in the peptides can each be substituted with any of the 19 other natural amino acids or with any suitable unnatural amino acid. In another embodiment, the peptides described herein can comprise natural or unnatural amino acids. In various embodiments, the peptides for use in this method embodiment can have about 60%, about 70%, about 75%, about 80%, about 85%, about 90%, about 95%, about 96%, about 97%, about 98%, or about 99% homology with any of SEQ ID NOS: 1 to 93.

In various illustrative aspects, the peptides for use in these additional cross-linking embodiments can be modified by making conservative substitutions as described herein or by altering the length of the peptides to comprise peptides of about 5 to about 19 amino acids, about 5 to about 18 amino acids, about 5 to about 17 amino acids, about 5 to about 16 amino acids, about 5 to about 15 amino acids, about 5 to about 14 amino acids, about 5 to about 13 amino acids, about 5 to about 12 amino acids, about 5 to about 11 amino acids, about 5 to about 10 amino acids, about 5 to about 9, about 5 to about 8, about 5 to about 7, or about 5 to about 6 amino acids. In other illustrative aspects, the peptides can comprise peptides of 5 to 19 amino acids, 5 to 18 amino acids, 5 to 17 amino acids, 5 to 16 amino acids, 5 to 15 amino acids, 5 to 14 amino acids, 5 to 13 amino acids, 5 to 12 amino acids, 5 to 11 amino acids, 5 to 10 amino acids, 5 to 9 amino acids, 5 to 8 amino acids, 5 to 7 amino acids, or 5 to 6 amino acids. In yet another illustrative embodiment, the peptides can be selected from the group consisting of 5-mers, 6-mers, 7-mers, 8-mers, 9-mers, 10-mers, 11-mers, 12-mers, 13-mers, 14-mers, 15-mers, 16-mers, 17-mers, 18-mers, or 19-mers or a combination thereof.

In still another embodiment, a method for cross-linking a protein internally is provided. The method comprises the steps of incorporating a heterologous transglutaminase glutamine substrate peptide with a sequence motif of [YF][VA]LQG or GDYALQGPG (SEQ ID NO: 79) into the protein, incorporating a transglutaminase lysine substrate peptide into the protein, and cross-linking the protein by contacting the protein with a transglutaminase. In this method embodiment, the lysine substrate peptide can comprise a sequence motif of SK[LS]K or [KR][ST]KL. In this embodiment, the heterologous transglutaminase lysine substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), FTKSK (SEQ ID NO:64), RLKSK (SEQ ID NO:67), KLGAK (SEQ ID NO:72), QRSKL (SEQ ID NO:73), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof. In this embodiment, the heterologous transglutaminase glutamine substrate peptide can comprise a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), NFVLQ (SEQ ID NO:25), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof. In these embodiments, the glutamine substrate peptide can comprise the sequence DYALQ (SEQ ID NO: 1). In yet another embodiment, the transglutaminase substrate peptide can comprise a glutamine at the fifth position or can have a sequence motif comprising [FY][FYT]LQ, [YF]VAQ, K[YLS]K, or TKL.

In another cross-linking embodiment, a method for cross-linking a protein internally is provided. The method comprises the steps of incorporating a heterologous transglutaminase glutamine substrate peptide wherein the peptide comprises a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), and GGGDYALQGGGG (SEQ ID NO: 86), or a combination thereof, into the protein, incorporating a transglutaminase lysine substrate peptide into the protein, and cross-linking the protein by contacting the protein with a transglutaminase. In this embodiment, the transglutaminase lysine substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In these illustrative embodiments, two transglutaminase substrate peptides can be incorporated into the same protein to form an internal cross-link. As used in these illustrative embodiments, "heterologous" in reference to a peptide means a transglutaminase substrate peptide that originates from a different protein than the protein into which it is incorporated (e.g., a transglutaminase substrate peptide incorporated into a Vitamin D binding protein).

In this internal cross-linking embodiment, the peptides of SEQ ID NOS: 1 to 93 or of the motifs of [YF][VA]LQG, GDYALQGPG (SEQ ID NO: 79), SK[LS]K, or [KR][ST]KL can be incorporated into the protein by well-known molecular cloning techniques described, for example, in Sambrook et al., "Molecular Cloning: A Laboratory Manual", 3rd Edition, Cold Spring Harbor Laboratory Press, (2001), incorporated herein by reference. In this embodiment, "incorporated into" means incorporating both ends of a peptide comprising SEQ ID NOS: 1 to 93 internally into the protein sequence or attaching one end of a peptide comprising SEQ ID NOS: 1 to 93 to an internal sequence of the protein or to the N-terminus or C-terminus of the protein. In one aspect, the peptides described for use in this method embodiment may be modified by substitution, deletion, truncation, elongation, and/or can be fused with or attached to other peptide molecules wherein the modified peptides are useful in this method embodiment. In one embodiment for the peptides modified by substitution, the amino acids in the peptides can each be substituted with any of the 19 other natural amino acids or with any suitable unnatural amino acid.

In another embodiment, the peptides described herein can comprise natural or unnatural amino acids. In various embodiments, the peptides for use in this method embodiment can have about 60%, about 70%, about 75%, about 80%, about 85%, about 90%, about 95%, about 96%, about 97%, about 98%, or about 99% homology with any of SEQ ID NOS: 1 to 93.

In various illustrative aspects, the peptides for use in this method embodiment can be modified by making conservative substitutions as described herein or by altering the length of the peptides to comprise peptides of about 5 to about 19 amino acids, about 5 to about 18 amino acids, about 5 to about 17 amino acids, about 5 to about 16 amino acids, about 5 to about 15 amino acids, about 5 to about 14 amino acids, about 5 to about 13 amino acids, about 5 to about 12 amino acids, about 5 to about 11 amino acids, about 5 to about 10 amino acids, about 5 to about 9, about 5 to about 8, about 5 to about 7, or about 5 to about 6 amino acids. In other illustrative aspects, the peptides can comprise peptides of 5 to 19 amino acids, 5 to 18 amino acids, 5 to 17 amino acids, 5 to 16 amino acids, 5 to 15 amino acids, 5 to 14 amino acids, 5 to 13 amino acids, 5 to 12 amino acids, 5 to 11 amino acids, 5 to 10 amino acids, 5 to 9 amino acids, 5 to 8 amino acids, 5 to 7 amino acids, or 5 to 6 amino acids. In yet another illustrative embodiment, the peptides can be selected from the group consisting of 5-mers, 6-mers, 7-mers, 8-mers, 9-mers, 10-mers, 11-mers, 12-mers, 13-mers, 14-mers, 15-mers, 16-mers, 17-mers, 18-mers, or 19-mers or a combination thereof.

In one aspect, for any of the above-described cross-linking embodiments, the proteins, peptides, or compounds that are cross-linked can be, for example, a targeting ligand or a drug where the method is used to conjugate the targeting ligand to the drug. In other embodiments, the cross-linking methods can be used to conjugate a protein, a peptide, or a compound to an affinity tag, to conjugate a protein, a peptide, or a compound to a label, to PEGylate a protein, a peptide or a compound, or to biotinylate or ruthenylate a protein, a peptide, or a compound, and the like. In yet another embodiment, diagnostic proteins, such as antibodies and antibody-binding proteins can be cross-linked. In another aspect, diagnostic proteins or therapeutic proteins can be cross-linked, or proteins for research can be cross-linked, such as for the site-specific conjugation of at least two proteins.

In any of the cross-linking embodiments described herein the protein or compound can be, for example, a Vitamin D binding protein (VitDBP). In one embodiment, the compound attached to the VitDBP can be any appropriate label, such as Cy5, ruthenium, or biotin. In one embodiment, the cross-linking can occur through a heterologous transglutaminase glutamine substrate peptide that is incorporated into the VitDBP wherein the peptide comprises the sequence GGGGDYALQGGGG (SEQ ID NO: 85). In another embodiment, a heterologous transglutaminase lysine substrate peptide can be incorporated into the label and can comprise the sequence RSKLG (SEQ ID NO:58).

In one aspect, the label with an incorporated heterologous transglutaminase lysine substrate peptide for use in any cross-linking embodiment described herein can be a compound of any of the following formulae:

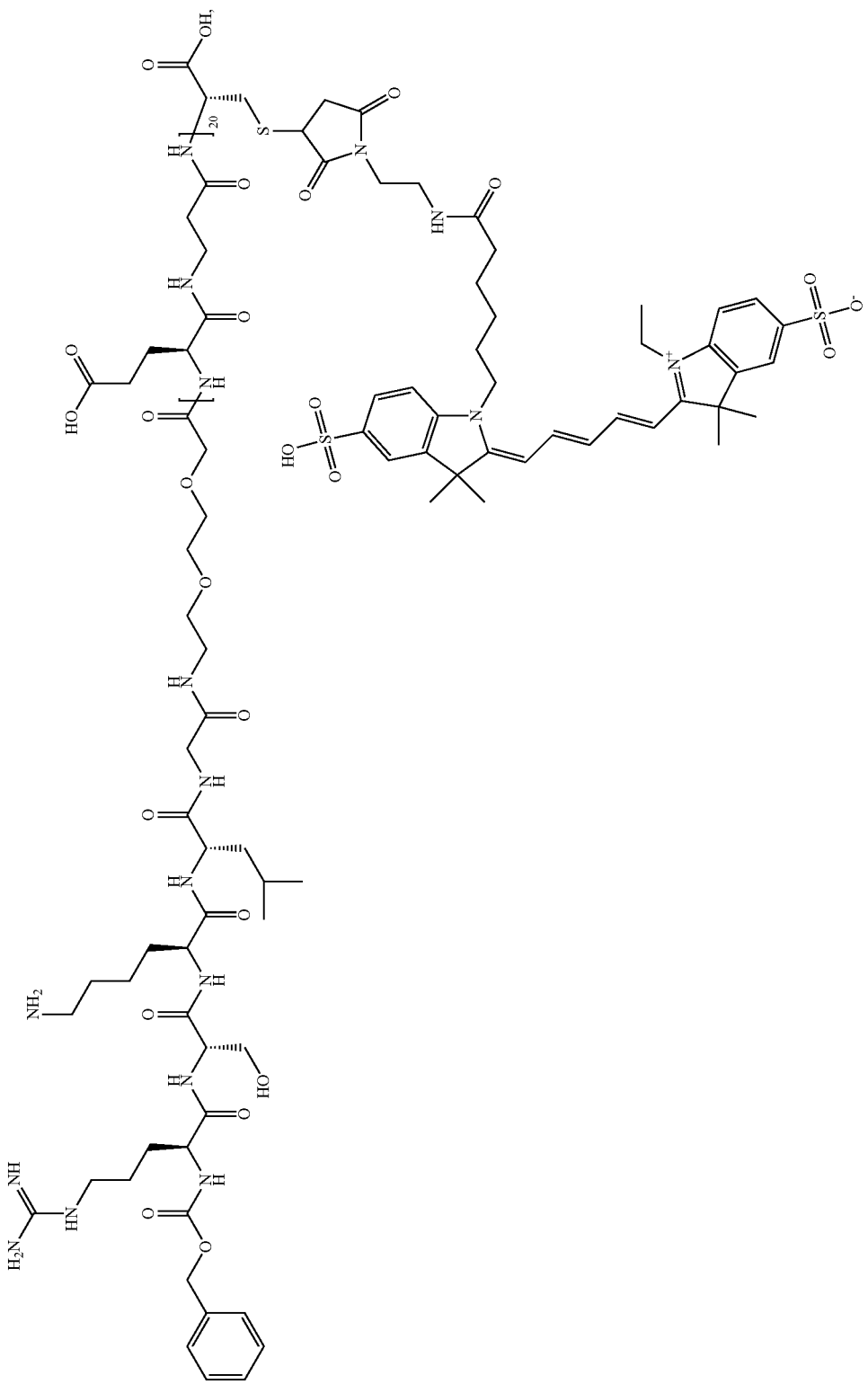

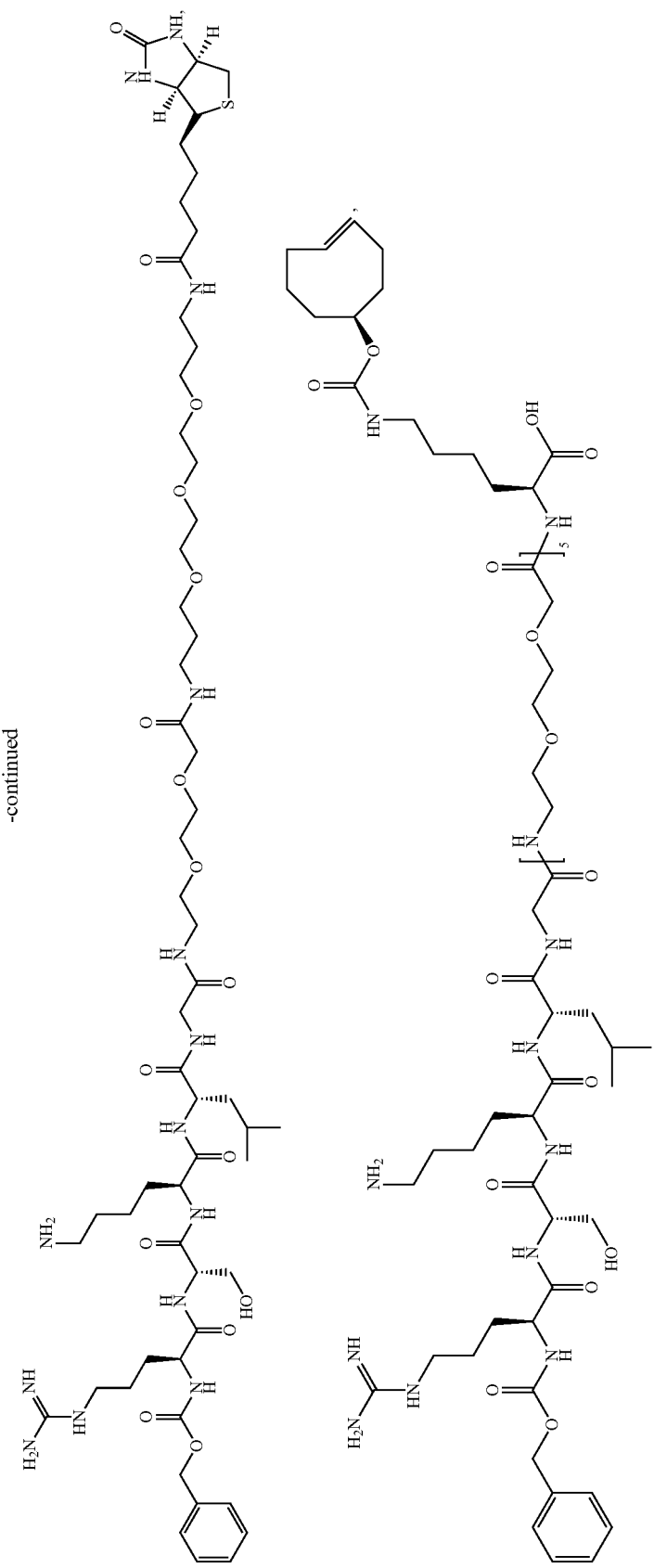

-continued
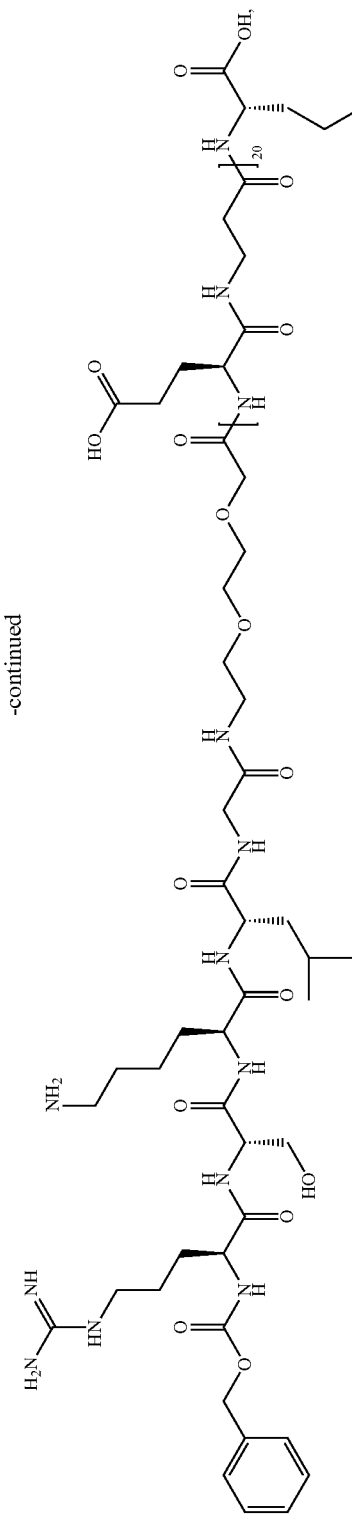

-continued
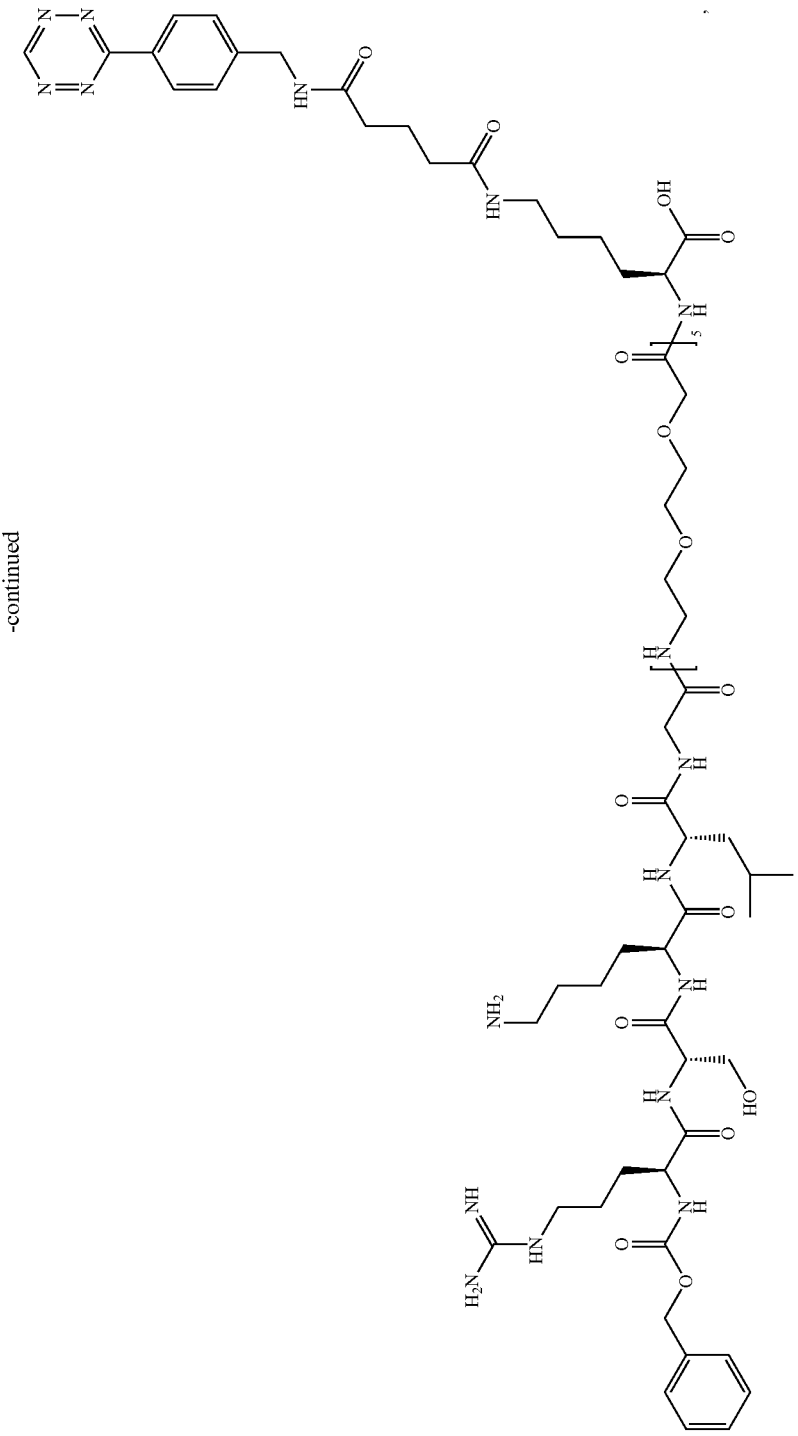

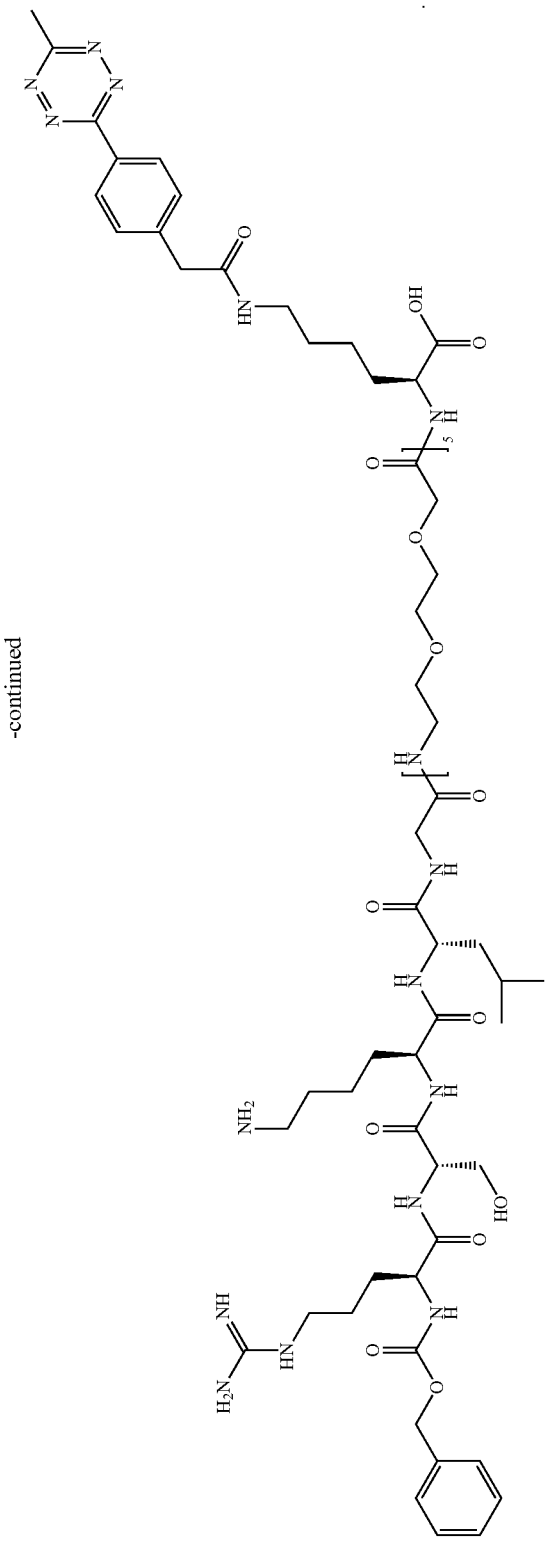

However, it will be appreciated that any suitable label can be combined with a transglutaminase substrate according to the present disclosure. Examples of suitable labels include fluorescent labels, chemilumiescent labels, radiolabels, chemical labels (e.g., incorporating "click" chemistry), the like, and combinations thereof. More generally, a suitable label is compatible with at least one substrate of the transglutaminase (e.g., lysine donor substrate, glutamine donor substrate, or the like) in that the label does not eliminate the ability of the transglutaminase to act on the substrate including the label. Further, a suitable label can produce a signal that is detectable relative to an unlabeled transglutaminase substrate.

In another illustrative embodiment, a VitDBP is described comprising a heterologous transglutaminase substrate peptide sequence. In one embodiment, the VitDBP can comprise a transglutaminase substrate peptide comprising a sequence motif selected from the group consisting of [YF][VA]LQG, GDYALQGPG (SEQ ID NO: 79), SK[LS]K, and [KR][ST]KL, or a combination thereof. In one embodiment, the heterologous transglutaminase lysine substrate peptide can comprise a sequence selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RSKSK (SEQ ID NO:62), SKSKL (SEQ ID NO:63), PKTKL (SEQ ID NO:66), RSKLA (SEQ ID NO:68), GRSKL (SEQ ID NO:69), SKLSK (SEQ ID NO:71), FTKSK (SEQ ID NO:64), RLKSK (SEQ ID NO:67), KLGAK (SEQ ID NO:72), QRSKL (SEQ ID NO:73), LSKLK (SEQ ID NO:75), NRTKL (SEQ ID NO:76), QRTKL (SEQ ID NO:77), GGGRSKLAGGG (SEQ ID NO: 82), and GGGARSKLGGGG (SEQ ID NO: 80), or a combination thereof. In one embodiment, the heterologous transglutaminase glutamine substrate peptide can comprise a sequence selected from the group consisting of DYALQ (SEQ ID NO:1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), FYALQ (SEQ ID NO:10), NYVLQ (SEQ ID NO:12), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), EFALQ (SEQ ID NO:23), NFVLQ (SEQ ID NO:25), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), and GNGDYALQGPG (SEQ ID NO: 53), or a combination thereof. In one aspect, the transglutaminase substrate peptide comprises the sequence DYALQ (SEQ ID NO: 1). In yet another embodiment, the transglutaminase substrate peptide can comprise a glutamine at the fifth position or can have a sequence motif comprising [FY][FYT]LQ, [YF]VAQ, K[YLS]K, or TKL.

In yet another embodiment, a VitDBP is described comprising a heterologous transglutaminase substrate peptide wherein the peptide comprises a sequence selected from the group consisting of DYALQ (SEQ ID NO: 1), DYVLQ (SEQ ID NO:2), NYALQ (SEQ ID NO:3), EYALQ (SEQ ID NO:4), PYALQ (SEQ ID NO:5), EYVLQ (SEQ ID NO:6), DFALQ (SEQ ID NO:7), DYFLQ (SEQ ID NO:8), NYFLQ (SEQ ID NO:9), FYALQ (SEQ ID NO:10), DYTLQ (SEQ ID NO:11), NYVLQ (SEQ ID NO:12), EYVAQ (SEQ ID NO:13), RYALQ (SEQ ID NO:14), YFALQ (SEQ ID NO:15), PYVLQ (SEQ ID NO:16), WYALQ (SEQ ID NO:17), SYALQ (SEQ ID NO:18), HYALQ (SEQ ID NO:19), DYVAQ (SEQ ID NO:20), EFVAQ (SEQ ID NO:21), DFYLQ (SEQ ID NO:22), EFALQ (SEQ ID NO:23), EYFLQ (SEQ ID NO:24), NFVLQ (SEQ ID NO:25), GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GNGDYALQGPG (SEQ ID NO:53), GGGGDYALQGGGG (SEQ ID NO: 85), GGGDYALQGGGG (SEQ ID NO: 86), ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), or a combination thereof.

In one embodiment, the VitDBP comprises the sequence DYALQ (SEQ ID NO: 1) or the sequence GGGGDYALQGGGG (SEQ ID NO: 85). In yet another embodiment, the VitDBP can comprise a transglutaminase substrate peptide comprising a glutamine at the fifth position or the peptide can have a sequence motif comprising [FY][FYT]LQ, [YF]VAQ, K[YLS]K, or TKL.

In yet another embodiment, a VitDBP is described with the sequence:

```
                                           (SEQ ID NO: 87)
MKRVLVLLLAVAFGHALERGRDYEKNKVCKEFSHLGKEDFTSLSLVLYSR

KFPSGTFEQVSQLVKEVVSLTEACCAEGADPDCYDTRTSALSAKSCESNS

PFPVHPGTAECCTKEGLERKLCMAALKHQPQEFPTYVEPTNDEICEAFRK

DPKEYANQFMWEYSTNYGQAPLSLLVSYTKSYLSMVGSCCTSASPTVCFL

KERLQLKHLSLLTTLSNRVCSQYAAYGEKKSRLSNLIKLAQKVPTADLED

VLPLAEDITNILSKCCESASEDCMAKELPEHTVKLCDNLSTKNSKFEDCC

QEKTAMDVFVCTYFMPAAQLPELPDVELPTNKDVCDPGNTKVMDKYTFEL

SRRTHLPEVFLSKVLEPTLKSLGECCDVEDSTTCFNAKGPLLKKELSSFI

DKGQELCADYSENTFTEYKKKLAERLKAKLPDATPTELAKLVNKRSDFAS

NCCSINSPPLYCDSEIDAELKNILGGGSHHHHHHHGGGGDYALQGGGG.
```

Notably, the N-terminal sequence MKRVLVLLLAVAFGHA is removed from the VitDBP in vivo. Accordingly, in other embodiments, a VitDBP is described with the sequence:

```
                                           (SEQ ID NO: 91)
LERGRDYEKNKVCKEFSHLGKEDFTSLSLVLYSRKFPSGTFEQVSQLVKE

VVSLTEACCAEGADPDCYDTRTSALSAKSCESNSPFPVHPGTAECCTKEG

LERKLCMAALKHQPQEFPTYVEPTNDEICEAFRKDPKEYANQFMWEYSTN

YGQAPLSLLVSYTKSYLSMVGSCCTSASPTVCFLKERLQLKHLSLLTTLS

NRVCSQYAAYGEKKSRLSNLIKLAQKVPTADLEDVLPLAEDITNILSKCC

ESASEDCMAKELPEHTVKLCDNLSTKNSKFEDCCQEKTAMDVFVCTYFMP

AAQLPELPDVELPTNKDVCDPGNTKVMDKYTFELSRRTHLPEVFLSKVLE

PTLKSLGECCDVEDSTTCFNAKGPLLKKELSSFIDKGQELCADYSENTFT

EYKKKLAERLKAKLPDATPTELAKLVNKRSDFASNCCSINSPPLYCDSEI

DAELKNILGGGSHHHHHHHGGGGDYALQGGGG.
```

In another embodiment, the methods, peptide arrays, peptides, and proteins described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

III. Examples

Example 1: Assay Development

To test MTG (Zedira GmbH) specificity for Gln-substrate, N-(Biotinyl)cadaverine (Zedira GmbH) was used as a substitute for a Lys-substrate to biotinylate Gln-peptides on a peptide array synthesized using maskless light-directed peptide array synthesis. Similarly, to test MTG specificity for Lys-substrate, Z-Gln-Gly-CAD-Biotin (Zedira GmbH) was used as a substitute for a Gln-substrate to biotinylate Lys-peptides. Z-Gln-Gly-CAD-Biotin is a glutamine donor substrate for transglutaminases having the following formula:

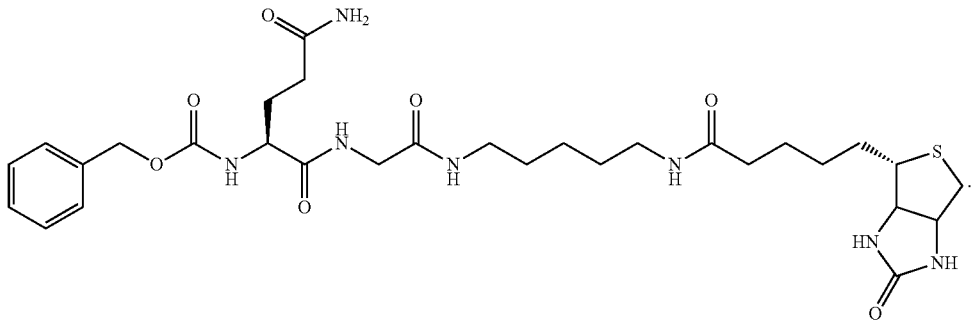 [SMILES: NC(=O)CC[C@H](NC(=O)OCc1ccccc1)C(=O)NCC(=O)NCCCCCNC(=O)CCCC[C@@H]1SCC2NC(=O)NC21]

After treatment with MTG in the presence of one of the biotinylated substrates, arrays were washed, stained with Cy5-streptavidin to label biotin moieties, and scanned at 635 nm to measure signal intensity at the peptide areas. Signal intensity corresponding to the efficiency of MTG reaction was used to determine specificity of different peptide sequences.

Example 2: Assay Conditions

In general, there were two issues to consider in optimizing array performance of the enzymatic assay originally developed under solution conditions. A first issue was a challenge of low signal generation that could be caused by the inability of the enzyme to recognize peptides bound to the surface, low peptide concentration, insufficient quality of peptide synthesis, or by surface effect on enzyme stability and reactivity. A second issue was a challenge of high background generation that may be a result of non-specific binding of the enzyme and/or a substrate to an array surface or non-specific labeling driven by side reactions on the array.

To find conditions for MTG assay on the array, the effects of various parameters of the reaction on signal and background generation were analyzed. These factors included MTG and substrate concentrations, reaction buffer composition, and incubation time and temperature. In order to minimize background, a non-protein blocking solution (Pierce) was used and it was found that its optimal concentration was 50% in the reaction buffer. Conditions used to study MTG specificity on the peptide array for both Lys-peptides and Gln-peptides are described herein.

Labeling of Lys-peptides on the array: 0.1 ng per μL MTG (Zedira GmbH); 10 μM Z-Gln-Gly-CAD-biotin (Zedira GmbH); 100 mM Tris-HCl pH 8, 1 mM dithiothreitol (DTT), 50% protein-free blocker (Pierce); 20 min at 37° C. Labeling of Gln-peptides on the array: 0.5 ng per μL MTG (Zedira GmbH); 50 μM N-(Biotinyl)cadaverine (Zedira GmbH); 100 mM Tris-HCl pH 8, 1 mM DTT, 50% protein-free blocker (Pierce); 1 h at 37° C.

Example 3: MTG Specificity for Gln-Peptides

A 5-mer peptide array was incubated in the presence of MTG and biotinylated amine donor N-(Biotinyl)cadaverine substrate under conditions described in Example 2. Signal distribution and correlation between two replicates was plotted (FIG. 1).

With reference to FIG. 1, correlation in signal intensity between replicates showed high reproducibility of the data and allowed identification of peptides with the highest labeling efficiency. Sequences and corresponding signal intensity of 25 peptides with the highest labeling efficiency in an array MTG assay with biotinylated amine-donor substrate discovered in this study are shown in Table 2. In concordance with MTG specificity, all peptides contained a Gln (Q) residue. Gln occupied exclusively the fifth position in all selected sequences. Because the 5-mer peptides synthesized on the array were flanked by G:S linkers for which a 3:1 mixture of Gly and Ser amino acid precursors was used, Gln may be followed by Gly in an optimal MTG substrate.

TABLE 2

| | Probe Sequence | Log$_2$(signal) |
|---|---|---|
| SEQ ID NO. 1 | DVALQ | 15.49 |
| SEQ ID NO. 2 | DYVLQ | 15.49 |
| SEQ ID NO. 3 | NYALQ | 15.49 |
| SEQ ID NO. 4 | EYALQ | 15.47 |
| SEQ ID NO. 5 | PYALQ | 15.44 |
| SEQ ID NO. 6 | EVYLQ | 15.41 |
| SEQ ID NO. 7 | DFALQ | 15.40 |
| SEQ ID NO. 8 | DYFLQ | 15.40 |
| SEQ ID NO. 9 | NYFLQ | 15.38 |
| SEQ ID NO. 10 | FYALQ | 15.37 |
| SEQ ID NO. 11 | DYTLQ | 15.31 |
| SEQ ID NO. 12 | NYVLQ | 15.31 |
| SEQ ID NO. 13 | EYVAQ | 15.29 |
| SEQ ID NO. 14 | RYALQ | 15.27 |
| SEQ ID NO. 15 | YFALQ | 15.27 |
| SEQ ID NO. 16 | PYVLQ | 15.26 |
| SEQ ID NO. 17 | WYALQ | 15.26 |
| SEQ ID NO. 18 | SYALQ | 15.24 |
| SEQ ID NO. 19 | HYALQ | 15.22 |

TABLE 2-continued

| | Probe Sequence | Log$_2$(signal) |
|---|---|---|
| SEQ ID NO. 20 | DYVAQ | 15.21 |
| SEQ ID NO. 21 | EFVAQ | 15.21 |
| SEQ ID NO. 22 | DFYLQ | 15.19 |
| SEQ ID NO. 23 | EFALQ | 15.19 |
| SEQ ID NO. 24 | EYFLQ | 15.19 |
| SEQ ID NO. 25 | NVFLQ | 15.19 |

Example 4: Motif Identification

To find a common motif, the top sequences identified by array MTG assay were analyzed with Peplib software that used principle component analysis to find motifs shared by short peptide sequences (Andrew D. White et al., *J. Chem. Inf. Model.*, 2013, 53 (2), pp 493-499). Turning to FIGS. 2A-2H, Analysis of top Gln-peptide substrates for MTG identified two closely related motifs that can be combined in a common motif [YF][VA]LQG, assuming that Gln is followed by Gly. That is, position 1 (of the 5-mer motif) is selected from the amino acids Y and F, position 2 is selected from the amino acids V and A, position 3 is the amino acid L, position 4 is the amino acid Q, and position 5 (not shown in FIGS. 2A-2H) is the amino acid G. Interestingly, the commercially available Gln-donor substrate, Z-Gln-Gly-CAD-biotin (Zedira GmbH), was a short two amino acid version of the motif found in the array MTG assay.

Example 5: Extension and Maturation of Gln-Motif Selected with 5-Mer Peptide Array The optimal DYALQ (SEQ ID NO: 1) sequence discovered by array MTG assay was selected for the second step of motif evolution that included motif extension and maturation. The 5-mer motif was elongated by three Gly residues from both the N- and C-terminus to create an 11-mer GGGDYALQGGG (SEQ ID NO: 26) sequence. This peptide and all of its possible single and double amino acid substitution variants were synthesized on a newly designed array using maskless light-directed peptide array synthesis, and tested for MTG activity. For the new array all 20 amino acids including Cys were used. The list of 27 sequences with the highest labeling efficiency is shown in Table 3. The extension and maturation step confirmed specificity of the 5-mer peptide selected in the first step and extended the DYALQ (SEQ ID NO: 1) 5-mer motif to a potentially more efficient GDYALQGPG (SEQ ID NO: 79) 9-mer motif

TABLE 3

| Sequence ID No. | Peptide Sequence |
|---|---|
| SEQ ID NO. 26 | G G G D Y A L Q G G G |
| SEQ ID NO. 27 | C G G D Y A L Q G P G |
| SEQ ID NO. 28 | W G G D Y A L Q G P G |
| SEQ ID NO. 29 | Y G G D Y A L Q G P G |
| SEQ ID NO. 30 | D G G D Y A L Q G P G |

TABLE 3-continued

| Sequence ID No. | Peptide Sequence |
|---|---|
| SEQ ID NO. 31 | G D G D Y A L Q G P G |
| SEQ ID NO. 32 | N G G D Y A L Q G P G |
| SEQ ID NO. 33 | G C G D Y A L Q G P G |
| SEQ ID NO. 34 | E G G D Y A L Q G P G |
| SEQ ID NO. 35 | P G G D Y A L Q G P G |
| SEQ ID NO. 36 | T G G D Y A L Q G P G |
| SEQ ID NO. 37 | Q G G D Y A L Q G P G |
| SEQ ID NO. 38 | I G G D Y A L Q G P G |
| SEQ ID NO. 39 | F G G D Y A L Q G P G |
| SEQ ID NO. 40 | H G G D Y A L Q G P G |
| SEQ ID NO. 41 | L G G D Y A L Q G P G |
| SEQ ID NO. 42 | V G G D Y A L Q G P G |
| SEQ ID NO. 43 | R G G D Y A L Q G P G |
| SEQ ID NO. 44 | G W G D Y A L Q G P G |
| SEQ ID NO. 45 | M G G D Y A L Q G P G |
| SEQ ID NO. 46 | S G G D Y A L Q G P G |
| SEQ ID NO. 47 | A G G D Y A L Q G P G |
| SEQ ID NO. 48 | G Y G D Y A L Q G P G |
| SEQ ID NO. 49 | G E G D Y A L Q G P G |
| SEQ ID NO. 50 | G P G D Y A L Q G P G |
| SEQ ID NO. 51 | G H G D Y A L Q G P G |
| SEQ ID NO. 52 | W D G D Y A L Q G G G |
| SEQ ID NO. 53 | G N G D Y A L Q G P G |

Example 6: Confirmation of Array-Selected Motif in a Solution Reaction

It was next determined whether peptides selected in the array assay were also preferred substrates in the solution reaction. The performance of the GGGDYALQGGGG (SEQ ID NO: 26) peptide found in the array assay and the QG peptide substrate commonly used for testing MTG activity were compared. The comparison of two substrates included a continuous enzyme-coupled assay for MTG activity developed by S. K. Oteng-Pabi and J. W. Keillor from the University of Ottawa was made (FIG. 3).

The assay was performed in a 96-well microtiter plate in the presence of 10 mM α-ketoglutarate, 10 mM glycine methyl ester as acyl acceptor, 2 U of glutamate dehydrogenase (GLDH), 500 µM NADH (i.e., reduced nicotinamide adenine dinucleotide) and Gln-containing substrate peptide concentrations ranging between 0.2 and 20 mM in 200 mM MOPS (i.e., 3-(N-morpholino)propanesulfonic acid), 1 mM EDTA pH 7.2 (total volume per well 200 µl). The reaction was started by the addition of 0.1 U of MTG (Zedira GmbH) and the oxidation of NADH was continuously recorded against a blank at 340 nm for 20 min using a Biotek Synergy H4 microplate reader thermostated at 37° C. with short shaking intervals before each measurement. After a short lag phase, where the GLDH was saturated by MTG-mediated release of ammonia, linear rates of absorbance versus time, corresponding to MTG turnover, were observed, and subjected to Michaelis-Menten kinetic analysis.

Figure 3:
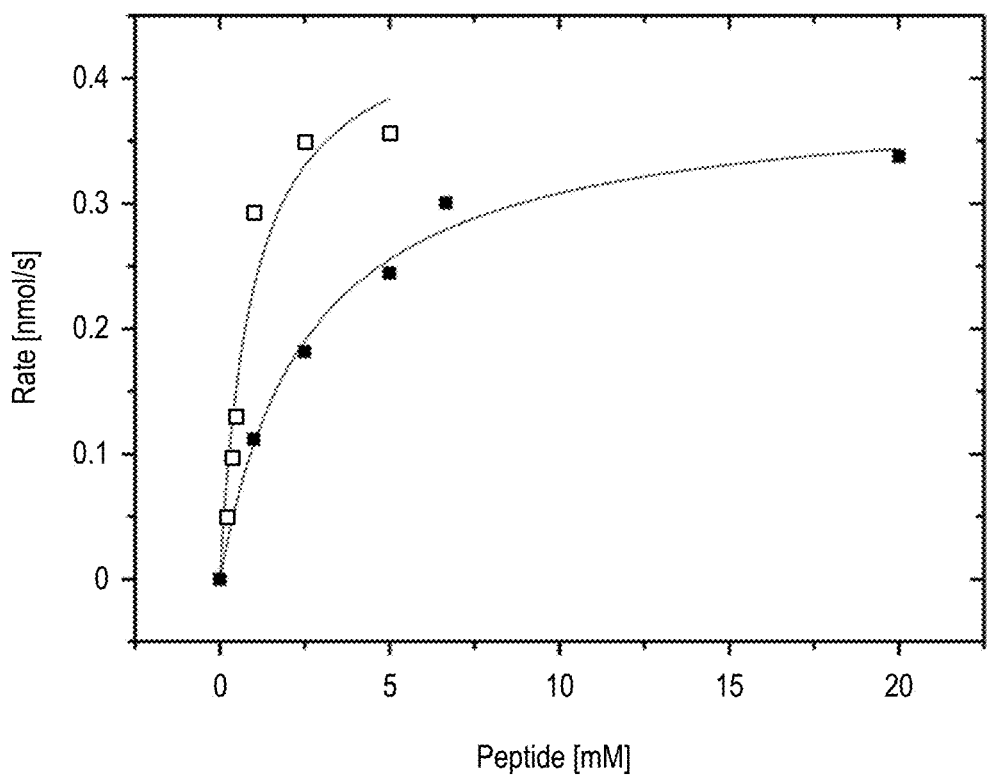
FIG. 3 is a plot of MTG activity obtained by measuring rates of NADH oxidation at 340 nm and 37° C. using various concentrations of the di-peptide QG (1-20 mM) and the peptide GGGDYALQGGGG (SEQ ID NO: 86) (0.2-5 mM) in the GLDH-coupled assay. The Michaelis-Menten equation was used to fit hyperbolic curves to the data points, giving $K_m$ and $V_{max}$ parameters and allowing calculation of turnover number ($k_{cat}$) and catalytic efficiency ($k_{cat}/K_M$). Improved performance of array selected GGGDY-ALQGGGG (SEQ ID NO: 86) (open squares) substrate was observed compared to standard QG-substrate (filled squares). 'Z' represents a carboxybenzyl protective group.

The results, as shown in FIG. 3 and Table 4, suggest that the array selected substrate had an improved performance compared to a standard QG-substrate, exhibiting a difference in MTG catalytic efficiency of at least 3-fold.

TABLE 4

| Gln-Peptide | $K_M$ [mM] | $V_{max}$ [nmol s$^{-1}$] | $k_{cat}$ [s$^{-1}$] | $k_{cat}/K_M$ [M$^{-1}$s$^{-1}$] |
|---|---|---|---|---|
| Z-GGGDYALQGGGG (SEQ ID NO: 2) | 0.97 ± 0.32 | 0.46 ± 0.06 | 6.0 | 6.2 × 10$^3$ |
| Z-QG | 2.61 ± 0.40 | 0.39 ± 0.02 | 5.1 | 1.9 × 10$^3$ |

Note that the 'Z-' in each of the peptide sequences in FIG. 3 and Table 4 represents a carboxybenzyl protective group having the formula:

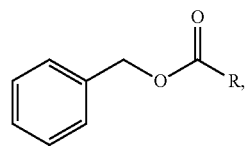

where R is the corresponding peptide sequence (e.g., QG or GGGDYALQGGGG).

Example 7: Confirmation of Another Array-Selected Motif in a Solution Reaction Lys-tag peptides were assayed in solution analog to the Gln-containing substrates: The assay was performed in a 96-well microtiter plate in the presence of 1.25 mM α-ketoglutarate, 100 µM Z-GGGDYALQGGGG (SEQ ID NO: 86) peptide as amine acceptor, 0.2 U of glutamate dehydrogenase (GLDH), 500 µM NADH and Lys-containing substrate peptide concentrations ranging between 0 and 500 µM in 200 mM MOPS, 1 mM EDTA pH 7.2 (total volume per well 200 µl). The reaction was started by the addition of 0.1 U of MTG (Zedira GmbH) and the oxidation of NADH was continuously recorded against a blank at 340 nm for 20 min using a Biotek Synergy H4 microplate reader thermostated at 37° C. with short shaking intervals before each measurement. After a short lag phase, where the GLDH was saturated by MTG-mediated release of ammonia, linear rates of absorbance versus time, corresponding to MTG turnover, were observed, and subjected to Michaelis-Menten kinetic analysis.

Figure 4:
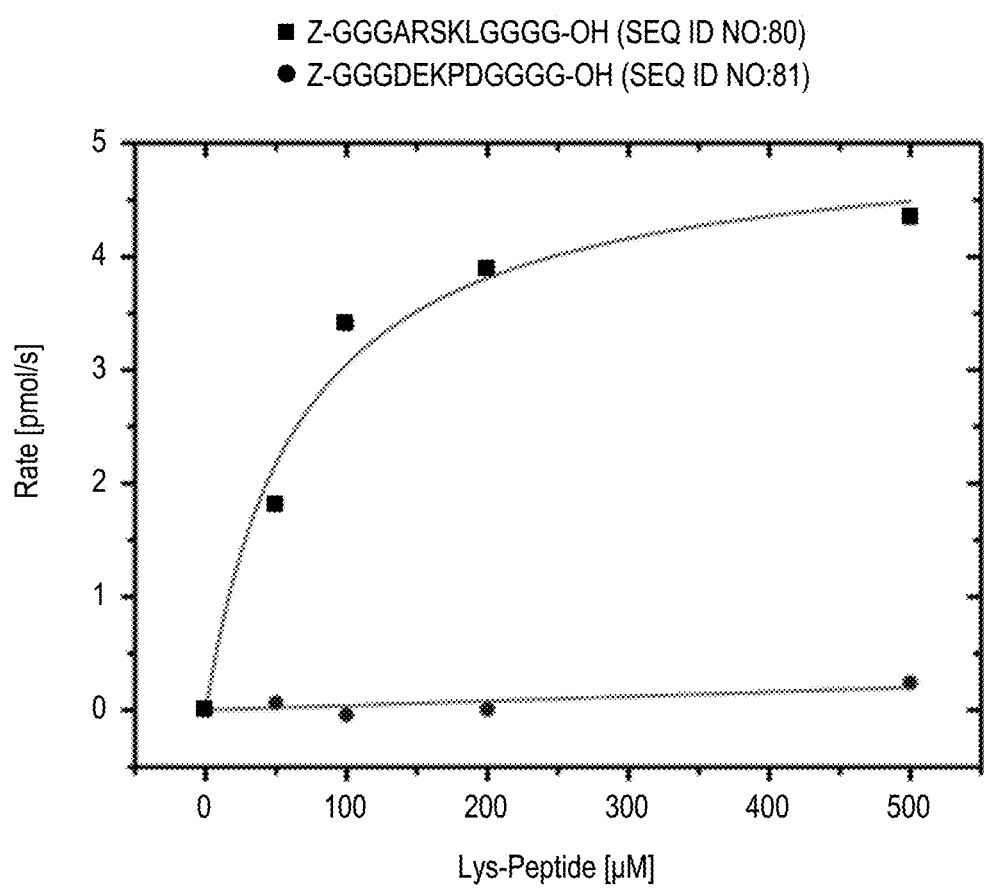
FIG. 4 shows plots of MTG activity obtained by measuring rates of NADH oxidation at 340 nm and 37° C. using various concentrations of the peptide GGGDEKPDGGGG (SEQ ID NO: 81) (0 to 500 µM) and the peptide GGGARSKLGGGG (SEQ ID NO: 80) (0 to 500 µM) in the GLDH-coupled assay. The Michaelis-Menten equation was used to fit hyperbolic curves to the data points, giving $K_m$ and $V_{max}$ parameters as well as allowing calculation of turnover number ($k_{cat}$) and catalytic efficiency ($k_{cat}/K_M$). Improved performance of array selected GGGARSKLGGGG (SEQ ID NO: 80) (filled squares) substrate was observed as compared to a GGGDEKPDGGGG (SEQ ID NO: 81) substrate (filled circles). 'Z-' represents a carboxybenzyl protective group.

The results, as shown in FIG. 4 and Table 5, confirm that the array-selected high-signal substrate GGGARSKLGGGG (SEQ ID NO: 80) had an improved performance compared to a low-signal substrate. Kinetic data of the GGGDEKPDGGGG (SEQ ID NO: 81) peptide could not be determined (indicated as "n. d." in Table 5) due to the extremely low activity, but an apparent difference in MTG catalytic efficiency of at least 10-fold was observed. The 'Z-' in each of the peptide sequences Table 5 represents a carboxybenzyl protective group as described above with reference to FIG. 3 and Table 4.

TABLE 5

| Lys-Peptide | $K_M$ [μM] | $V_{max}$ [pmol s$^{-1}$] | $k_{cat}$ [s$^{-1}$] | $k_{cat}/K_M$ [M$^{-1}$s$^{-1}$] |
|---|---|---|---|---|
| Z-GGGARSKLGGGG (SEQ ID NO: 80) | 66.8 ± 20.2 | 5.1 ± 0.5 | 0.0066 | 9.9 × 10² |
| Z-GGGDEKPDGGGG (SEQ ID NO: 81) | n.d. | n.d. | n.d. | n.d. |

Example 8: MTG Specificity for Lys-Peptides

To investigate specificity of MTG for Lys-substrate, the 5-mer peptide array was incubated in the presence of MTG and biotinylated Gln donor, Z-Gln-Gly-CAD-biotin (Zedira GmbH) substrate, under conditions described in Example 2. Signal distribution and correlation between two replicates is shown in FIG. 5.

Figure 5:
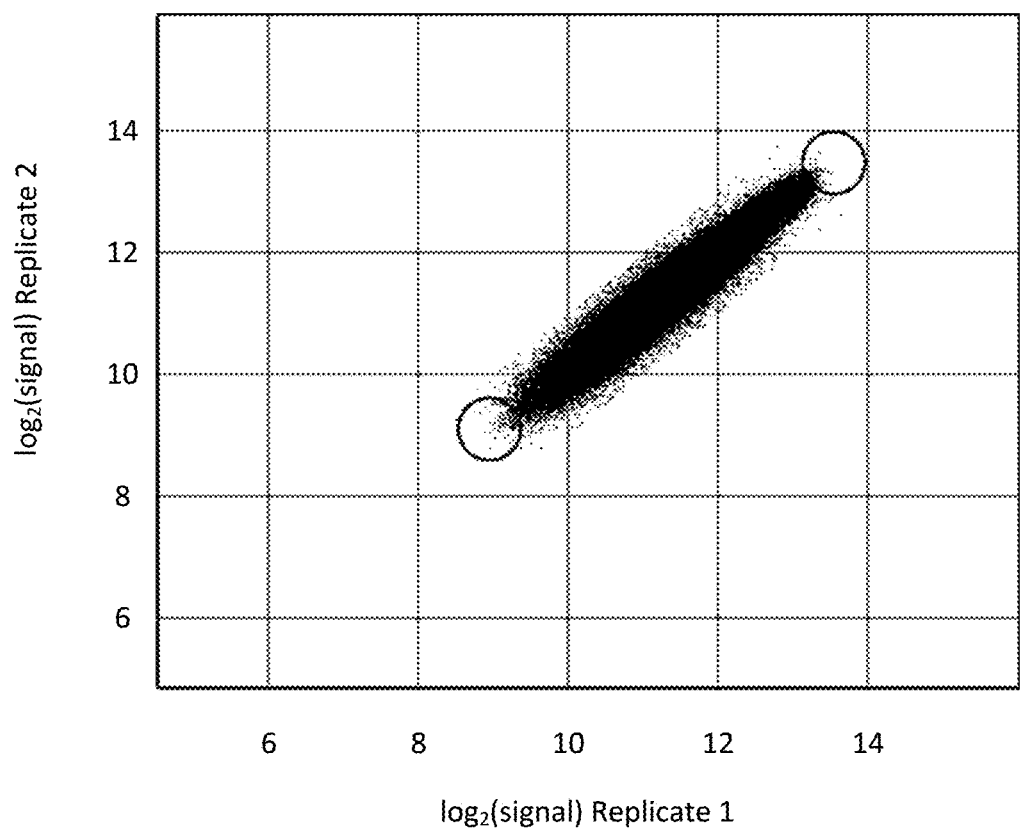
FIG. 5 is a log-log scatter plot showing the correlation between fluorescence signal data collected for replicate peptide features on a 5-mer peptide array labeled by MTG in the presence of a biotinylated Gln-donor substrate. Each dot represents one of 2.8 million peptide features from a library of 1.4 million unique peptide features synthesized in duplicate. Areas of low and high signal are indicated by circles in the lower left and upper right areas of the plot, respectively.

Twenty-five top sequences from the circled area at the top right of FIG. 5 (i.e., "high signal peptides") are shown in Table 6. All peptides contained at least one Lys (K) residue and the majority, 64%, had two Lys residues. Peplib analysis of the preferred Lys-peptide sequences revealed two closely related motifs, SK[LS]K and [KR][ST]KL.

TABLE 6

| Sequence ID No. | Probe Sequence | A |
|---|---|---|
| SEQ ID NO. 54 | ARSKL | 13.42 |
| SEQ ID NO. 55 | KSKLA | 13.41 |
| SEQ ID NO. 56 | TKSKL | 13.41 |
| SEQ ID NO. 57 | KLSKL | 13.40 |
| SEQ ID NO. 58 | RSKLG | 13.40 |
| SEQ ID NO. 59 | RGSKL | 13.39 |
| SEQ ID NO. 60 | RGTKL | 13.38 |
| SEQ ID NO. 61 | FPKLK | 13.37 |
| SEQ ID NO. 62 | RSKSK | 13.37 |
| SEQ ID NO. 63 | SKSKL | 13.37 |
| SEQ ID NO. 64 | FTKSK | 13.36 |
| SEQ ID NO. 65 | KLKYK | 13.36 |
| SEQ ID NO. 66 | PKTKL | 13.35 |
| SEQ ID NO. 67 | RLKSK | 13.35 |
| SEQ ID NO. 68 | RSKLA | 13.35 |
| SEQ ID NO. 69 | GRSKL | 13.34 |
| SEQ ID NO. 70 | RAKYK | 13.34 |
| SEQ ID NO. 71 | SKLSK | 13.34 |
| SEQ ID NO. 72 | KLGAK | 13.33 |
| SEQ ID NO. 73 | QRSKL | 13.33 |
| SEQ ID NO. 74 | KTKYK | 13.32 |
| SEQ ID NO. 75 | LSKLK | 13.32 |
| SEQ ID NO. 76 | NRTKL | 13.32 |
| SEQ ID NO. 77 | QRTKL | 13.32 |
| SEQ ID NO. 78 | GYKLK | 13.31 |

Example 9: Evolution of Discovered Motifs

Figure 6:
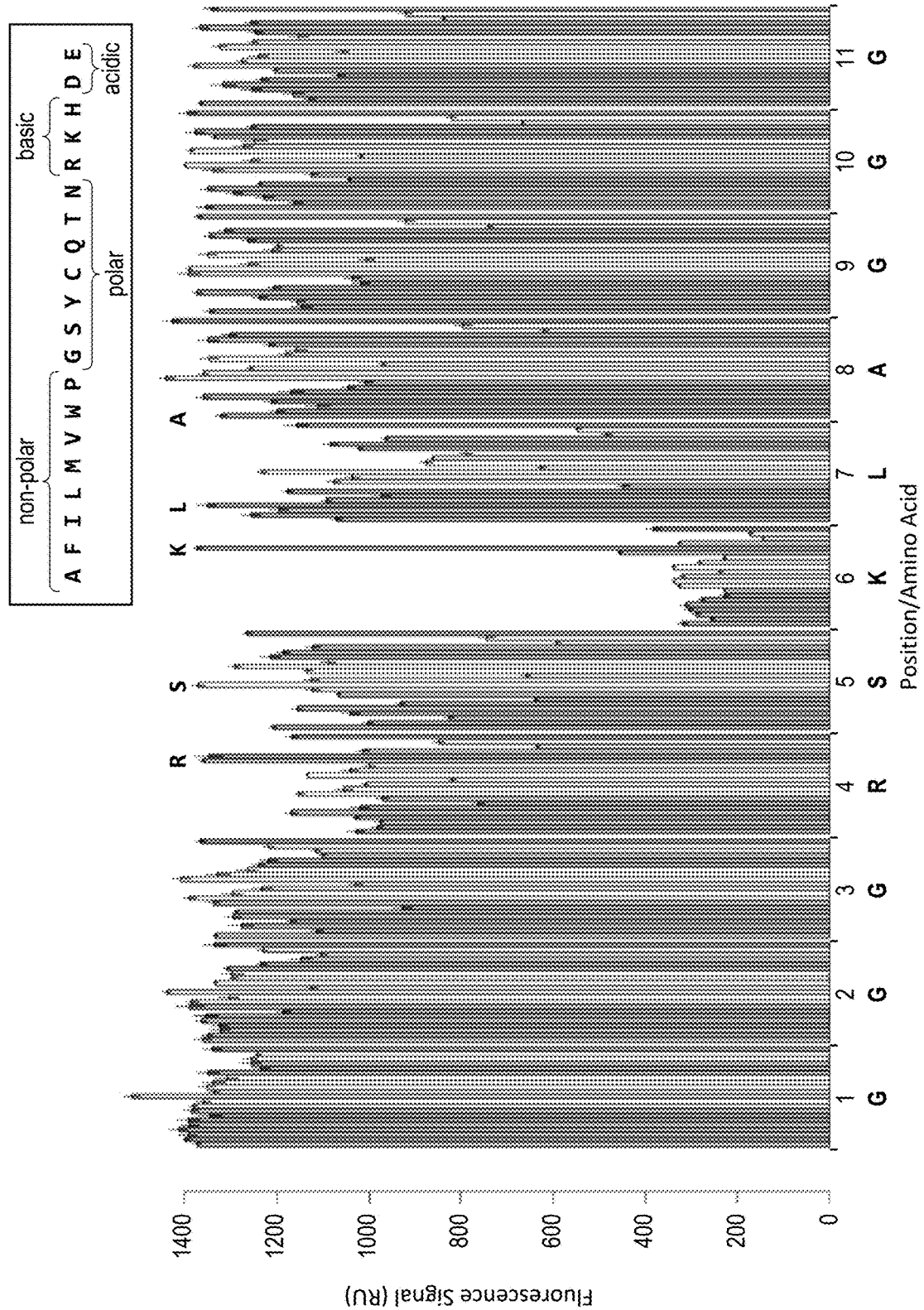
FIG. 6 is a single mutation scan amino acid substitution plot for the GGGRSKLAGGG (SEQ ID NO: 82) peptide. Each bar represents one of the 20 natural amino acids and the height of the bar corresponds to MTG generated signal intensity. For each peptide position the amino acids are arranged by category (non-polar, polar, basic, or acidic) in the following order from left to right: A, F, I, L, M, V, W, P, G, S, Y, C, Q, T, N, R, K, H, D, E. The right-most bar at each position corresponds to an amino acid deletion at that position. Data for the amino acids of the RSKLA motif are indicated by letters positioned above the corresponding bars.

To evolve the discovered motifs, one of the top sequences with a single Lys, RSKLA (SEQ ID NO: 68), was selected and extended with Gly residues to obtain the GGGRSK-LAGGG (SEQ ID NO: 82) sequence and a new array was designed that included this peptide and all possible single- and double amino acid substitution variants of its sequence. The peptide array was tested with an MTG activity assay in the presence of the biotinylated Gln-substrate. To demonstrate MTG specificity for the GGGRSKLAGGG (SEQ ID NO: 82) sequence MTG activity signal intensity was plotted for all single amino acid substitutions of the motif sequence (FIG. 6). The reactive Lys at position 6 was found to be highly conserved and could not be replaced by any other amino acid. Of the five amino acids in the RSKLA (SEQ ID NO: 68) motif, four residues showed the highest specificity at the corresponding positions, with exception of Ala at position 8 that could be replaced by Gly. Overall, it was found that MTG accepted a broad range of Lys substrates except possibly those that have either Asp (D) or Glu (E) acidic amino acid in the context of the reactive Lys.

Example 10: Site-Specific Labeling of VitDBP Using Array Selected Motifs

Figure 7:
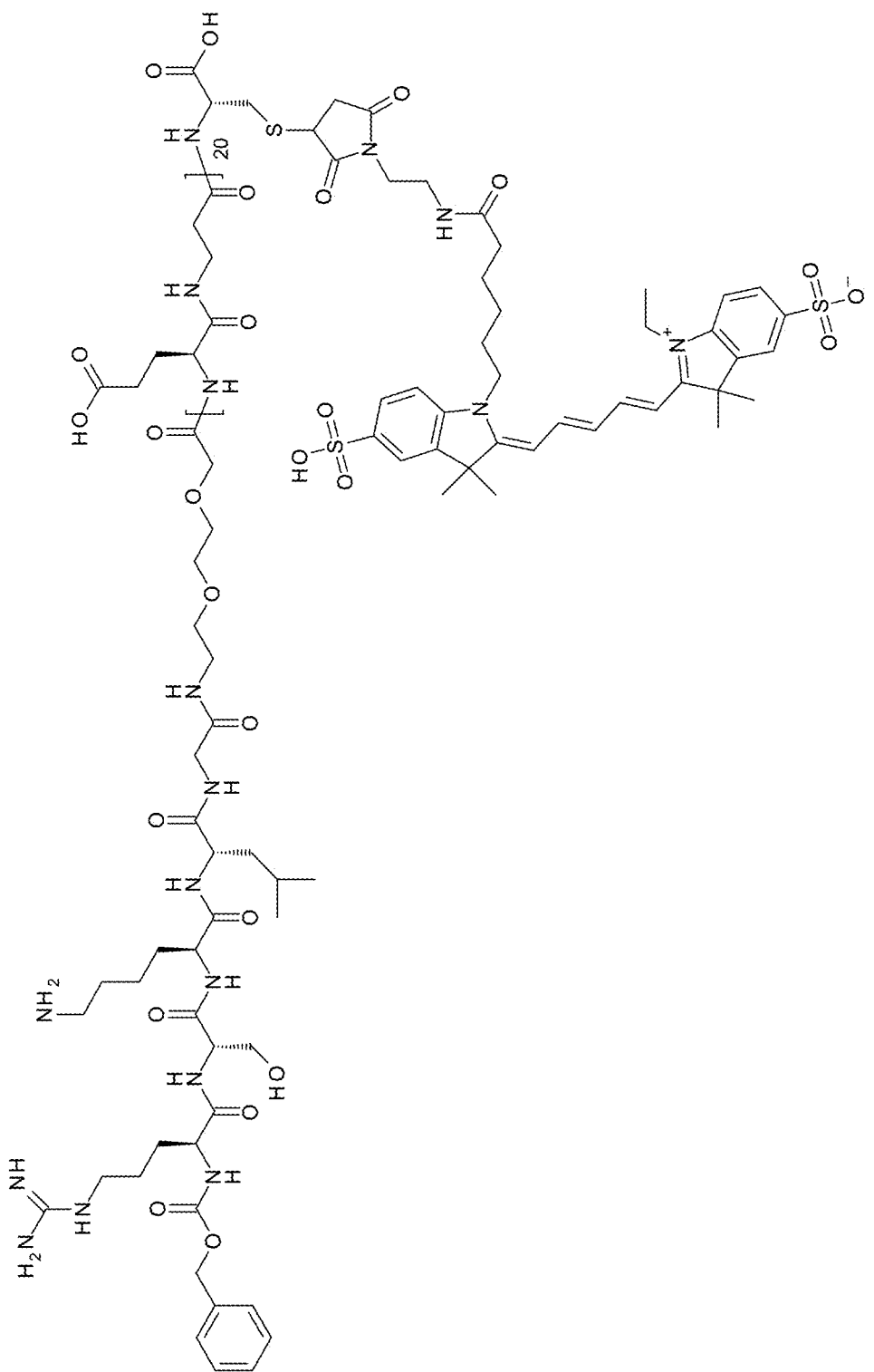
FIG. 7 shows a chemically synthesized Lys-Peptide-Cy5 fluorescent label.
Figure 8:
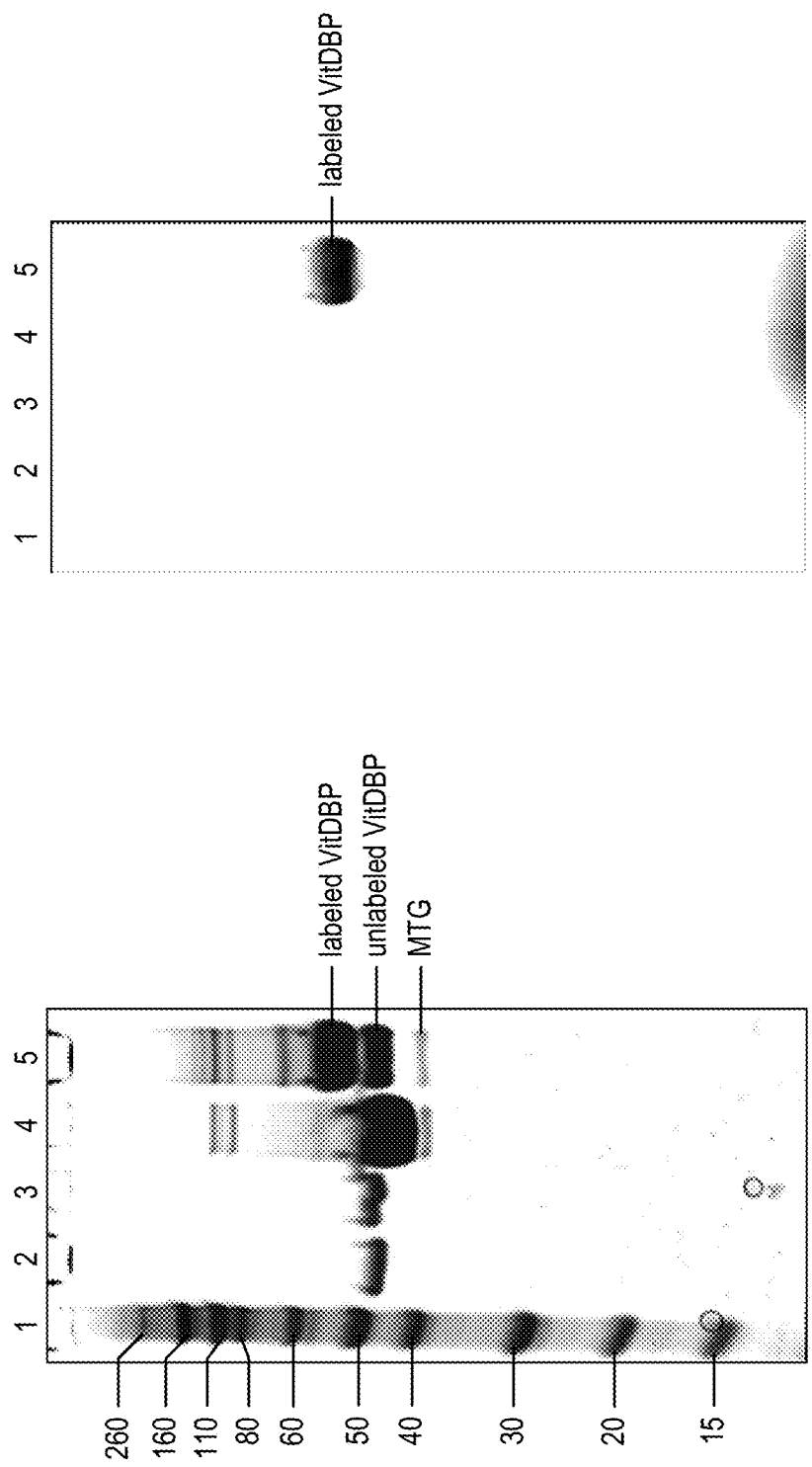
FIG. 8A is an optical image of an SD S-PAGE gel for analyzing site-specific Cy5 labeling of vitamin D binding protein with the fluorescent label of FIG. 7 using array selected motifs. Lane 1: Molecular Weight Ladder (values shown in kDa); Lane 2: wt-VitDBP-His8 without transglutaminase peptide; Lane 3: wt-VitDBP-His8-Q2 with transglutaminase peptide; Lane 4: wt-VDBP-His8 without transglutaminase peptide in the presence of fluorescent label and MTG; Lane 5: wt-VDBP-His8-Q2 with transglutaminase peptide in the presence of fluorescent label and MTG. See Detailed Description for abbreviations.
FIG. 8B is an image of the SDS-PAGE gel of FIG. 8A analyzed on a ChemiDoc CCD Imager equipped with a Cy5 LED & filter set showing Cy5 fluorescence.

Constructs were prepared for recombinant expression of VitDBP fused to either an octa-histidine tag (His8 tag) having the sequence HHHHHHHH (SEQ ID NO: 84), or both a His8 tag and a glutamine donor tag (Q2 tag) having the sequence GGGGDYALQGGGG (SEQ ID NO: 85). The recombinantly produced VitDBP with C-terminally fused His8 tag and Q2 tag (wt-VitDBP-His8-Q2), and VitDBP with a C-terminally fused His8 tag, but without a C-terminally fused Q2 tag (wt-VitDBP-His8) were incubated with a chemically synthesized Lys-Peptide-Cy5 fluorescent label (FIG. 7) and with MTG. The C-terminal amino acid sequences and the molecular weights of wt-VitDBP-His8-Q2 and wt-VitDBP-His8 were HHHHHHHHGGGGDY-ALQGGGG (SEQ ID NO: 83), 53618.8 Da and HHHHHHHH (SEQ ID NO: 84), 52571.7 Da, respectively. The N-terminal sequence of the labeled molecule was Z-RSKLG (SEQ ID NO: 58) where 'Z represents a carboxybenzyl protective group. The total molecular weight of the label was 5724.9 Da. For the labeling reaction, 10 μg (0.19 nmol) of wt-VitDBP-His8-Q2 or wt-VitDBP-His8 was mixed with 10.9 μg (1.9 nmol) of the label and 0.004 U of MTG (Zedira GmbH) in a total volume of 6.48 μl or 5.81 μl respectively. The reaction was performed for 15 min at 37° C. in 50 mM HEPES (i.e., 4-(2-hydroxyethyl)-1-piperazineethanesulfonic acid), 150 mM NaCl, pH 7.5 and was stopped by passing the mixture through a column packed with Ni-NTA Superflow (Qiagen). The column was washed with 5 CV of 50 mM HEPES, 150 mM NaCl, pH 7.5 and His-tagged protein eluted with 500 mM imidazole. Aliquots of the eluates were analyzed by sodium dodecyl sulfate polyacrylamide gel electrophoresis (SDS-PAGE), as shown in FIGS. 8A and 8B. Labeled protein was identified by the molecular weight shift on the gel stained with coomassie blue (FIG. 8A) and by Cy5 fluorescence (FIG. 8B) analyzed on a ChemiDoc CCD Imager equipped with a Cy5 LED & filter set (BioRad).

The sequence for wt-VitDBP-His8-Q2 is as follows:

(SEQ ID NO: 91)
LERGRDYEKNKVCKEFSHLGKEDFTSLSLVLYSRKFPSGTFEQVSQLVKE

VVSLTEACCAEGADPDCYDTRTSALSAKSCESNSPFPVHPGTAECCTKEG

LERKLCMAALKHQPQEFPTYVEPTNDEICEAFRKDPKEYANQFMWEYSTN

YGQAPLSLLVSYTKSYLSMVGSCCTSASPTVCFLKERLQLKHLSLLTTLS

NRVCSQYAAYGEKKSRLSNLIKLAQKVPTADLEDVLPLAEDITNILSKCC

ESASEDCMAKELPEHTVKLCDNLSTKNSKFEDCCQEKTAMDVFVCTYFMP

AAQLPELPDVELPTNKDVCDPGNTKVMDKYTFELSRRTHLPEVFLSKVLE

PTLKSLGECCDVEDSTTCFNAKGPLLKKELSSFIDKGQELCADYSENTFT

EYKKKLAERLKAKLPDATPTELAKLVNKRSDFASNCCSINSPPLYCDSEI

DAELKNILGGGSHHHHHHHHGGGGDYALQGGGG.

Figure 9:
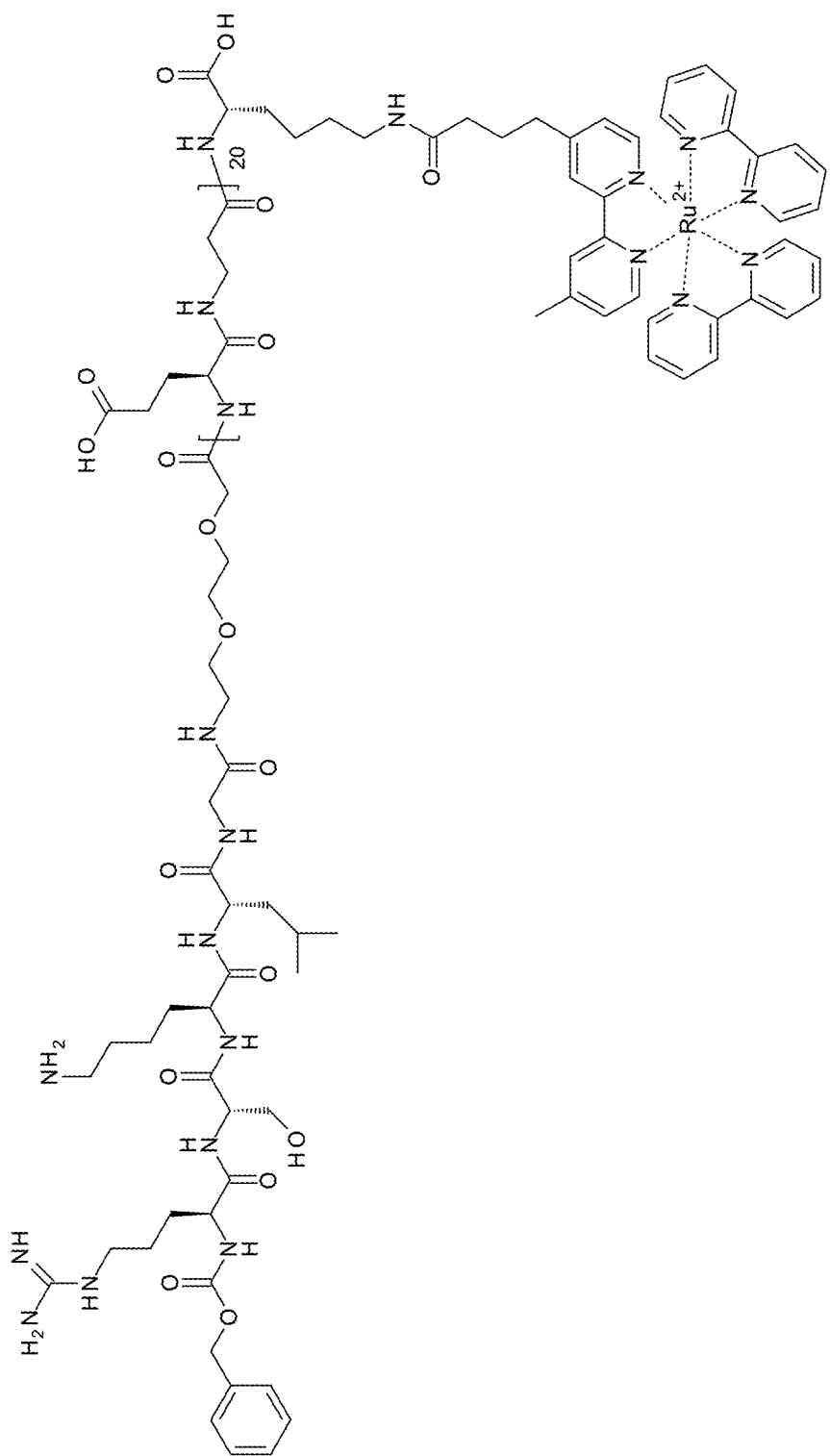
FIG. 9 shows a chemically synthesized Lys-Peptide-ruthenium label.

Example 11: Site-Specific Biotin and BPRuthenium Labeling of VitDBP Using Array Selected Motifs Recombinantly produced wt-VitDBP-His8-Q2 and wt-VitDBP-His8 were incubated with a chemically synthesized Lys-Peptide-Biotin or Lys-Peptide-BPRuthenium label (FIG. 9) and with MTG. The C-terminal amino acid sequences and molecular weights of wt-VDitBP-His8-Q2 and wt-VitDBP-His8 were HHHHHHHHGGGGDY-ALQGGGG (SEQ ID NO: 83) (53618.8 Da) and HHHHHHHH (SEQ ID NO: 84) (52571.7 Da), respectively. The N-terminal sequence of the label molecules was Z-RSKLG (SEQ ID NO: 58), and the total molecular weight of the Biotin and BPRuthenium labels was 1267.4 Da and 5623.7 Da, respectively. For the Biotin labeling reaction, 0.4 nmol of wt-VitDBP-His8-Q2 or wt-VitDBP-His8 were mixed with 4 nmol of the label and 0.008 U of MTG (Zedira GmbH) in a total volume of 13.3 µl or 11.8 µl, respectively. The reaction was performed at 37° C. in 200 mM MOPS, 1 mM EDTA, pH 7.2. After 15, 30, and 60 min incubation, 3 µl aliquots were taken and analyzed by SDS-PAGE and Western Blot (iBlot, Life Technologies) using Streptavidin-HRP conjugate (NEB) diluted 1:2000 in SuperBlock TBS (Pierce). Labeled protein was identified by the molecular weight shift on the membrane stained with Ponceu S and by chemiluminescent detection of the biotin label via Streptavidin-HRP analyzed on a CCD Imager (LAS-3000, Fujifilm).

For the BPRuthenium labeling reaction, 2 nmol of wt-VitDBP-His8-Q2 or wt-VitDBP-His8 was mixed with 20 nmol of the label and 0.04 U of MTG (Zedira GmbH) in a total volume of 48.5 µl or 41.3 µl, respectively. The reaction was performed for 15 min at 37° C. in 200 mM MOPS, 1 mM EDTA, pH 7.2. Excess label was removed by dialyzing against buffer using centrifugal filters with 10 K MWCO (Amicon Ultra, EMD Millipore). Aliquots were analyzed by SDS-PAGE. Labeled protein was identified by the molecular weight shift on the gel stained with coomassie blue (FIG. 10A) and by BPRuthenium fluorescence (FIG. 10B) analyzed on a CCD Imager equipped with a Blue LED & 605 nm emission filter (ChemiDoc, BioRad).

Example 12: Addition of Array-Selected Motifs to VitDBP does not Interfere with Binding to the Natural Ligand Experiments were carried out to determine whether the addition of an array-selected motif interferes with the ability of VitDBP to bind to its natural ligand, 25-hydroxylated vitamin D2 (25-OH-VitD2). The glutamine donor motif selected for use was GGGGDYALQGGGG (i.e., SEQ ID NO 86). A BIACORE SA sensor was mounted into a BIACORE 3000 instrument. The instrument was tempered at 25° C. The sensor was preconditioned as recommended by the manufacturer (GE Healthcare). The system buffer was PBS pH 8.2 with 5% DMSO and 0.05% TWEEN20. The sample buffer was the system buffer supplemented with 1 mg per ml CMD (Sigma). From a 300 nM biotin labeled 25-OH-VitD2 (25-OH-VitD2-bi) sample solution 860 RU were captured on the sensor flow cell 2 by a 2 min injection at 10 µl per minute. The sensor surface was finally saturated by 5 µM amino-PEO-biotin (Pierce). As a reference, 1 µM amino-PEO-biotin was injected into flow cell 1 for 1 min at a rate of 10 µl per minute.

Figure 10B:
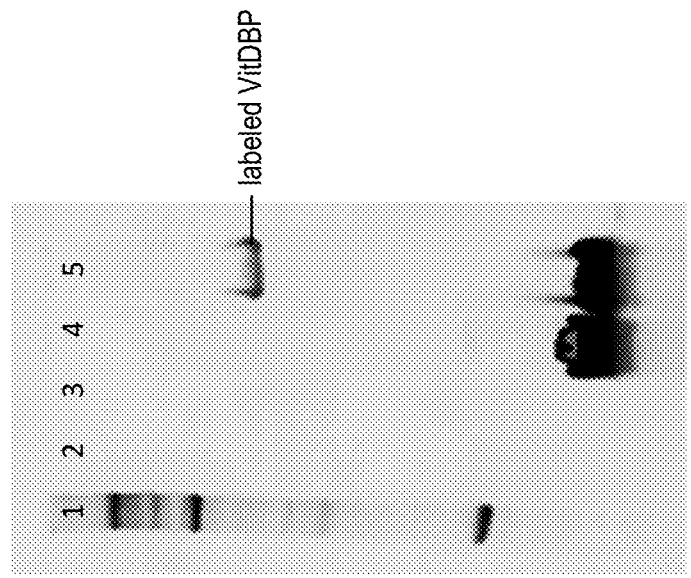
FIG. 10B is an image of the SDS-PAGE gel of FIG. 10A analyzed on a ChemiDoc CCD Imager equipped with a Cy5 LED & filter set showing Cy5 fluorescence.
Figure 10A:
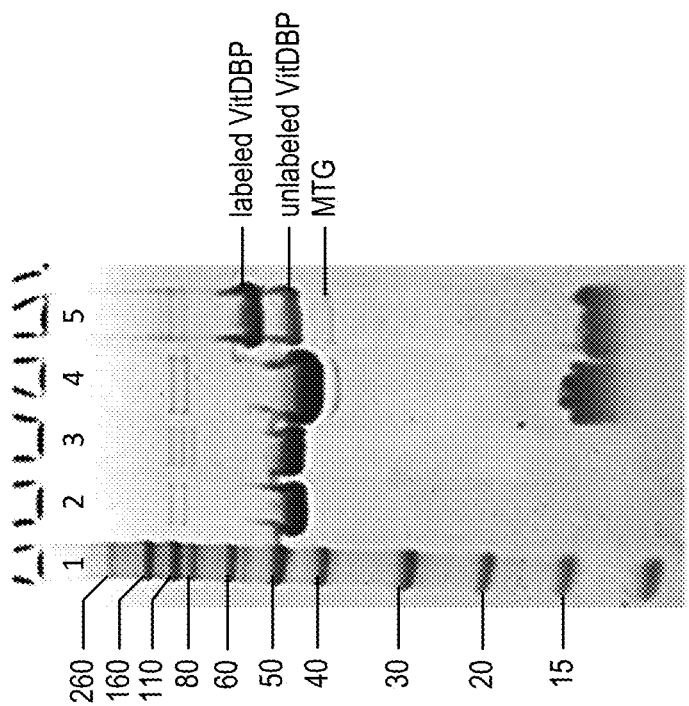
FIG. 10A is an optical image of an SDS-PAGE gel for analyzing site-specific Ruthenium labeling of vitamin D binding protein with the fluorescent label of FIG. 9. Lane 1: Molecular Weight Ladder (values shown in kDa); Lane 2: wt-VDBP-His8 without transglutaminase peptide; Lane 3: wt-VDBP-His8-Q2 with transglutaminase peptide; Lane 4: wt-VDBP-His8 without transglutaminase peptide in the presence of fluorescent label and MTG; Lane 5: wt-VDBP-His8-Q2 with transglutaminase peptide in the presence of fluorescent label and MTG. See Detailed Description for abbreviations.

The analytes wt-VitDBP-His8 and wt-VitDBP-His8-Q2 were compared for their binding behavior towards 25-OH-VitD2. The Gln-motif was later ruthenylated by an MTG catalyzed reaction as described (FIGS. 10A and 10B).

Figure 11:
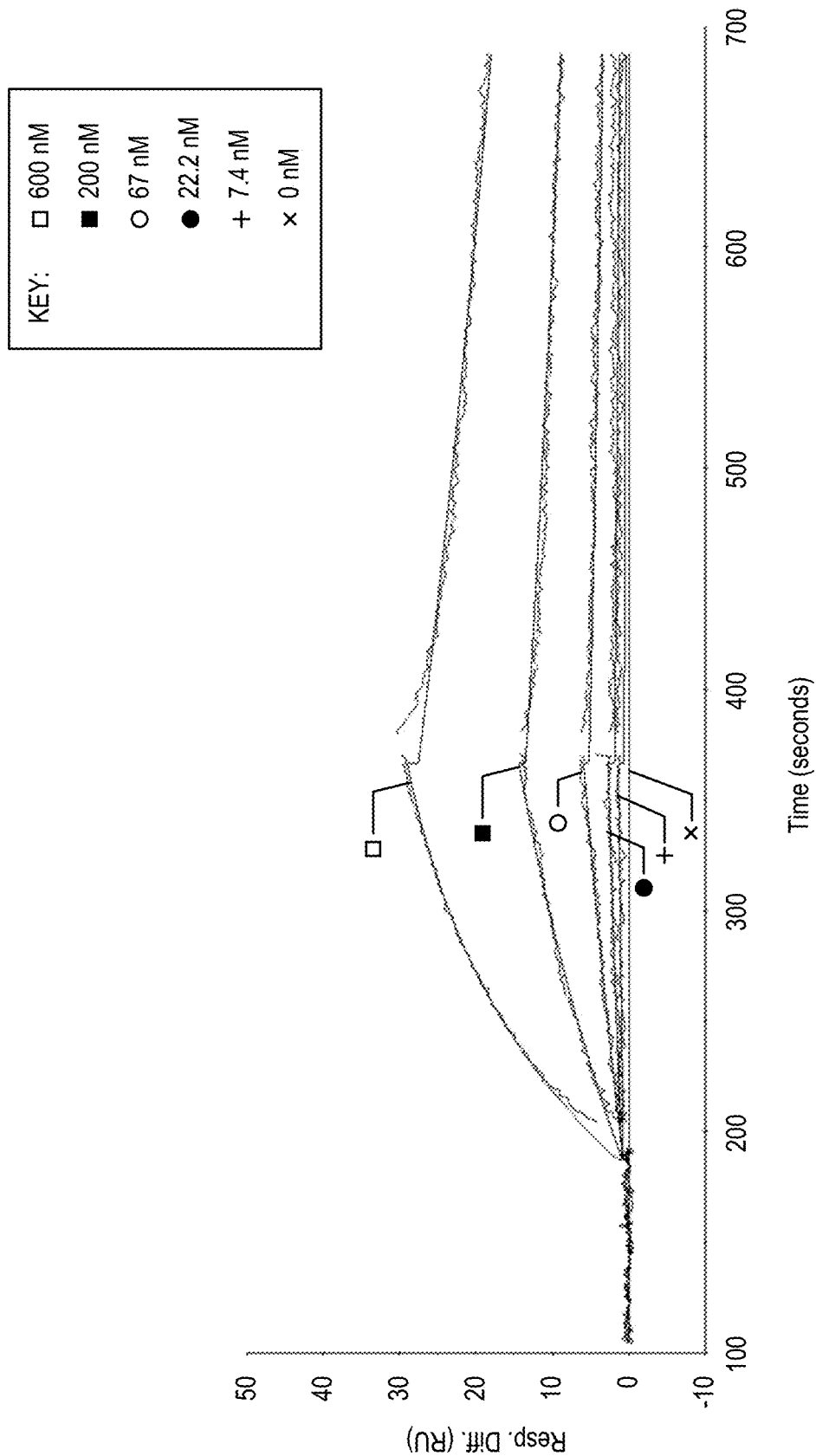
FIG. 11 shows the kinetics of wild type vitamin D binding protein with an 8× Histidine tag (wt-VDBP-His8) to a biotin-modified natural vitamin D ligand. BIACORE 3000; Ligand: VitD2-250H-biotin (300 nM); wt-VDBP-His8 concentrations, top to bottom traces: 600 nM, 200 nM, 67 nM, 22.2 nM, 7.4 nM, 0 nM; KD=95 nM.
Figure 12:
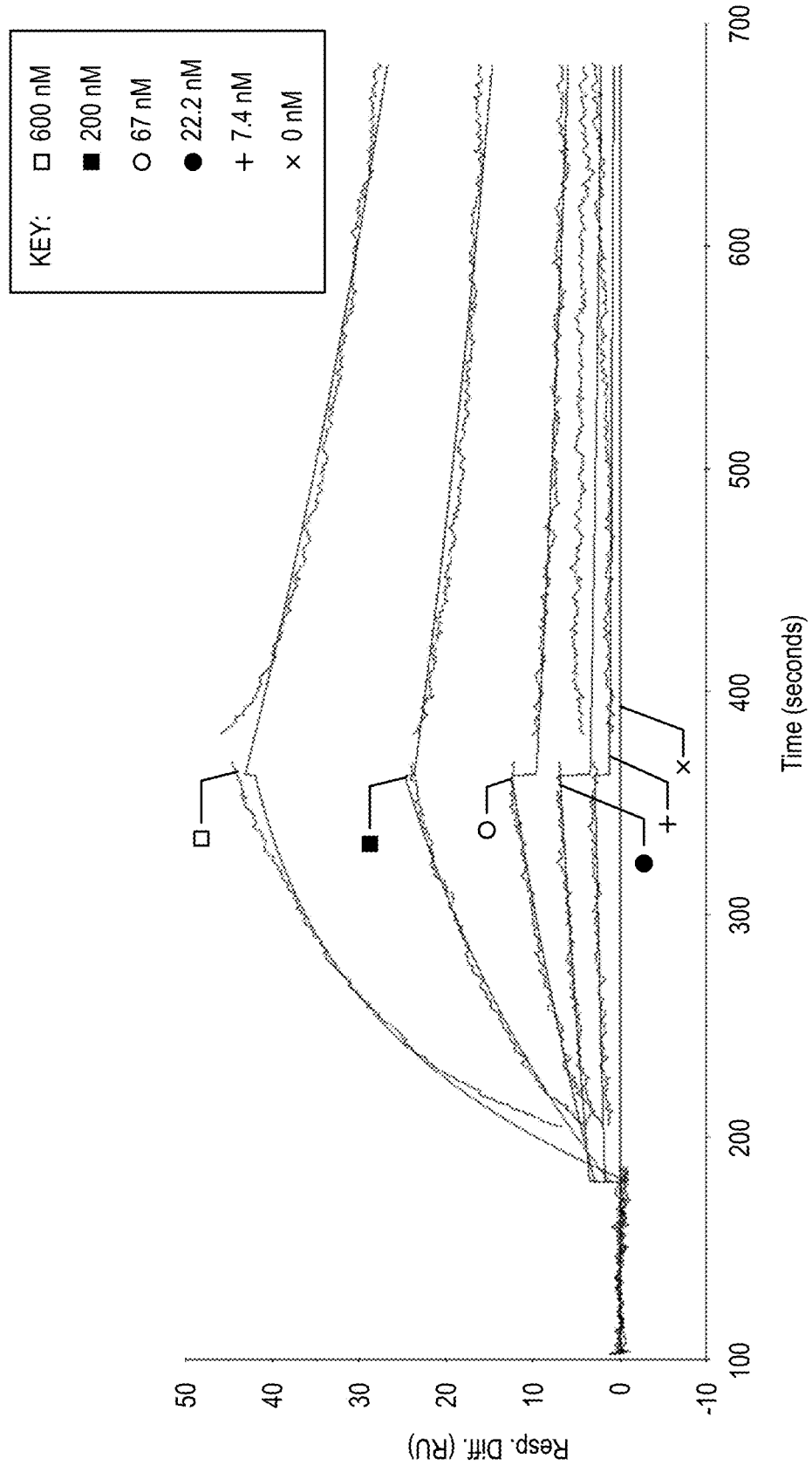
FIG. 12 shows the kinetics of wild type vitamin D binding protein with an 8× Histidine tag and a Q2 tag (wt-VDBP-His8-Q2) to a biotin-modified natural vitamin D ligand. BIACORE 3000; Ligand: VitD2-250H-biotin (300 nM); wt-VDBP-His8-Q2 concentrations, top to bottom traces: 600 nM, 200 nM, 67 nM, 22.2 nM, 7.4 nM, 0 nM; KD=93 nM.

The analytes were injected in concentration series of 600 nM, 200 nM, 67 nM, 22 nM, 7.4 nM and 0 nM (buffer only). The analyte association was monitored for 3 min and the dissociation for 5 min both at 20 µl per minute (FIGS. 11 and 12).

After each injection the system was regenerated by a 100 mM HCl injection for 1 minute and 15 seconds at 20 µl per minute followed by a 2 min injection of 10 mM glycine buffer pH 1.5. The data was overlayed in a BIACORE sensorgram and kinetic data was calculated by fitting a Langmuir 1:1 binding model to the data obtained as recommended by the manufacturer using the Biaevaluation Software version 4.1.

One goal of the assay of Example 12 was to investigate whether addition of an array-selected Gln-motif interferes with the ability of VitDBP to interact with its natural ligand (e.g., 25-OH-VitD). For wt-VDBP-His8: $k_a=1.38\times10^4$ $M^{-1}$ $s^{-1}$, $k_d=1.31\times10^{-3}$ $s^{-1}$, $K_D=9.5\times10^{-8}$ M (FIG. 11). For wt-VDBP-His8-Q2: $k_a=1.55\times10^4$ $k_d=1.44\times10^{-3}$ $s^{-1}$, $K_D=9.3*10^{-8}$ M (FIG. 12). Therefore, as the kinetic profiles are identical, it was determined that the Gln-motif does not impact the VitDBP kinetics in this assay.

Construction of wt-VDBP-His8-Q2 Expression Plasmid:

The wt-VDBP-His8-Q2 gene [wtVDBP(Gc1F)-GGGS-(His)8-GGGGDYALQGGGG] was PCR amplified from the wtVDBP-His8 pM1MT plasmid using the following primers:

F1 primer:
(SEQ ID NO: 88)
CAGACATAATAGCTGACAGACTAACAGACTGTTCC

R1 primer:
(SEQ ID NO: 89)
GTGATCTGGATCCTTATCACACCTCGATGTGGTCGGGCAGGTCCACGATC

TTTCCACCGTGATGGTGGTGATGGTGGTGATG $R_{help}$ primer:
(SEQ ID NO: 90)
GTGATCTGGATCCTTATCAACCGCCTCC PCR conditions are shown in Table 7. The PCR product was digested using SalI-HF/BamHI-HF and purified by agarose gel electrophoresis. The new gene (wt-VDBP-His8-Q2) was inserted again into the pM1MT expression vector.

TABLE 7

| PCR condition | | |
| --- | --- | --- |
| Step 1 | 94° C. | 5 min |
| Step 2 | 94° C. | 30 s |
| Step 3 | 60° C. | 30 s |
| Step 4 | 72° C. | 90 s |
| Repeat steps (2-4) 29X | | |
| Step 5 | 72° C. | 5 min |

Expression in HEK293 Cells:

The transfection protocol was performed as follows. $2\times10^6$ cells per ml were used in FreeStyle 293 Expression Medium (Gibco). Novagen Transfection reagent was used. 10 μg plasmid DNA was added to 20 ml of cell culture. 4 mM Valproic acid was added 3 hours after transfection. Feed 7 (L-glutamine, D-glucose, L-asparagine, soy peptone) was added during the 7 day expression time.

Purifications with NiNTA Gravity Flow Column:

NiNTA metal-affinity resin (Qiagen) was incubated by supernatant overnight. The resin was washed several times with buffer A (50 mM HEPES, 110 mM NaCl; pH 7.5). Protein was eluted with buffer B (50 mM HEPES, 360 mM NaCl, 250 mM imidazole; pH7.5). Protein concentration was determined by UV-Spectrophotometry at 280 nm with extinction coefficient 0.573.

Example 13: Microarrays and their Use

Various methods for the production of microarrays are known in the state of the art. For example, spotting prefabricated peptides or in-situ synthesis by spotting reagents, e.g., on membranes, exemplify known methods. Other known methods used for generating peptide arrays of higher density are the so-called photolithographic techniques, where the synthetic design of the desired biopolymers is controlled by suitable photolabile protecting groups (PLPG) releasing the linkage site for the respective next component (e.g., amino acid) upon exposure to electromagnetic radiation, such as light (Fodor et al., (1993) Nature 364:555-556; Fodor et al., (1991) Science 251:767-773). Two different photolithographic techniques are known in the state of the art. The first is a photolithographic mask, used to direct light to specific areas of the synthesis surface effecting localized deprotection of the PLPG. "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 and 5,445,934, the disclosures of which are hereby incorporated by reference. The second photolithographic technique is maskless photolithography, where light is directed to specific areas of the synthesis surface effecting localized deprotection of the PLPG by digital projection technologies, such as micromirror devices (Singh-Gasson et al., Nature Biotechn. 17 (1999) 974-978). It should be understood that the embodiments of the methods disclosed herein may comprise or utilize any of the various array synthesis techniques described above.

The use of PLPG (photolabile protecting groups), providing the basis for the photolithography based synthesis of peptide microarrays, is well known in the art. Commonly used PLPG for photolithography based biopolymer synthesis are for example α-methyl-6-nitropiperonyl-oxycarbonyl (MeNPOC) (Pease et al., Proc. Natl. Acad. Sci. USA (1994) 91:5022-5026), 2-(2-nitrophenyl)-propoxycarbonyl (NP-POC) (Hasan et al. (1997) Tetrahedron 53: 4247-4264), nitroveratryloxycarbonyl (NVOC) (Fodor et al. (1991) Science 251:767-773) and 2-nitrobenzyloxycarbonyl (NBOC) (Patchornik et al. (1970) 21:6333-6335.

Amino acids have been introduced in photolithographic solid-phase peptide synthesis of peptide microarrays, which were protected with NPPOC as a photolabile amino protecting group, wherein glass slides were used as a support (U.S. Patent Publication No. 2005/0101763 A1). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

A single microarray or, in some cases, multiple microarrays (e.g., 3, 4, 5, or more microarrays) can be located on one solid support. The size of the microarrays depends on the number of microarrays on one solid support. The higher the number of microarrays per solid support, the smaller the arrays have to be to fit on the solid support. The arrays can be designed in any shape, but preferably they are designed as squares or rectangle.

The term feature refers to a defined area on the surface of a microarray. The feature comprises biomolecules, such as peptides, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micro mirror device. For example, the state of the art micro mirror device from Texas Instruments, Inc. currently contains 4.2 million mirror elements (pixels), thus the number of features within such exemplary microarray is therefore limited by this number. However, it should be understood that the micro mirror device from Texas Instruments, Inc. is provided only for exemplary purposes and higher density arrays are possible.

It should be understood that the term solid support refers to any solid material, having a surface area to which organic molecules can be attached through bond formation or absorbed through electronic or static interactions such as covalent bond or complex formation through a specific functional group. The support can be a combination of materials such as plastic on glass, carbon on glass, and the like. The functional surface can be simple organic molecules but can also comprise of co-polymers, dendrimers, molecular brushes, and the like. Plastic can be used as a support and preferably the plastic is a polyolefin with defined optical properties, like TOPAS® or ZEONOR/EX®.

The term "functional group" as used herein refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol, and nitril. Potentially reactive functional groups include, for example, amines, carboxylic acids, alcohols, double bonds, and the like. Preferred functional groups are potentially reactive functional groups of amino acids such as amino groups or carboxyl groups.

As understood by one of skill in the art, peptide microarrays comprise an assay principle whereby thousands (or millions) of peptides (in some embodiments presented in multiple copies) are linked or immobilized to the surface of a solid support (which in some embodiments comprises a glass, carbon composite and/or plastic chip or slide). According to embodiments of the instant disclosure, peptide microarrays may be incubated with enzymes. In some embodiments, the peptide microarray, after incubation with a sample of interest (e.g. an enzyme), undergoes one or more washing steps, and then is exposed to a detection system, for example, utilizing fluorescence, chemiluminescence, colorimetric methods, or autoradiography.

In the case of binding events, after scanning the microarray slides, the scanner can record a 20-bit, 16-bit or 8-bit numeric image in tagged image file format (*.tif). The .tif-image enables interpretation and quantification of the data obtained from the scanned microarray slide. This quantitative data can be the basis for performing statistical analysis on measured binding events or peptide modifications on the microarray slide. For evaluation and interpretation of detected signals an allocation of the peptide spot (visible in the image) and the corresponding peptide sequence has to be performed. The data for allocation is usually saved in the GenePix Array List (.gal) file and supplied together with the peptide microarray. The .gal-file (a tab-separated text file) can be opened using microarray quantification software-modules or processed with a text editor (e.g. notepad) or Microsoft Excel. This 'gal' file is most often provided by the microarray manufacturer and is generated by input txt files and tracking software built into the robots that do the microarray manufacturing.

A peptide microarray is a planar slide with peptides spotted onto it or assembled directly on the surface by in-situ synthesis. Peptides are ideally covalently linked through a chemoselective bond leading to peptides with the same orientation for interaction profiling. Alternative procedures include unspecific covalent binding and adhesive immobilization.

After identification of a core hit peptide sequence, a process of "peptide maturation" can be conducted whereby the core hit peptide sequence is altered in various ways (through amino acid substitutions, deletions and insertions) at each position of the core hit peptide in order to further optimize/verify the proper core hit sequence. For example, according to some embodiments (for example, where the core hit peptide sequence comprises a given number of, such as 5, amino acids), a maturation array is produced. The maturation array (second peptide array) may have, for example, immobilized thereto, a population of core hit peptides whereby each amino acid in the core hit peptide has undergone an amino acid substitution at each position.

An example/hypothetical core hit peptide is described as consisting of a 5-mer peptide having the amino acid sequence -$M_1M_2M_3M_4M_5$-. Hit maturation may involve any of, or a combination of any or all of, amino acid substitutions, deletions, and insertions at positions 1, 2, 3, 4, and 5. For example, in regard to the hypothetical core hit peptide -$M_1M_2M_3M_4M_5$-, embodiments may include the amino acid M at position 1 being substituted with each of the other amino acids (e.g., $A_1M_2M_3M_4M_5$-, $P_1M_2M_3M_4M_5$-, $V_1M_2M_3M_4M_5$-, $Q_1M_2M_3M_4M_5$-, etc.). Each position (2, 3, 4 and 5) would also have the amino acid M substituted with each of the other 19 amino acids (for example, with position 2 the substitutions would resemble, $M_1A_2M_3M_4M_5$-, $M_1Q_2M_3M_4M_5$-, $M_1P_2M_3M_4M_5$-, $M_1N_2M_3M_4M_5$-, etc.). It should be understood that a peptide (immobilized on an array) is created comprising the substituted and/or deleted and/or inserted sequences of the core hit peptide.

In some embodiments of hit maturation according to the instant disclosure, a double amino acid substitution may be performed. A double amino acid substation includes altering the amino acid at a given position (e.g., an M→P substitution, for example at position 1) and then substituting the amino acid at position 2 with each of the other 19 amino acids the amino acid at position 2. This process is repeated until all possible combinations of positions 1 and 2 are combined. By way of example, referring back to the hypothetical core hit peptide having a 5-mer peptide with amino acid sequence -$M_1M_2M_3M_4M_5$-, a double amino acid substitution with regard to positions 1 and 2 may include, for example, a M→P substitution at position 1, and then a substation of all 20 amino acids at position 2 (e.g., -$P_1A_2M_3M_4M_5$-, -$P_1F_2M_3M_4M_5$-, -$P_1V_2M_3M_4M_5$-, -$P_1E_2M_3M_4M_5$-, etc.), a M→V substitution at position 1, and then a substation of all 20 amino acids at position 2 (e.g., -$V_1A_2M_3M_4M_5$-, -$V_1F_2M_3M_4M_5$-, -$P_1V_2M_3M_4M_5$-, -$V_1E_2M_3M_4M_5$-, etc.), M→A substitution at position 1, and then a substation of all 20 amino acids at position 2 (e.g., -$A_1A_2M_3M_4M_5$-, -$A_1F_2M_3M_4M_5$-, -$A_1V_2M_3M_4M_5$-, -$A_1E_2M_3M_4M_5$-, etc.).

In some embodiments of hit maturation, an amino acid deletion for each amino acid position of the core hit peptide may be performed. An amino acid deletion includes preparing a peptide including the core hit peptide sequence, but deleting a single amino acid from the core hit peptide sequence (such that a peptide is created in which the amino acid at each peptide is deleted). By way of example, referring back to the hypothetical core hit peptide having a 5-mer peptide with amino acid sequence -$M_1M_2M_3M_4M_5$-, an amino acid deletion would include preparing a series of peptides having the following sequences -$M_2M_3M_4M_5$-; -$M_1M_3M_4M_5$-; -$M_1M_2M_4M_5$-; -$M_1M_2M_3M_5$-; and -$M_1M_2M_3M_4$-. It should be noted that, following an amino acid deletion of the hypothetical 5-mer, 5 new 4-mers are created. According to some embodiments an amino acid substitution or a double amino acid substation scan can be performed for each new 4-mer generated.

Similar to the amino acid deletion scan discussed above, some embodiments of hit maturation may include an amino acid insertion scan, whereby each of the 20 amino acids is inserted before and after every position of the core hit peptide. By way of example, referring back to the hypothetical core hit peptide having a 5-mer peptide with amino acid sequence -$M_1M_2M_3M_4M_5$-, an amino acid insertion scan could include the following sequences, -$XM_1M_2M_3M_4M_5$-; -$M_1XM_2M_3M_4M_5$-; -$M_1M_2XM_3M_4M_5$-; -$M_1M_2M_3XM_4M_5$-; -$M_1M_2M_3M_4XM_5$-; and -$M_1M_2M_3M_4M_5X$- (where X represents an individual amino, selected from the 20 known amino acids or a specific, defined subset of amino acids, whereby a peptide replicate will be created for each of the 20 or defined subset of amino acids).

It should also be understood that the amino acid substituted peptides, double amino acid substituted peptides, amino acid deletion scan peptides and amino acid insertion scan peptides described above may also include one, or both of, an N-terminal and C-terminal wobble amino acid sequence. As with the N-terminal and C-terminal wobble amino acid sequences, the N-terminal and C-terminal wobble amino acid sequences may comprise as few as 1 amino acid or as many as 15 or 20 amino acids, and the N-terminal wobble amino acid sequence may be the same length as, longer than or shorter than the C-terminal wobble amino acid sequence. Further, the N-terminal and C-terminal wobble amino acid sequences may comprise any defined group of amino acids at any given ratios (for example, glycine and serine in a 3:1 ratio).

Once the various substitution, deletion, and insertion variations of the core hit peptide are prepared (for example, in immobilized fashion on a solid support such as a microarray), a predetermined property of the purified, concentrated enzyme (e.g., a transglutaminase) is analyzed, for example, under appropriate reaction or binding conditions.

Upon maturation of the core hit peptide (such that a more optimal amino acid sequence of the core hit peptide is identified for binding the transglutaminase, for example), the N-terminal and/or C-terminal positions can undergo an extension step, whereby the length of the matured core hit peptide is further extended for increasing the specificity and affinity for the transglutaminase. According to various embodiments of N-terminal extension of the instant disclosure, once the matured core hit peptide sequence is identified through the maturation process, any specific amino acids, can be added (or synthesized onto) the N-terminal end of a matured core hit peptide, for example. Likewise, according to various embodiments of C-terminal extension of the instant disclosure, once the matured core hit peptide sequence is identified through the maturation process, any specific amino acids can be added (or synthesized onto) the C-terminal end of a matured core hit peptide. According to some embodiments of the instant disclosure, the matured core hit peptides used in C-terminal extension and N-terminal extension may also include one, or both of, an N-terminal and C-terminal wobble amino acid sequence. The N-terminal and C-terminal wobble amino acid sequences may comprise as few as 1 amino acid or as many as 15 or 20 amino acids (or more), and the N-terminal wobble amino acid sequence may be the same length as, longer than, or shorter than the C-terminal wobble amino acid sequence. Further, the N-terminal and C-terminal wobble amino acid sequences may comprise any defined group of amino acids at any given ratios (for example, glycine and serine in a 3:1 ratio). In use, an extension array can be exposed to a concentrated, purified protein of interest (e.g., a transglutaminase), whereby the protein may bind at any peptide of either population, independent of the other peptides comprising the populations. After exposure to the protein of interest, binding or activity, for example, of the protein of interest is assayed, for example, by way of exposing the complex of the individual peptide of the populations and protein to an antibody (specific for the protein) which has a reportable label (e.g., peroxidase) attached thereto (it should also be understood the protein of interest may be directly labelled with a reporter molecule). Because the peptide probe sequence for each location on the array, is known, it is possible to chart/quantify/compare/contrast the sequences (and binding strengths or activity, for example) of the protein in relation to the specific probe comprising the matured core hit peptide. An exemplary method of comparing the protein binding to the matured core hit peptide-peptide probe combination is to review the binding strength in a principled analysis distribution-based clustering, such as described in, *Standardizing and Simplifying Analysis of Peptide Library Data*, Andrew D White et al, J Chem Inf Model, 2013, 53(2), pp 493-499, incorporated herein by reference. Clustering of protein binding to the respective probes shown in a principled analysis distribution-based clustering indicates peptide-probes having overlapping peptide sequences. As demonstrated in greater detail below, from the overlapping peptide sequences (of each cluster), an extended, matured core hit peptide sequence can be identified and constructed for further evaluation. In some embodiments of the instant application, an extended, matured core hit peptide undergoes a subsequent maturation process.

The N-terminal and C-terminal extension processes disclosed herein demonstrate surprising and unexpected results. The N-terminal and C-terminal extension processes do not simply demonstrate a "repeat" of the core hit peptide sequence, but instead show specific and uniform N- and C-terminal amino acid junction sequences, which contribute to increasing the length, specificity and affinity of the matured core hit for the protein of interest.

Following identification of an extended, matured core hit peptide, a specificity analysis may be performed according to some embodiments of the instant disclosure. One example of a specificity analysis includes a BIACORE system analysis which is used for characterizing molecules in terms of the molecules interaction specifically to a target, the kinetic rates (of "on," binding, and "off," disassociation) and affinity (binding strength). An overview of the BIACORE system and process is available from the manufacturer (GE Healthcare). A benefit of BIACORE is the ability to perform the kinetic, specificity and affinity analyses in a label-free manner

What is claimed is:

1. A method of cross-linking at least two compounds, the method comprising:
cross-linking a heterologous transglutaminase glutamine substrate peptide present in a first compound with a lysine substrate present in a second compound by contacting the heterologous transglutaminase glutamine substrate peptide and the lysine substrate with a microbial transglutaminase,
wherein:
the heterologous transglutaminase glutamine substrate peptide comprises the sequence motif [YF][VA]LQG and specifically binds the microbial transglutaminase; and
the microbial transglutaminase is a *Streptomyces mobaraensis* transglutaminase.

2. The method of claim 1, wherein the heterologous transglutaminase glutamine substrate peptide comprises the sequence motif GDYALQGPG (SEQ ID NO: 79).

3. The method of claim 1, wherein the lysine substrate is a heterologous transglutaminase lysine substrate peptide, the method further comprising the steps of incorporating the heterologous transglutaminase glutamine substrate peptide into the first compound and the heterologous transglutaminase lysine substrate peptide into the second compound.

4. The method of claim 3, wherein the heterologous transglutaminase lysine substrate peptide comprises a sequence motif selected from SK[LS]K and [KR][ST]KL.

5. The method of claim 1, wherein at least one of the first compound and the second compound is a Vitamin D binding protein.

6. The method of claim 3, wherein the first compound is a Vitamin D binding protein, and wherein the heterologous transglutaminase glutamine substrate peptide comprises the sequence GGGGDYALQGGGG (SEQ ID NO: 85).

7. The method of claim 6, wherein the second compound comprises a label, and wherein the heterologous transglutaminase lysine substrate peptide is incorporated into the label.

8. The method of claim 7, wherein the label with the incorporated heterologous transglutaminase lysine substrate peptide is a compound with a formula selected from the group consisting of:

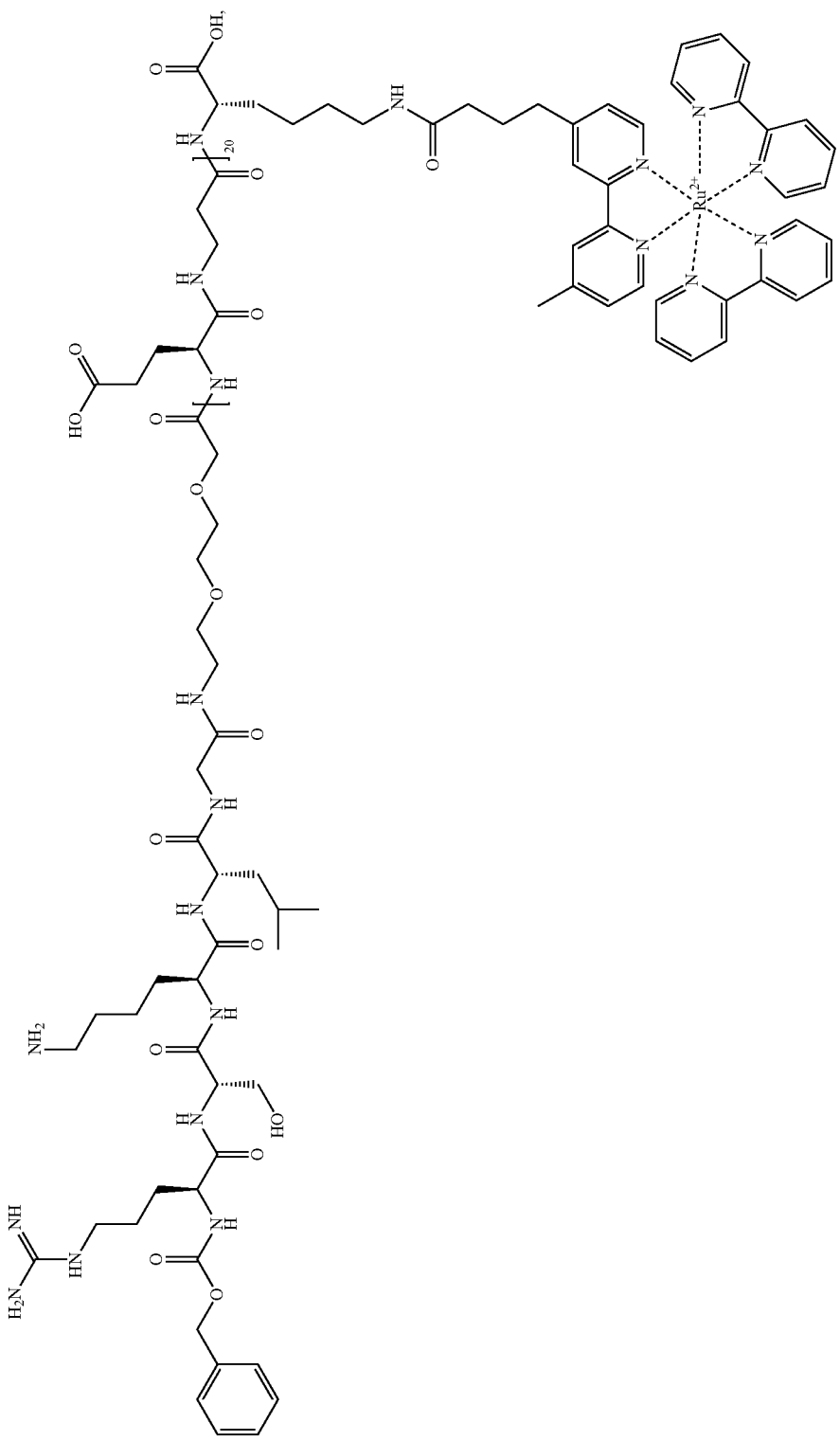

119 120
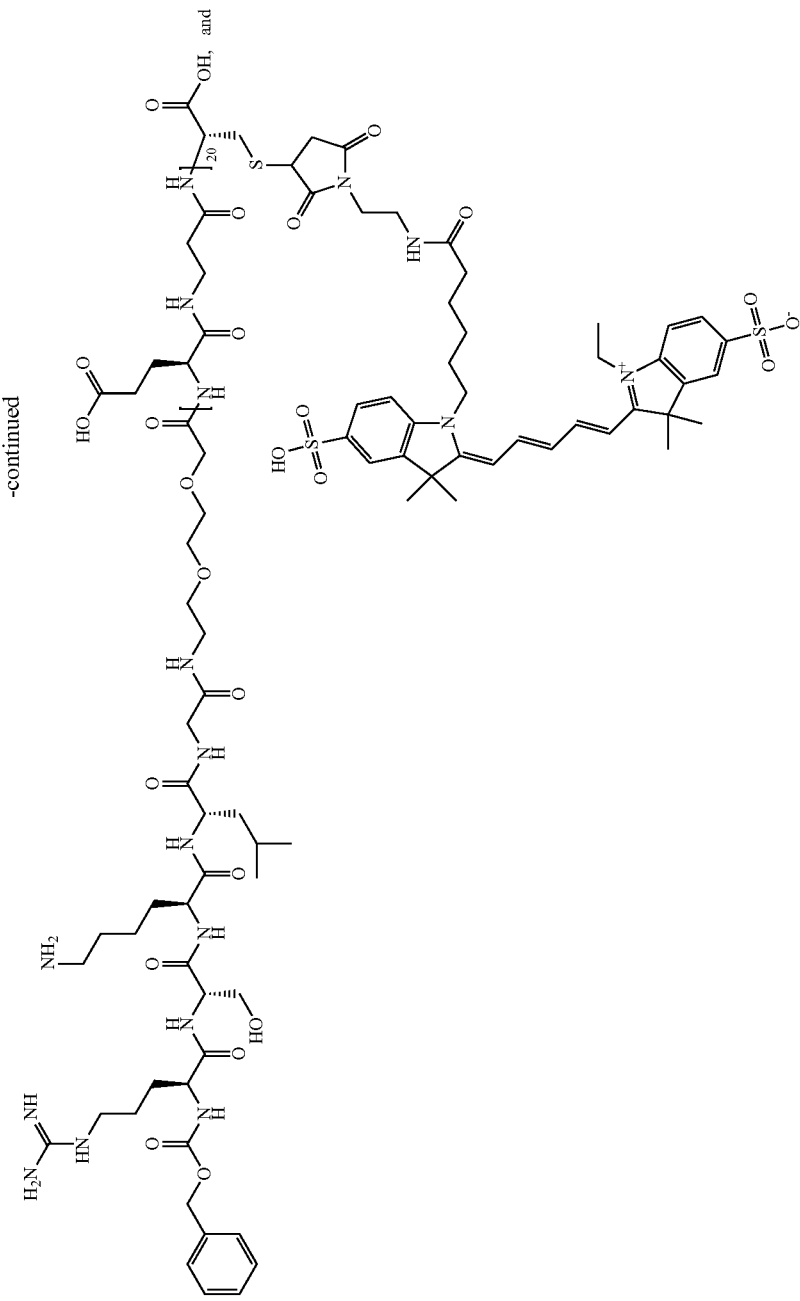
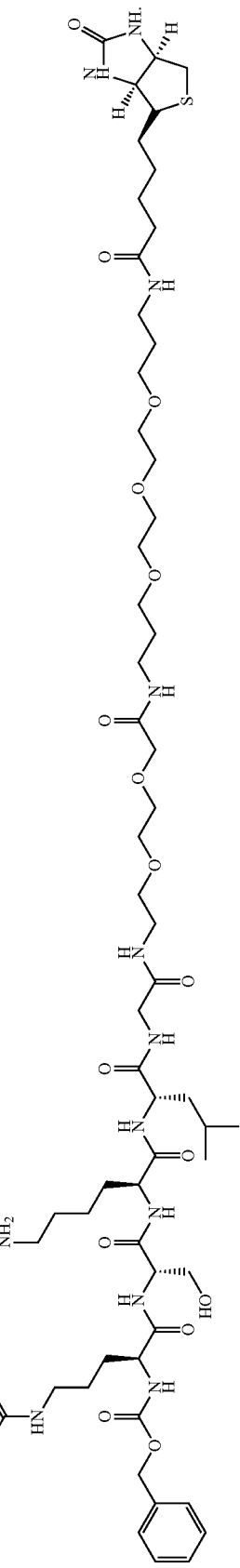

9. A method of cross-linking at least two compounds, the method comprising:

cross-linking a heterologous transglutaminase glutamine substrate peptide present in a first compound with a lysine substrate present in a second compound by contacting the heterologous transglutaminase glutamine substrate peptide and the lysine substrate with a microbial transglutaminase, wherein:

the heterologous transglutaminase glutamine substrate peptide comprises the sequence motif [YF][VA]LQG and specifically binds the microbial transglutaminase; and the microbial transglutaminase is a *Streptoverticillium* sp. transglutaminase.

10. The method of claim 1, wherein the first compound is a protein comprising an N-terminus and a C-terminus and the heterologous transglutaminase glutamine substrate peptide is attached to the N-terminus or the C-terminus of the protein.

11. The method of claim 1, wherein the glutamine substrate peptide comprises the sequence motif selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), and a combination thereof.

12. The method of claim 11, wherein the lysine substrate comprises a sequence motif selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), and a combination thereof.

13. The method of claim 1, wherein the lysine substrate comprises a sequence motif selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), and a combination thereof.

14. A method of cross-linking at least two compounds, the method comprising the steps of:

cross-linking a heterologous transglutaminase glutamine substrate peptide present in a first compound with a lysine substrate present in a second compound, wherein:

the cross-linking comprises allowing the heterologous transglutaminase glutamine substrate peptide and the lysine substrate to come in contact with the microbial transglutaminase whereby the microbial transglutaminase catalyzes the formation of an isopeptide bond between a γ-carboxamide group of a glutamine residue in the sequence motif [YF][VA]LQG and an ε-amino group of a lysine residue in the lysine substrate; and the microbial transglutaminase is a *Streptomyces mobaraensis* transglutaminase.

15. The method of claim 14, wherein the heterologous transglutaminase glutamine substrate peptide comprises the sequence motif selected from the group consisting of GGGDYALQGGG (SEQ ID NO:26), CGGDYALQGPG (SEQ ID NO:27), WGGDYALQGPG (SEQ ID NO:28), YGGDYALQGPG (SEQ ID NO:29), DGGDYALQGPG (SEQ ID NO:30), GDGDYALQGPG (SEQ ID NO:31), NGGDYALQGPG (SEQ ID NO:32), GCGDYALQGPG (SEQ ID NO:33), EGGDYALQGPG (SEQ ID NO:34), PGGDYALQGPG (SEQ ID NO:35), TGGDYALQGPG (SEQ ID NO:36), QGGDYALQGPG (SEQ ID NO:37), IGGDYALQGPG (SEQ ID NO:38), FGGDYALQGPG (SEQ ID NO:39), HGGDYALQGPG (SEQ ID NO:40), LGGDYALQGPG (SEQ ID NO:41), VGGDYALQGPG (SEQ ID NO:42), RGGDYALQGPG (SEQ ID NO:43), GWGDYALQGPG (SEQ ID NO:44), MGGDYALQGPG (SEQ ID NO:45), SGGDYALQGPG (SEQ ID NO:46), AGGDYALQGPG (SEQ ID NO:47), GYGDYALQGPG (SEQ ID NO:48), GEGDYALQGPG (SEQ ID NO:49), GPGDYALQGPG (SEQ ID NO:50), GHGDYALQGPG (SEQ ID NO:51), WDGDYALQGGG (SEQ ID NO:52), GGGGDYALQGGGG (SEQ ID NO: 85), GGGDYALQGGGG (SEQ ID NO: 86), and GNGDYALQGPG (SEQ ID NO: 53), and a combination thereof.

16. The method of claim 15, wherein the lysine substrate comprises a sequence motif selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGAR- SKLGGGG (SEQ ID NO: 80), and GYKLK (SEQ ID NO:78), and a combination thereof.

17. The method of claim 14, wherein the lysine substrate comprises a sequence motif selected from the group consisting of ARSKL (SEQ ID NO:54), KSKLA (SEQ ID NO:55), TKSKL (SEQ ID NO:56), KLSKL (SEQ ID NO:57), RSKLG (SEQ ID NO:58), RGSKL (SEQ ID NO:59), RGTKL (SEQ ID NO:60), FPKLK (SEQ ID NO:61), RSKSK (SEQ ID NO:62), SKSKL (SEQ ID NO:63), FTKSK (SEQ ID NO:64), KLKYK (SEQ ID NO:65), PKTKL (SEQ ID NO:66), RLKSK (SEQ ID NO:67), RSKLA (SEQ ID NO:68), GRSKL (SEQ ID NO:69), RAKYK (SEQ ID NO:70), SKLSK (SEQ ID NO:71), KLGAK (SEQ ID NO:72), QRSKL (SEQ ID NO:73), KTKYK (SEQ ID NO:74), LSKLK (SEQ ID NO:75), NRTKL (SEQ ID NO:76), QRTKL (SEQ ID NO:77), GGGRSKLAGGG (SEQ ID NO: 82), GGGARSKLGGGG (SEQ ID NO: 80), and GYKLK (SEQ ID NO:78), and a combination thereof.

* * * * *

SEQUENCE LISTING

<160> NUMBER OF SEQ ID NOS: 91

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Asp Tyr Ala Leu Gln
1               5

```
<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Asp Tyr Val Leu Gln
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Asn Tyr Ala Leu Gln
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Glu Tyr Ala Leu Gln
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Pro Tyr Ala Leu Gln
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Glu Tyr Val Leu Gln
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Asp Phe Ala Leu Gln
1               5
```

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Asp Tyr Phe Leu Gln
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic peptide

<400> SEQUENCE: 9

Asn Tyr Phe Leu Gln
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic peptide

<400> SEQUENCE: 10

Phe Tyr Ala Leu Gln
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide

<400> SEQUENCE: 11

Asp Tyr Thr Leu Gln
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Asn Tyr Val Leu Gln
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide

<400> SEQUENCE: 13

Glu Tyr Val Ala Gln
1               5

```
<210> SEQ ID NO 14
<211> LENGTH: 5
<212> TYPE: PRT
<213> ORGANISM: Artificial Sequence
<220> FEATURE:
<223> OTHER INFORMATION: synthetic peptide

<400> SEQUENCE: 14

Arg Tyr Ala Leu Gln
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic peptide

<400> SEQUENCE: 15

Tyr Phe Ala Leu Gln
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic peptide

<400> SEQUENCE: 16

Pro Tyr Val Leu Gln
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Trp Tyr Ala Leu Gln
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide

<400> SEQUENCE: 18

Ser Tyr Ala Leu Gln
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide

<400> SEQUENCE: 19

His Tyr Ala Leu Gln
1               5

<210> SEQ ID NO 20
```

```
<211> LENGTH: 5
<212> TYPE: PRT
<213> ORGANISM: Artificial Sequence
<220> FEATURE:
<223> OTHER INFORMATION: synthetic peptide

<400> SEQUENCE: 20

Asp Tyr Val Ala Gln
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic peptide

<400> SEQUENCE: 21

Glu Phe Val Ala Gln
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic peptide

<400> SEQUENCE: 22

Asp Phe Tyr Leu Gln
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic peptide

<400> SEQUENCE: 23

Glu Phe Ala Leu Gln
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic peptide

<400> SEQUENCE: 24

Glu Tyr Phe Leu Gln
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic peptide

<400> SEQUENCE: 25

Asn Phe Val Leu Gln
1               5

<210> SEQ ID NO 26
<211> LENGTH: 11
```

```
<212> TYPE: PRT
<213> ORGANISM: Artificial Sequence
<220> FEATURE:
<223> OTHER INFORMATION: synthetic peptide

<400> SEQUENCE: 26

Gly Gly Gly Asp Tyr Ala Leu Gln Gly Gly Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: synthetic peptide

<400> SEQUENCE: 27

Cys Gly Gly Asp Tyr Ala Leu Gln Gly Pro Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: synthetic peptide

<400> SEQUENCE: 28

Trp Gly Gly Asp Tyr Ala Leu Gln Gly Pro Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthetic peptide

<400> SEQUENCE: 29

Tyr Gly Gly Asp Tyr Ala Leu Gln Gly Pro Gly
1               5                   10

<210> SEQ ID NO 30
<211> LENGTH: 11
<212> TYPE: PRT
<213> ORGANISM: Artificial Sequence
<220> FEATURE:
<223> OTHER INFORMATION: synthetic peptide

<400> SEQUENCE: 30

Asp Gly Gly Asp Tyr Ala Leu Gln Gly Pro Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: synthetic peptide

<400> SEQUENCE: 31

Gly Asp Gly Asp Tyr Ala Leu Gln Gly Pro Gly
1               5                   10

<210> SEQ ID NO 32
<211> LENGTH: 11
<212> TYPE: PRT
```

<213> ORGANISM: Artificial Sequence
<220> FEATURE:
<223> OTHER INFORMATION: synthetic peptide

<400> SEQUENCE: 32

Asn Gly Gly Asp Tyr Ala Leu Gln Gly Pro Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: synthetic peptide

<400> SEQUENCE: 33

Gly Cys Gly Asp Tyr Ala Leu Gln Gly Pro Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: synthetic peptide

<400> SEQUENCE: 34

Glu Gly Gly Asp Tyr Ala Leu Gln Gly Pro Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: synthetic peptide

<400> SEQUENCE: 35

Pro Gly Gly Asp Tyr Ala Leu Gln Gly Pro Gly
1               5                   10

<210> SEQ ID NO 36
<211> LENGTH: 11
<212> TYPE: PRT
<213> ORGANISM: Artificial Sequence
<220> FEATURE:
<223> OTHER INFORMATION: synthetic peptide

<400> SEQUENCE: 36

Thr Gly Gly Asp Tyr Ala Leu Gln Gly Pro Gly
1               5                   10

<210> SEQ ID NO 37
<211> LENGTH: 11
<212> TYPE: PRT
<213> ORGANISM: Artificial Sequence
<220> FEATURE:
<223> OTHER INFORMATION: synthetic peptide

<400> SEQUENCE: 37

Gln Gly Gly Asp Tyr Ala Leu Gln Gly Pro Gly
1               5                   10

<210> SEQ ID NO 38
<211> LENGTH: 11
<212> TYPE: PRT
<213> ORGANISM: Artificial Sequence
<220> FEATURE:
<223> OTHER INFORMATION: synthetic peptide

<400> SEQUENCE: 38

Ile Gly Gly Asp Tyr Ala Leu Gln Gly Pro Gly
1               5                   10

<210> SEQ ID NO 39
<211> LENGTH: 11
<212> TYPE: PRT
<213> ORGANISM: Artificial Sequence
<220> FEATURE:
<223> OTHER INFORMATION: synthetic peptide

<400> SEQUENCE: 39

Phe Gly Gly Asp Tyr Ala Leu Gln Gly Pro Gly
1               5                   10

<210> SEQ ID NO 40
<211> LENGTH: 11
<212> TYPE: PRT
<213> ORGANISM: Artificial Sequence
<220> FEATURE:
<223> OTHER INFORMATION: synthetic peptide

<400> SEQUENCE: 40

His Gly Gly Asp Tyr Ala Leu Gln Gly Pro Gly
1               5                   10

<210> SEQ ID NO 41
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 41

Leu Gly Gly Asp Tyr Ala Leu Gln Gly Pro Gly
1               5                   10

<210> SEQ ID NO 42
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 42

Val Gly Gly Asp Tyr Ala Leu Gln Gly Pro Gly
1               5                   10

<210> SEQ ID NO 43
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 43

Arg Gly Gly Asp Tyr Ala Leu Gln Gly Pro Gly
1               5                   10

<210> SEQ ID NO 44
<211> LENGTH: 11
<212> TYPE: PRT
<213> ORGANISM: Artificial Sequence
<220> FEATURE:

```
<223> OTHER INFORMATION: synthetic peptide sequence

<400> SEQUENCE: 44

Gly Trp Gly Asp Tyr Ala Leu Gln Gly Pro Gly
1               5                   10

<210> SEQ ID NO 45
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 45

Met Gly Gly Asp Tyr Ala Leu Gln Gly Pro Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 46

Ser Gly Gly Asp Tyr Ala Leu Gln Gly Pro Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 47

Ala Gly Gly Asp Tyr Ala Leu Gln Gly Pro Gly
1               5                   10

<210> SEQ ID NO 48
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 48

Gly Tyr Gly Asp Tyr Ala Leu Gln Gly Pro Gly
1               5                   10

<210> SEQ ID NO 49
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 49

Gly Glu Gly Asp Tyr Ala Leu Gln Gly Pro Gly
1               5                   10

<210> SEQ ID NO 50
<211> LENGTH: 11
<212> TYPE: PRT
<213> ORGANISM: Artificial Sequence
<220> FEATURE:
<223> OTHER INFORMATION: synthetic peptide sequence
```

<400> SEQUENCE: 50

Gly Pro Gly Asp Tyr Ala Leu Gln Gly Pro Gly
1               5                   10

<210> SEQ ID NO 51
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 51

Gly His Gly Asp Tyr Ala Leu Gln Gly Pro Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 52

Trp Asp Gly Asp Tyr Ala Leu Gln Gly Gly Gly
1               5                   10

<210> SEQ ID NO 53
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 53

Gly Asn Gly Asp Tyr Ala Leu Gln Gly Pro Gly
1               5                   10

<210> SEQ ID NO 54
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 54

Ala Arg Ser Lys Leu
1               5

<210> SEQ ID NO 55
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 55

Lys Ser Lys Leu Ala
1               5

<210> SEQ ID NO 56
<211> LENGTH: 5
<212> TYPE: PRT
<213> ORGANISM: Artificial Sequence
<220> FEATURE:
<223> OTHER INFORMATION: synthetic peptide sequence

```
<400> SEQUENCE: 56

Thr Lys Ser Lys Leu
1               5

<210> SEQ ID NO 57
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 57

Lys Leu Ser Lys Leu
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 58

Arg Ser Lys Leu Gly
1               5

<210> SEQ ID NO 59
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 59

Arg Gly Ser Lys Leu
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 60

Arg Gly Thr Lys Leu
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 61

Phe Pro Lys Leu Lys
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 62
```

Arg Ser Lys Ser Lys
1               5

<210> SEQ ID NO 63
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 63

Ser Lys Ser Lys Leu
1               5

<210> SEQ ID NO 64
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 64

Phe Thr Lys Ser Lys
1               5

<210> SEQ ID NO 65
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 65

Lys Leu Lys Tyr Lys
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 66

Pro Lys Thr Lys Leu
1               5

<210> SEQ ID NO 67
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 67

Arg Leu Lys Ser Lys
1               5

<210> SEQ ID NO 68
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 68

Arg Ser Lys Leu Ala
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 69

Gly Arg Ser Lys Leu
1               5

<210> SEQ ID NO 70
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 70

Arg Ala Lys Tyr Lys
1               5

<210> SEQ ID NO 71
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 71

Ser Lys Leu Ser Lys
1               5

<210> SEQ ID NO 72
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 72

Lys Leu Gly Ala Lys
1               5

<210> SEQ ID NO 73
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 73

Gln Arg Ser Lys Leu
1               5

<210> SEQ ID NO 74
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 74

Lys Thr Lys Tyr Lys

```
<210> SEQ ID NO 75
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 75

Leu Ser Lys Leu Lys
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 76

Asn Arg Thr Lys Leu
1               5

<210> SEQ ID NO 77
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 77

Gln Arg Thr Lys Leu
1               5

<210> SEQ ID NO 78
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 78

Gly Tyr Lys Leu Lys
1               5

<210> SEQ ID NO 79
<211> LENGTH: 9
<212> TYPE: PRT
<213> ORGANISM: Artificial Sequence
<220> FEATURE:
<223> OTHER INFORMATION: synthetic peptide sequence

<400> SEQUENCE: 79

Gly Asp Tyr Ala Leu Gln Gly Pro Gly
1               5

<210> SEQ ID NO 80
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 80

Gly Gly Gly Ala Arg Ser Lys Leu Gly Gly Gly Gly
1               5                   10
```

<210> SEQ ID NO 81
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 81

Gly Gly Gly Asp Glu Lys Pro Asp Gly Gly Gly Gly
1               5                   10

<210> SEQ ID NO 82
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 82

Gly Gly Gly Arg Ser Lys Leu Ala Gly Gly Gly
1               5                   10

<210> SEQ ID NO 83
<211> LENGTH: 21
<212> TYPE: PRT
<213> ORGANISM: Artificial Sequence
<220> FEATURE:
<223> OTHER INFORMATION: synthetic peptide sequence

<400> SEQUENCE: 83

His His His His His His His His Gly Gly Gly Gly Asp Tyr Ala Leu
1               5                   10                  15

Gln Gly Gly Gly Gly
            20

<210> SEQ ID NO 84
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 84

His His His His His His His His
1               5

<210> SEQ ID NO 85
<211> LENGTH: 13
<212> TYPE: PRT
<213> ORGANISM: Artificial Sequence
<220> FEATURE:
<223> OTHER INFORMATION: synthetic peptide sequence

<400> SEQUENCE: 85

Gly Gly Gly Gly Asp Tyr Ala Leu Gln Gly Gly Gly Gly
1               5                   10

<210> SEQ ID NO 86
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 86

```
Gly Gly Gly Asp Tyr Ala Leu Gln Gly Gly Gly Gly
1               5                   10
```

<210> SEQ ID NO 87
<211> LENGTH: 499
<212> TYPE: PRT
<213> ORGANISM: Artificial Sequence
<220> FEATURE:
<223> OTHER INFORMATION: synthetic peptide sequence
<220> FEATURE:
<221> NAME/KEY: MISC_FEATURE
<222> LOCATION: (1)..(474)
<223> OTHER INFORMATION: Vitamin D binding protein
<220> FEATURE:
<221> NAME/KEY: MISC_FEATURE
<222> LOCATION: (479)..(486)
<223> OTHER INFORMATION: 8X Histidine Tag
<220> FEATURE:
<221> NAME/KEY: MISC_FEATURE
<222> LOCATION: (486)..(499)
<223> OTHER INFORMATION: Transglutaminase substrate tag

<400> SEQUENCE: 87

```
Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285
```

Leu Ser Thr Lys Asn Ser Lys Phe Glu Asp Cys Cys Gln Glu Lys Thr
            290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys Arg Ser Asp Phe
        435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu Gly Gly Ser His His
465                 470                 475                 480

His His His His His Gly Gly Gly Gly Asp Tyr Ala Leu Gln Gly
                485                 490                 495

Gly Gly Gly

<210> SEQ ID NO 88
<211> LENGTH: 35
<212> TYPE: DNA
<213> ORGANISM: Artificial Sequence
<220> FEATURE:
<223> OTHER INFORMATION: synthetic primer sequence

<400> SEQUENCE: 88
cagacataat agctgacaga ctaacagact gttcc                              35

<210> SEQ ID NO 89
<211> LENGTH: 82
<212> TYPE: DNA
<213> ORGANISM: Artificial Sequence
<220> FEATURE:
<223> OTHER INFORMATION: synthetic primer sequence

<400> SEQUENCE: 89
gtgatctgga tccttatcac acctcgatgt ggtcgggcag gtccacgatc tttccaccgt    60
gatggtggtg atggtggtga tg                                            82

<210> SEQ ID NO 90
<211> LENGTH: 28
<212> TYPE: DNA
<213> ORGANISM: Artificial Sequence
<220> FEATURE:
<223> OTHER INFORMATION: synthetic primer sequence

<400> SEQUENCE: 90
gtgatctgga tccttatcaa ccgcctcc                                      28

```
<210> SEQ ID NO 91
<211> LENGTH: 483
<212> TYPE: PRT
<213> ORGANISM: Artificial Sequence
<220> FEATURE:
<223> OTHER INFORMATION: synthetic peptide sequence
<220> FEATURE:
<221> NAME/KEY: MISC_FEATURE
<222> LOCATION: (1)..(458)
<223> OTHER INFORMATION: Mature Vitamin D Binding Protein
<220> FEATURE:
<221> NAME/KEY: MISC_FEATURE
<222> LOCATION: (463)..(470)
<223> OTHER INFORMATION: 8X Histidine Tag
<220> FEATURE:
<221> NAME/KEY: MISC_FEATURE
<222> LOCATION: (471)..(483)
<223> OTHER INFORMATION: Transglutaminase substrate tag

<400> SEQUENCE: 91

Leu Glu Arg Gly Arg Asp Tyr Glu Lys Asn Lys Val Cys Lys Glu Phe
 1               5                  10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
 50                  55                  60

Pro Asp Cys Tyr Asp Thr Arg Thr Ser Ala Leu Ser Ala Lys Ser Cys
 65                  70                  75                  80

Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly Glu Lys Lys Ser Arg Leu Ser Asn Leu Ile Lys Leu Ala
210                 215                 220

Gln Lys Val Pro Thr Ala Asp Leu Glu Asp Val Leu Pro Leu Ala Glu
225                 230                 235                 240

Asp Ile Thr Asn Ile Leu Ser Lys Cys Cys Glu Ser Ala Ser Glu Asp
                245                 250                 255

Cys Met Ala Lys Glu Leu Pro Glu His Thr Val Lys Leu Cys Asp Asn
            260                 265                 270

Leu Ser Thr Lys Asn Ser Lys Phe Glu Asp Cys Cys Gln Glu Lys Thr
        275                 280                 285

Ala Met Asp Val Phe Val Cys Thr Tyr Phe Met Pro Ala Ala Gln Leu
290                 295                 300
```

```
Pro Glu Leu Pro Asp Val Glu Leu Pro Thr Asn Lys Asp Val Cys Asp
305                 310                 315                 320

Pro Gly Asn Thr Lys Val Met Asp Lys Tyr Thr Phe Glu Leu Ser Arg
                325                 330                 335

Arg Thr His Leu Pro Glu Val Phe Leu Ser Lys Val Leu Glu Pro Thr
            340                 345                 350

Leu Lys Ser Leu Gly Glu Cys Cys Asp Val Glu Asp Ser Thr Thr Cys
        355                 360                 365

Phe Asn Ala Lys Gly Pro Leu Leu Lys Lys Glu Leu Ser Ser Phe Ile
        370                 375                 380

Asp Lys Gly Gln Glu Leu Cys Ala Asp Tyr Ser Glu Asn Thr Phe Thr
385                 390                 395                 400

Glu Tyr Lys Lys Lys Leu Ala Glu Arg Leu Lys Ala Lys Leu Pro Asp
                405                 410                 415

Ala Thr Pro Thr Glu Leu Ala Lys Leu Val Asn Lys Arg Ser Asp Phe
            420                 425                 430

Ala Ser Asn Cys Cys Ser Ile Asn Ser Pro Pro Leu Tyr Cys Asp Ser
        435                 440                 445

Glu Ile Asp Ala Glu Leu Lys Asn Ile Leu Gly Gly Gly Ser His His
    450                 455                 460

His His His His His His Gly Gly Gly Gly Asp Tyr Ala Leu Gln Gly
465                 470                 475                 480

Gly Gly Gly
```